(12) United States Patent
Tsuge et al.

(10) Patent No.: US 10,655,133 B2
(45) Date of Patent: May 19, 2020

(54) METHOD FOR PREPARING DNA UNIT COMPOSITION, AND METHOD FOR CREATING CONCATENATED DNA

(71) Applicant: Synplogen Co., Ltd., Kobe-shi, Hyogo (JP)

(72) Inventors: Kenji Tsuge, Tsuruoka (JP); Mitsuhiro Itaya, Tsuruoka (JP)

(73) Assignee: SYNPLOGEN CO., LTD., Hyogo (JP)

( * ) Notice: Subject to any disclaimer, the term of this patent is extended or adjusted under 35 U.S.C. 154(b) by 497 days.

(21) Appl. No.: 15/113,222

(22) PCT Filed: Sep. 5, 2014

(86) PCT No.: PCT/JP2014/073579
§ 371 (c)(1),
(2) Date: Jul. 21, 2016

(87) PCT Pub. No.: WO2015/111248
PCT Pub. Date: Jul. 30, 2015

(65) Prior Publication Data
US 2017/0009243 A1    Jan. 12, 2017

(30) Foreign Application Priority Data
Jan. 21, 2014   (JP) ................. 2014-008690

(51) Int. Cl.
| | | |
|---|---|---|
| *C12Q 1/68* | (2018.01) | |
| *C07H 21/00* | (2006.01) | |
| *C12N 15/03* | (2006.01) | |
| *C12N 15/64* | (2006.01) | |
| *C12N 15/66* | (2006.01) | |
| *C12N 15/10* | (2006.01) | |

(52) U.S. Cl.
CPC ............ *C12N 15/64* (2013.01); *C12N 15/10* (2013.01); *C12N 15/66* (2013.01)

(58) Field of Classification Search
CPC ........... C12Q 1/68; C12N 15/09; C07H 21/00
See application file for complete search history.

(56) References Cited

U.S. PATENT DOCUMENTS

| | | | | |
|---|---|---|---|---|
| 2002/0137134 A1* | 9/2002 | Gerngross | ............... | C12N 1/14 435/69.1 |
| 2003/0148420 A1* | 8/2003 | Suzanne | ............... | C07K 14/38 435/69.1 |
| 2007/0031920 A1 | 2/2007 | Prentice | | |
| 2011/0263024 A1* | 10/2011 | Marillonnet | ........... | C12N 15/64 435/440 |
| 2018/0010156 A1* | 1/2018 | Nomura | ............... | C12N 9/1029 |

FOREIGN PATENT DOCUMENTS

| | | |
|---|---|---|
| JP | 2004129654 A | 4/2004 |
| JP | 2006503583 A | 2/2006 |
| JP | 4479199 B2 | 6/2010 |
| WO | 0214490 A2 | 2/2002 |

OTHER PUBLICATIONS

Engler et al.,A One Pot, One Step, Precision Cloning Method with High Throughput Capability . PLoS one 3(11) : e3647. (Year: 2008).*
Engler et al., Golden Gate Shuffling: A One-Pot DNA Shuffling Method Based on Type IIs Restriction Enzymes. PLoS one 4(5) : e5553 (Year: 2009).*
Stemmer et al., Gene 164 :49 (Year: 1995).*
Extended European Search Report corresponding to Application No. 14879862.2-1404/3098310 PCT/JP2014073579; dated May 12, 2017.
K. Tsuge et al., "Method of preparing an equimolar DNA mixture for one-step DNA assembly of over 50 fragments," Scientific Reports, May 20, 2015, vol. 5, No. 1, pp. 1-11.
K. Tsuge et al., "One step assembly of multiple DNA fragments with a designed order and orientation in Bacillus subtilis plasmid," Nucleic Acids Research, Information Retrieved Ltd., vol. 31, No. 21, Nov. 1, 2003, pp. 1-8.
R. Godiska et al., "Linear plasmid vector for cloning of repetitive or unstable sequences in *Escherichia coli*," Nucleic Acids Research, Dec. 29, 2009, vol. 38, No. 6, pp. 1-9.
Edited by Takaaki Tamura, 4 DNA no Kenshutsu, Kaitei Idenshi Kogaku Jikken Note 1st volume, DNA o Eru [Toriatsukai no Kihon to Chushutsu Seisei Bunri], 2nd edition, 6th print, Yodosha Co., Ltd., 2006, pp. 28 to 29, with partial English translation.
Edited by Yasuko Nishino, Researcher Interview No. 3 Koshi Kenji Tsuge, Keio IAB Research Digest, 2009, vol. 2, pp. 8 to 11.
Hiromichi Sawaki et al., "Development of quantitative PCR array for studying human glycogens expression profiling", Japan Journal of Molecular Tumor Marker Research, 2009, vol. 24, p. 29, with English abstract.
Itaya, M. et al., Construction and Manipulation of Giant DNA by a Genome Vector, Methods in Enzymology, 2011, vol. 498, pp. 427-447, 4.4.
Kenji Tsuge et al., "Genome Builder Oyobi Genome Designer to shite no Kosokin", Journal of the Society for Bioscience and Bioengineering, Japan, 2012, vol. 90, No. 6, pp. 281 to 284.
Mitsuhiro Itaya et al., "Chosa DNA no Gosei to Gosei Seibutsu Kogaku deno Katsuyo", Journal of the Society for Bioscience and Bioengineering, Japan, 2013, vol. 91, No. 6, pp. 319 to 321.
Tsuge, K. et al., Production of the non-ribosomal peptide plipastatin in Bacillus subtilis regulated by three relevant gene blocks assembled in a single movable DNA segment, Journal of Biotechnology, 2007, vol. 129, pp. 592-603.
International Search Report corresponding to Application No. PCT/JP2014/073579; dated Dec. 9, 2014, with English translation.

\* cited by examiner

*Primary Examiner* — Ethan C Whisenant
(74) *Attorney, Agent, or Firm* — Cantor Colburn LLP

(57) ABSTRACT

Provided are: a method for preparing a DNA unit composition in which the mol number of a plurality of DNA units is more uniform, and a method for creating concatenated DNA. The method for preparing a DNA unit composition has: a step for preparing solutions which contain a plurality of DNA units to which an added sequence is linked, and preparing a solution for each type of DNA unit; and a step for, after preparing each of the solutions, measuring the concentration of the DNA unit in each of the solutions in a state where the added sequence is linked to the DNA unit, and on the basis of the results thereof, fractionating each of the solutions and making the mol number of the DNA unit in each of the solutions closer to being identical to one another.

13 Claims, 23 Drawing Sheets
Specification includes a Sequence Listing.

FIG. 2

```
9510       9520
 |          |
ttccagccGgagggcgta        WILD-TYPE SEQUENCE
F  Q  P  E  G  V
```

⬇

```
9510       9520
 |          |
ttccagccCgagggcgta        VARIANT WITH SYNONYMOUS CODON
F  Q  P  E  G  V           SUBSTITUTION
     ‿‿‿                  (J02459.1:g.9515G>C)
     AvaI
```

FIG. 15
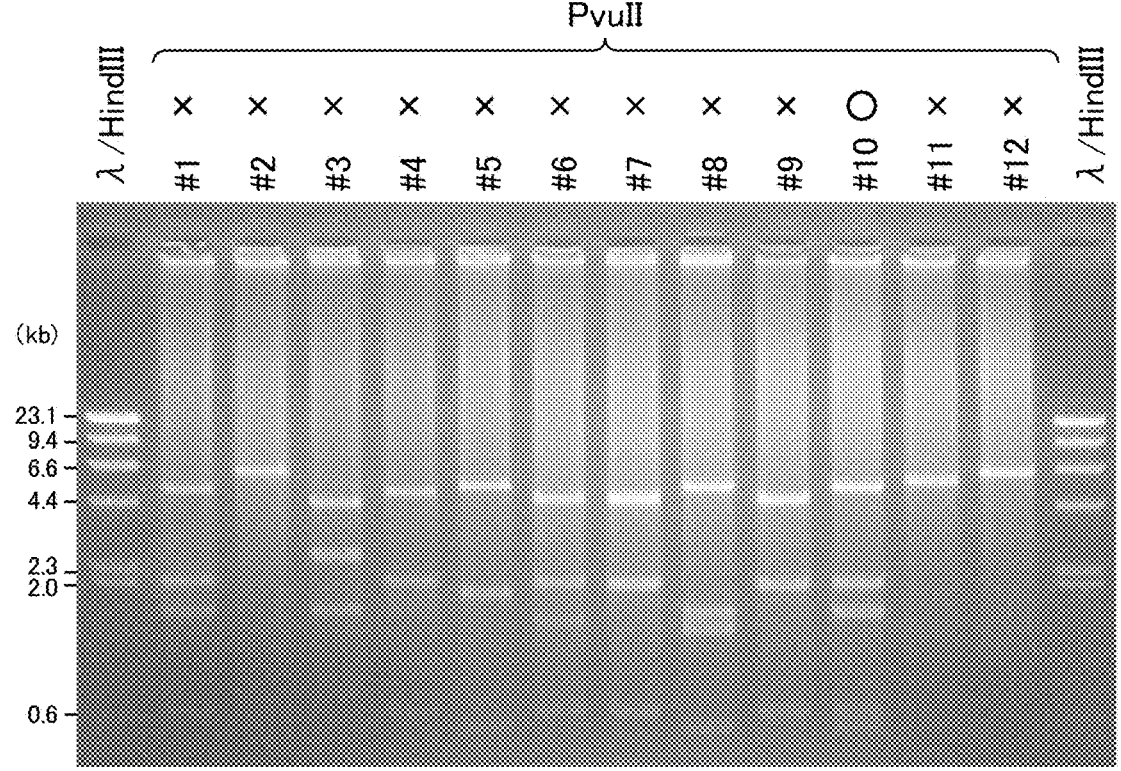
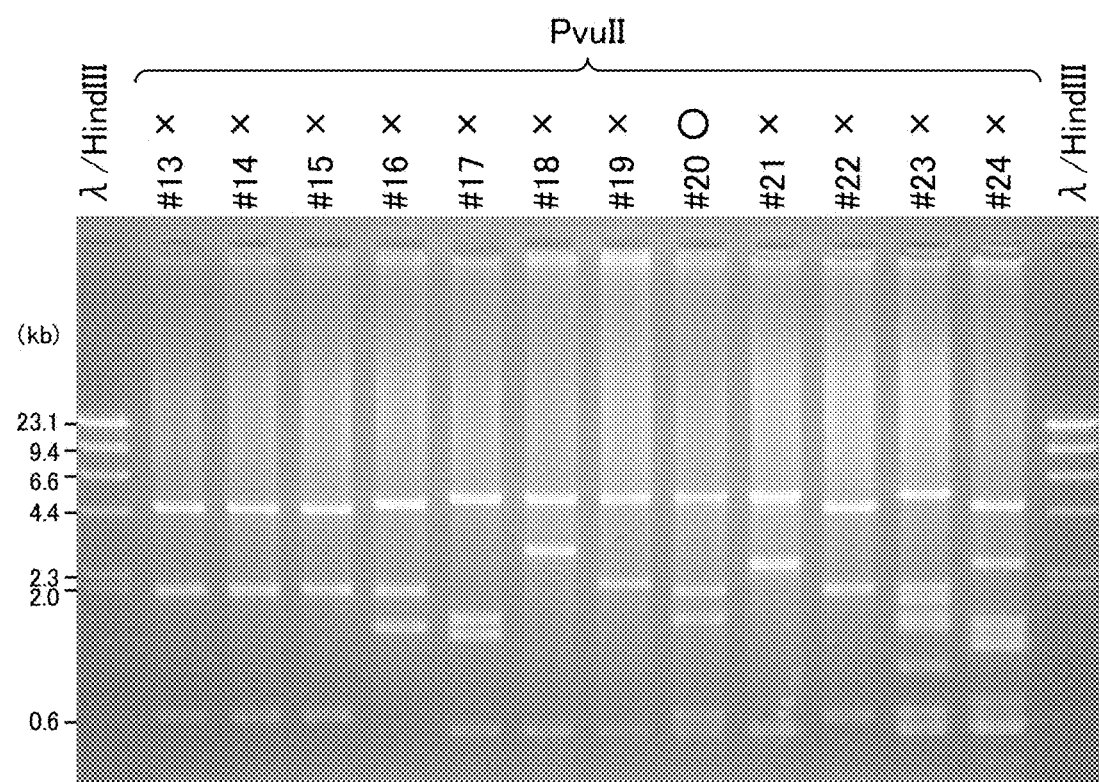

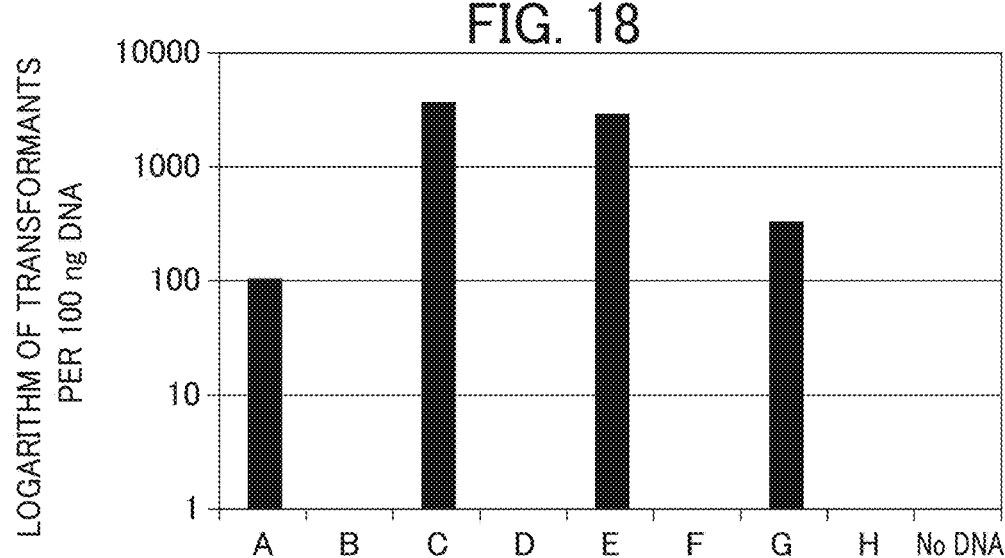
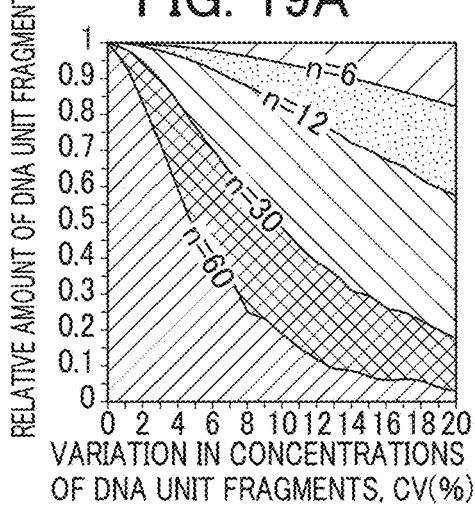
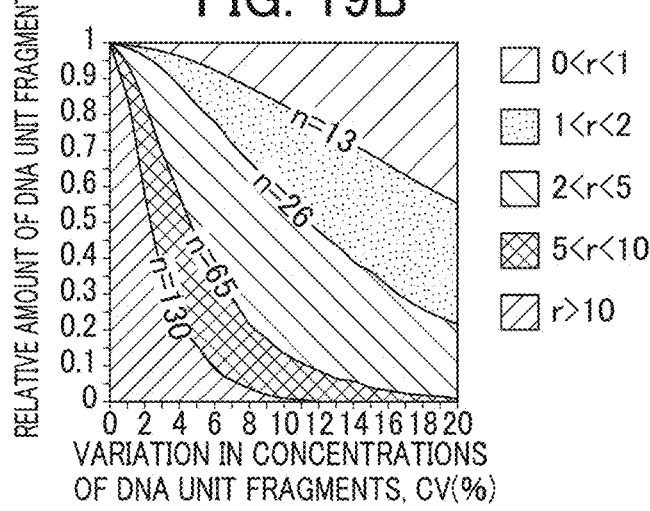
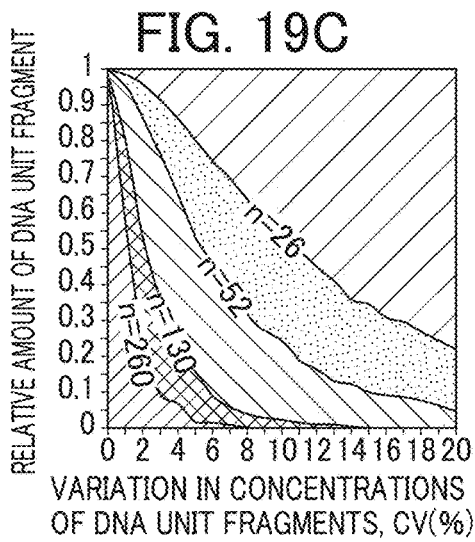
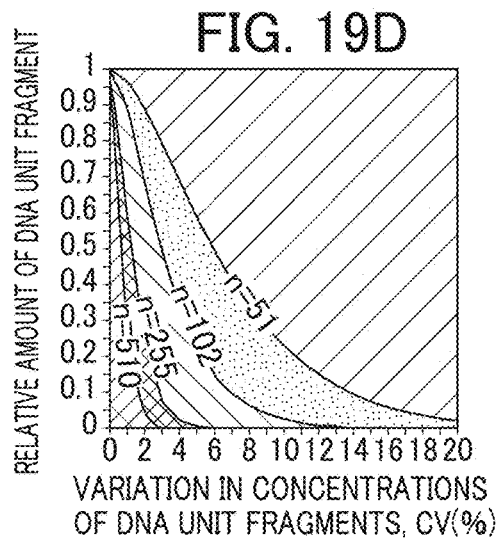

US 10,655,133 B2

METHOD FOR PREPARING DNA UNIT COMPOSITION, AND METHOD FOR CREATING CONCATENATED DNA

This is the U.S. national stage of application No. PCT/JP2014/073579 filed on Sep. 5, 2014. Priority under 35 U.S.C. § 119(a) and 35 U.S.C. § 365(b) is claimed from Japanese Application No. 2014-008690, filed Jan. 21, 2014, the disclosure of which is also incorporated herein by reference.

TECHNICAL FIELD

The present invention relates to a method of preparing a DNA unit fragment composition and a method of constructing a DNA concatemer.

BACKGROUND ART

In recent years, techniques for DNA synthesis have been increasingly developed, for example, in order to construct a long chain DNA molecule having a size of a genome. Known such techniques include assembly of chemically synthesized DNA fragments and PCR-amplified DNA unit fragments. The synthesis process of the chemical synthesized DNA and the PCR method, however, are known to be accompanied by random mutation introduced into synthesized DNA molecules. Therefore, the sequences of the DNA molecules need to be always checked somewhere from the start to the end of the gene-assembling process so as to select a DNA molecule having a desired sequence.

Checking base sequences is usually conducted by Sanger base sequencing on an automated fluorescence sequencer. This method can determine about 800 consecutive bases in a single session of base sequencing. When the number of base sequencing sessions for checking base sequences of chemically- or PCR-synthesized DNA unit fragments prior to gene-assembling is reduced, time and cost can be saved. For this reason, the chemically- or PCR-synthesized DNA unit fragments to be used for gene-assembling are preferably short.

As the DNA unit fragments to be used for gene-assembling become shorter, however, the number of them to be assembled needs to be increased.

A currently known method to assemble a plurality of DNA unit fragments is a gene-assembling method employing a plasmid transformation system in *Bacillus subtilis* (the OGAB method). Patent Document 1, for example, discloses a method that adopts the OGAB method for constructing a DNA plasmid for use in transforming a *Bacillus subtilis* cell.

The OGAB method employs a so-called multimeric plasmid, in which multiple plasmid units exist within one molecule by homologous recombination between plasmid molecules. In the OGAB method, the DNA plasmid molecule for transformation is not necessarily circular, but it only has to have a tandem-repeat structure in which a plasmid unit and a DNA unit fragment used for assembling to be assembled appear repeatedly with each unit maintaining a same direction.

In the OGAB method, to prepare a DNA molecule having a tandem-repeat structure as above described, multiple DNA unit fragments, when used, need to be joined to their corresponding plasmids. As the number of kinds of DNA unit fragments increases, it becomes more difficult to join them to their corresponding plasmids and to construct a tandem-repeat structure. To join many DNA unit fragments together, the molar ratio among DNA unit fragments in ligation is desirably made close to 1.

Patent Document 1: Japanese Patent No. 4479199

DISCLOSURE OF THE INVENTION

Problems to be Solved by the Invention

In reality, however, it is difficult to precisely control the number of moles of each kind of DNA unit fragment. One of the reasons for this is that no method that quantifies DNA with a fluorescent double-stranded DNA intercalater such as SYBR Geen I has reproducibility better than about ±20% because, for example, the color of a fluorescent substance fades during measurement. These measurement method measures the weight of DNA per unit volume and therefore when followed by the OGAB method in which the number of moles of DNA per unit volume is required for calculating the amount of each DNA unit fragment, the weight of DNA measured by the above mentioned measurement method needs to be converted to the corresponding molarity. The weight of a DNA unit fragment is proportional to the length thereof. Therefore, when the DNA unit fragment molecules are broadly varied in length and accordingly have their weight measurements varying by several folds or greater for the equal number of moles, calculation based on the measurement value often includes large errors. The method of Patent Document 1 attempts to adjust the molar ratio among DNA unit fragments to 1, but fails to precisely control the molar ratio due to the broad distribution of the lengths of the DNA unit fragments.

The present invention is devised based on the above circumstances, and an object of the present invention is to provide a method of preparing a DNA unit fragment composition and a method of constructing a DNA concatemer, in either of which methods the numbers of moles of multiple kinds of DNA unit fragments are substantially the same.

Means for Solving the Problems

The inventors of the present invention have found that measurement errors occurring in the measurement of the number of moles of each kind of DNA unit fragment are reduced when a corresponding auxiliary sequence is attached to each DNA unit fragment, and the present invention has now been completed. More specifically, the present invention subsumes the following embodiments.

(1) A method of preparing a DNA unit fragment composition, comprising:
  a step of preparing solutions containing multiple kinds of DNA unit fragments, each solution containing one of the multiple kinds of DNA unit fragments, each DNA unit fragment being attached to a corresponding auxiliary sequence; and a step of, after preparing each solution, measuring the concentration of each kind of DNA unit fragment with the corresponding auxiliary sequence attached thereto in each of the solutions, and then based on the measurement result, taking a portion from each of the solutions so that the number of moles of DNA unit fragment in one portion is close to the number of moles of DNA unit fragment in another portion.

(2) The method of preparing a DNA unit fragment composition according to (1), wherein each DNA unit fragment with the corresponding auxiliary sequence attached thereto has a circular structure, and each corresponding auxiliary sequence is a plasmid DNA sequence harboring an origin of replication.

(3) The method of preparing a DNA unit fragment composition according to (1) or (2), wherein the distribution of the sum of the lengths of the base sequence of each DNA unit fragment and the base sequence of the corresponding auxiliary sequence attached to the DNA unit fragment has a standard deviation ranging from −20% to 20% with relative to the average value of the sum of the lengths.

(4) The method of preparing a DNA unit fragment composition according to any one of (1) to (3), wherein the average length of the base sequence of the corresponding auxiliary sequence attached to each DNA unit fragment is twice or greater than the average length of the base sequence of the DNA unit fragment.

(5) The method of preparing a DNA unit fragment composition according to any one of (1) to (4), wherein each DNA unit fragment is not longer than 1600 bp.

(6) The method of preparing a DNA unit fragment composition according to any one of (1) to (5), wherein the DNA unit fragments are used to construct a DNA concatemer, the DNA concatemer comprising DNA assemblies each comprising the DNA unit fragments, and
the step of preparing solutions containing multiple kinds of DNA unit fragments comprises a step of designing each DNA unit fragment, the designing being conducted in a way that the base sequence of each DNA assembly when divided by the number of kinds of its constituent DNA unit fragments into equal parts has a non-palindromic sequence near each boundary between two adjacent equal parts, and that each DNA unit fragment has such a non-palindromic sequence at an end and is separated by the non-palindromic sequence from an adjacent DNA unit fragment.

(7) A method of constructing a DNA concatemer to be used for microbial cell transformation, the DNA concatemer comprising more than one DNA assembly unit, each of the more than one DNA assembly unit comprising a DNA vector harboring an origin of replication effective in a host microorganism and a DNA assembly, the method comprising:
a step of preparing a DNA unit fragment composition in a solution by the method as claimed in any one of (1) to (6);
a step of preparing the DNA vector;
a step of removing with a restriction enzyme a corresponding auxiliary sequence from each DNA unit fragment with the corresponding auxiliary sequence attached thereto contained in the solution after preparation; and
a step of, after the removal step, joining the DNA vector and each of the DNA unit fragment together,
wherein each of the DNA vector and the DNA unit fragment is structurally capable of being joined repeatedly while maintaining a certain order, and
each DNA assembly comprises of a DNA molecule in which the DNA unit fragment is joined to one another.

(8) The method of constructing a DNA concatemer according to (7), further comprising: a step of, based on a relation between the yield of a DNA fragment comprising a target number of DNA unit fragments joined together and a coefficient of variation for the concentration of this DNA fragment, the yield being equal to the product of the number of DNA unit fragments per assembly unit and the number of the assembly unit, adjusting a coefficient of variation for the concentrations of the DNA vector and each DNA unit fragment in the joining step.

(9) The method of constructing a DNA concatemer according to (7) or (8), wherein the restriction enzyme is a Type II restriction enzyme.

(10) The method of constructing a DNA concatemer according to any one of (7) to (9), further comprising: a step of, before the removal step, mixing two or more solutions containing DNA unit fragments selected from the solutions containing DNA unit fragments.

(11) The method of constructing a DNA concatemer according to any one of (7) to (10), further comprising: a step of, after the removal step and before the joining step, inactivating the restriction enzyme.

(12) The method of constructing a DNA concatemer according to any one of (7) to (11), wherein the microorganism is *Bacillus subtilis*.

Effects of the Invention

The present invention provides a method of preparing a DNA unit fragment composition and a method of constructing a DNA concatemer, in either of which methods the numbers of moles of multiple kinds of DNA unit fragments are substantially the same.

BRIEF DESCRIPTION OF THE DRAWINGS

FIG. 2 an illustration showing the structure of a synonymous codon variant of Fragment No. 10 among DNA unit fragments of Example 1 of the present invention.

FIG. 15 a photograph showing the result of electrophoresis in Example 2 of the present invention, conducted after transforming *Bacillus subtilis* with a DNA concatemer obtained by ligation of a DNA unit fragment and a DNA vector, extracting plasmids from the resulting plurality of transformant strains of *Bacillus subtilis*, and subjecting the resulting plasmids to restriction enzyme treatment.

FIG. 18 a graph showing the appearance number of transformants obtained by transformation of *Bacillus subtilis* competent cells with the DNA (A) to the DNA (H) used in Test Example 1.

FIG. 19 a graph showing the relationship between CV (%) indicating variation in the concentrations of DNA unit fragments and the relative amount of each kind of DNA unit fragment, analyzed for each gene assembly size in simulation 1. FIG. 19A is a graph for a 6-fragment assembly, FIG. 19B is a graph for a 13-fragment assembly, FIG. 19C is a graph for a 26-fragment assembly, and FIG. 19D is a graph for a 51-fragment assembly.

FIG. 21 FIG. 21A is a graph showing λ function of CV (%) indicating variation in the concentrations of DNA unit fragments obtained from fitting to an exponential distribution curve in simulation 1.

FIG. 24 a graph comparing actual ligation efficiency and ligation efficiency in ligation simulation in simulation 1.

PREFERRED MODE FOR CARRYING OUT THE INVENTION

Figure 1:
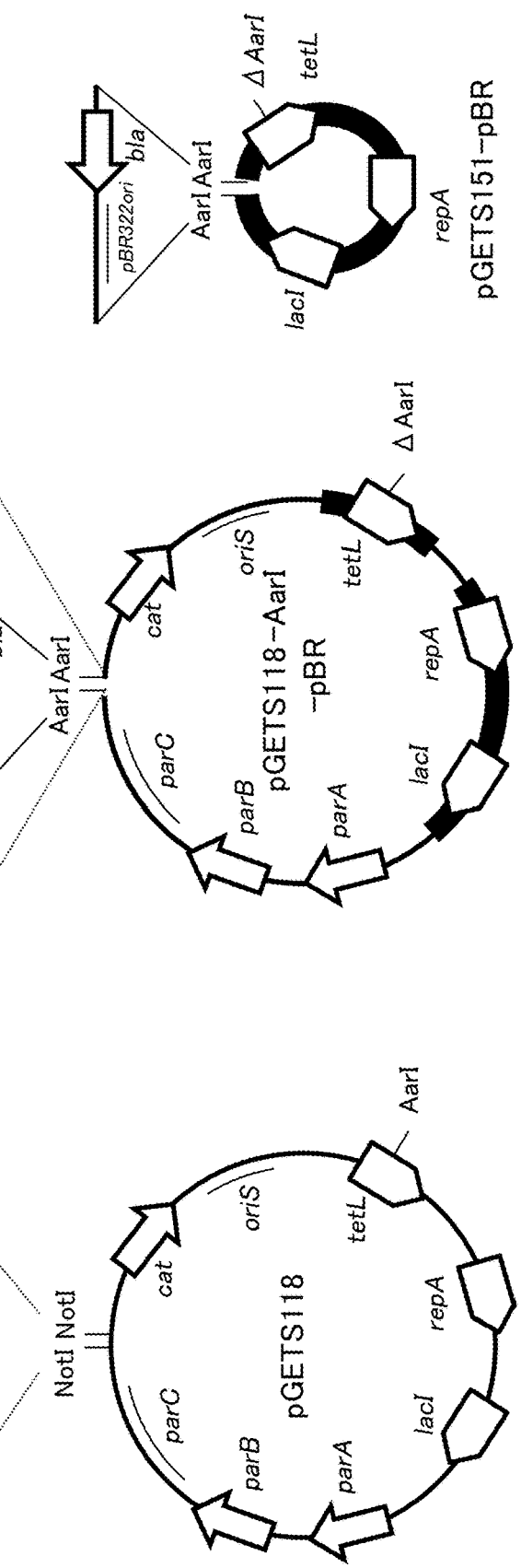
FIG. 1 an illustration showing DNA vectors according to an embodiment of the present invention.

Embodiments of the present invention are described below. The scope of the present invention, however, is not limited to these embodiments.

<Method of Preparing DNA Unit Fragment Composition>

A method of preparing a DNA unit fragment composition of the present invention comprises: a step of preparing solutions containing multiple kinds of DNA unit fragments, each solution containing one of the multiple kinds of DNA unit fragments, each DNA unit fragment being attached to a corresponding auxiliary sequence; and a step of, after the preparation step, measuring the concentration of each kind of DNA unit fragment with the corresponding auxiliary sequence attached thereto in each of the solutions, and then based on the measurement result, taking a portion from each of the solutions so that the number of moles of DNA unit fragment in one portion is close to the number of moles of DNA unit fragment in another portion. In the present specification, different kinds of "DNA unit fragments" are distinguished from each other by the difference in the base sequences. The "DNA unit fragment" refers to one with or without a restriction enzyme recognition site introduced thereinto.

In the present invention, when the concentration of each kind of DNA unit fragment in the solution containing the DNA unit fragment is measured, the DNA unit fragment being measured has the corresponding auxiliary sequence attached thereto. The corresponding auxiliary sequences thus attached contribute to reduction in distribution of the lengths of different base sequences when the concentration of the solution is measured. As a result, when the measurement result is used to calculate the number of moles of each kind of DNA unit fragment, errors in the calculation are reduced. Then, when the resulting measurement result is used for taking a portion from each of the solutions so that the number of moles of DNA unit fragment in each portion is substantially the same, the molar ratio among different portions tends to be close to 1. The "concentration of the DNA unit fragment in the solution" thus measured refers to the molarity of the DNA unit fragment. The method of measuring the molarity of the DNA unit fragment in the solution is not particularly limited, but examples of the method include measuring the mass ratio (% by mass) of the DNA unit fragment in the solution and then using the measurement (% by mass) to calculate the molarity of the DNA unit fragment in the solution. In the method of measuring the molarity of the DNA unit fragment in the solution, a means capable of measuring the DNA concentration by weight with ±20% precision is preferably used, and, more specifically, a microspectrophotometer for measuring ultraviolet absorption spectra is preferably used.

The step of preparing solutions containing DNA unit fragments each with the corresponding auxiliary sequence attached thereto is not particularly limited and may be conducted, for example, by preparing each DNA unit fragment and then attaching the corresponding auxiliary sequence to the DNA unit fragment.

Preparation of the DNA unit fragment may be conducted by using the DNA unit fragment synthesized in advance or newly constructed. Construction of each DNA unit fragment can be achieved by a well-known conventional method including polymerase chain reaction (PCR) and chemical synthesis. Addition of a restriction enzyme recognition sequence to each DNA unit fragment can be achieved by constructing the DNA unit fragment by PCR in which, for example, a primer having a restriction enzyme recognition sequence for forming a protruding end in the base sequence of the template DNA is used, or by constructing the DNA unit fragment by chemical synthesis in which a restriction enzyme recognition sequence is incorporated in advance for forming a certain protruding sequence at an end of the DNA unit fragment. The base sequence of the DNA unit fragment thus constructed can be confirmed by a well-known conventional method, for example, by incorporating the DNA unit fragment into a plasmid and then conducting Sanger base sequencing on an automated fluorescence sequencer.

The corresponding auxiliary sequence is not particularly limited and may be a linear DNA molecule or a circular plasmid. When a circular plasmid DNA sequence is used, the DNA unit fragment with the corresponding auxiliary sequence attached thereto has a circular structure and therefore can be used, for example, to transform a host such as *Escherichia coli*.

The DNA plasmid is not particularly limited in its kind, but for replication of the DNA plasmid in the transformed host, the plasmid DNA sequence preferably has an origin of replication. Specifically, a high-copy *Escherichia coli* plasmid vector, pUC19, or a derivative plasmid thereof is preferable. In order to reduce the distribution of the lengths between DNA unit fragments each attached to the corresponding auxiliary sequence so that the numbers of moles of the DNA unit fragments can be made close to one another, all the DNA unit fragments are preferably cloned into the same kind of plasmid vector.

Attaching the corresponding auxiliary sequence to each DNA unit fragment may be conducted, for example, by ligation with DNA ligase, or by TA cloning in the case of attaching the DNA unit fragment to the DNA plasmid.

The standard deviation of the distribution of the sum of the lengths of the base sequence of each DNA unit fragment and the base sequence of the corresponding auxiliary sequence attached to the DNA unit fragment is not particularly limited. When the standard deviation is small, calculation errors are reduced in the calculation of the number of moles of each DNA unit fragment conducted based on the measurement result of the DNA concentration in the solution, and, as a result, the number of moles of the DNA unit fragment contained in one solution can be close to the number of moles of DNA unit fragment in another solution. Specifically, the standard deviation of the distribution of the sum of the lengths of the base sequence of each DNA unit fragment and the base sequence of the corresponding auxiliary sequence attached to the DNA unit fragment preferably ranges from −20% to 20%, more preferably ranges from −15% to 15%, further more preferably ranges from −10% to 10%, further preferably ranges from −5% to 5%, even further preferably ranges from −1% to 1%, and most preferably ranges from −0.5% to 0.5% with relative to the average value of the sum of the lengths.

The average length of the base sequence of the corresponding auxiliary sequence attached to each DNA unit fragment is not particularly limited. When the average length of the base sequence of the corresponding auxiliary sequence attached to each DNA unit fragment is greater than the average length of the base sequence of the DNA unit fragment, calculation errors are reduced in the calculation of the number of moles of the DNA unit fragment conducted based on the measurement result of the DNA concentration in the solution, and, as a result, the number of moles of the DNA unit fragment contained in one solution can be close to the number of moles of DNA unit fragment in another solution. Specifically, the average length of the base sequence of the corresponding auxiliary sequence attached to the DNA unit fragment is preferably not smaller than twice, further preferably not smaller than 5 times, further preferably not smaller than 10 times, and most preferably not smaller than 20 times the average length of the base sequence of the DNA unit fragment. When the average length of the base sequence of the corresponding auxiliary sequence attached to each DNA unit fragment is too great, handling of the DNA unit fragment with the corresponding auxiliary sequence attached thereto is difficult. Therefore, the average length of the base sequence of the corresponding auxiliary sequence attached to each DNA unit fragment is preferably not greater than 10000 times (specifically, for example, not greater than 5000 times, not greater than 3000 times, not greater than 1000 times, not greater than 500 times, not greater than 250 times, and not greater than 100 times) the average length of the base sequence of the DNA unit fragment, for example.

The length of each DNA unit fragment is not particularly limited. However, the number of sessions of base sequencing required for determining the base sequence of each DNA unit fragment is preferably small in order to save time and cost. Therefore, each DNA unit fragment is preferably short, and specifically, it is preferably not longer than 1600 by and further preferably not longer than 1200 bp. Particularly when base sequencing is conducted by Sanger base sequencing on an automated fluorescence sequencer, which can determine about 800 consecutive bases in a single session of base sequencing, each DNA unit fragment is most preferably not longer than 800 by (specifically, not longer than 600 bp, not longer than 500 bp, not longer than 400 bp, not longer than 200 bp, and not longer than 100 bp, for example). As the DNA unit fragments thus become shorter, however, the number of them needed for constructing a DNA concatemer described below increases. Here, many DNA unit fragments can be joined together when they are prepared by the method of the present invention as described below. But, again, when each DNA unit fragment is too short, the number of the DNA unit fragments to be joined increases and, as a result, operation efficiency decreases. For this reason, each DNA unit fragment is preferably not shorter than 20 bp, more preferably not shorter than 30 bp, and further preferably not shorter than 50 bp.

Applications of the DNA unit fragment composition prepared by the method of the present invention are not particularly limited. The DNA unit fragment composition prepared by the method of the present invention can be used to construct a DNA concatemer comprising DNA assemblies each comprising the DNA unit fragments. When the DNA unit fragment composition prepared by the method of the present invention is used to construct a DNA concatemer by a method described below, many kinds of DNA unit fragments (50 kinds or more, for example) can be joined together. This is achieved probably for a reason that the numbers of moles of DNA unit fragments contained in the DNA unit fragment composition prepared by the method of the present invention are close to one another with high precision.

In the present invention, the step of preparing solutions containing DNA unit fragments may comprise a step of designing each DNA unit fragment. Designing each DNA unit fragment is not particularly limited. In the case, for example, where the DNA unit fragment composition is used to construct a DNA concatemer comprising DNA assemblies, the designing may be conducted in a way that the base sequence of each DNA assembly when divided by the number of kinds of its constituent DNA unit fragments into equal parts has a non-palindromic sequence near each boundary between two adjacent equal parts, and that each DNA unit fragment is separated by the non-palindromic sequence from an adjacent DNA unit fragment. The DNA unit fragments thus designed have substantially the same length. This characteristic is preferable in terms of operation efficiency because when the DNA unit fragments are to be used for DNA concatemer construction as described below and are therefore subjected to removal of corresponding auxiliary sequences with restriction enzymes and to subsequent electrophoresis for size-based selection, the DNA unit fragments are observed substantially as a single band, allowing recovery of all the DNA unit fragments to be completed in a single session of size-based selection. The area referred to by the expression "near each boundary between two adjacent equal parts" is not particularly limited, and may be determined, as needed, based on the length of the base sequence. When the base sequence of each DNA unit fragment is 1000-bp long, for example, the area "near each boundary between two adjacent equal parts" may be determined, for example, as an area within 100 by (specifically, within 90 bp, within 80 bp, within 70 bp, within 60 bp, within 50 bp, within 30 bp, within 20 bp, within 10 bp, within 5 bp) of each "boundary between two adjacent equal parts".

When the DNA unit fragment is thus designed for constructing a DNA concatemer comprising target DNA assemblies, the DNA unit fragment is preferably designed to have a non-palindromic sequence (a sequence that is not a palindromic sequence) at an end of the DNA unit fragment. The non-palindromic sequence of the DNA unit fragment thus designed is converted into a protruding sequence that is structurally capable of being joined repeatedly while maintaining a certain order as described below.

<Method of Constructing DNA Concatemer>

The present invention also subsumes a method of constructing a DNA concatemer. The method of constructing a DNA concatemer of the present invention comprises: a step of preparing the DNA unit fragment composition in the solution by the method described above; a step of preparing a DNA vector; a step of removing with a restriction enzyme the corresponding auxiliary sequence from each DNA unit fragment with the corresponding auxiliary sequence attached thereto contained in the solution; and a step of, after the removal step, joining the DNA vector and the DNA unit fragment together.

The DNA concatemer comprises more than one DNA assembly unit and is to be used for microbial cell transformation. Each DNA assembly unit comprises the DNA vector and the DNA assembly. The number of DNA assembly units in one DNA concatemer is not particularly limited provided that it is greater than 1. However, for enhanced efficiency in transformation, the number is preferably not smaller than 1.5, more preferably not smaller than 2, further preferably not smaller than 3, and most preferably not smaller than 4.

Each DNA vector harbors an origin of replication effective in a host microorganism that is to be transformed. The DNA vector is not particularly limited provided that it harbors a sequence that allows DNA replication to occur in a microorganism to be transformed with the DNA concatemer. For example, the DNA vector harbors a sequence coding for an origin of replication effective in a bacterium of the genus Bacillus (*Bacillus subtilis*). The sequence coding for an origin of replication effective in *Bacillus subtilis* is not particularly limited. Examples of sequences coding for the origin of replication include sequences coding for, for example, an origin of replication harbored by plasmids such as pTB19 (Imanaka, T., et al. J. Gen. Microbioi. 130, 1399-1408. (1984)), pLS32 (Tanaka, T and Ogra, M. FEBS Lett. 422, 243-246. (1998)), and pAMβ1 (Swinfield, T. J., et al. Gene 87, 79-90. (1990)).

Each DNA assembly is a DNA molecule in which the DNA unit fragment described above is joined to one another. The DNA referred to in the present invention is a DNA molecule to be cloned, and is not particularly limited in its kind or size. Specifically, the DNA referred to in the present invention may have a sequence naturally occurring in a prokaryote, a eukaryote, a virus, or the like or an artificial sequence, for example. In the method of the present invention capable of joining many DNA unit fragments to a plasmid as described above, a DNA molecule having a long base sequence is preferably used. The DNA molecule having a long base sequence is, for example, a group of genes coding for an entire metabolic pathway or a complete or partial genomic DNA of a phage or the like.

Each DNA assembly unit may or may not comprise an additional proper base sequence, where appropriate, besides the DNA vector and the DNA assembly. In the case of constructing a plasmid for use in expression of a constituent gene of the DNA assembly, the DNA assembly unit may comprise a base sequence capable of controlling transcription and translation, such as a promoter, an operator, an activator, and a terminator. Specific examples of a promoter for *Bacillus subtilis* as a host include Pspac promoter (Yansura, D. and Henner, D. J. Pro. Natl. Acad. Sci, USA 81, 439-443. (1984.)), the expression of which can be controlled by IPTG (isopropyl s-D-thiogalactopyranoside), and Pr promoter (Itaya, M. Biosci. Biotechnol. Biochem. 63, 602-604. (1999)).

Each of the DNA vector and the DNA unit fragment is structurally capable of being joined repeatedly while maintaining a certain order. In the present specification, the expression "joined while maintaining a certain order" refers to that a DNA unit fragment is joined in a certain order and orientation to another DNA unit fragment or to a DNA vector adjacent within a DNA assembly unit. The expression "joined repeatedly" refers to that the 5' end of a DNA unit fragment or a DNA vector harboring its 5' base sequence is joined to the 3' end of a DNA unit fragment or a DNA vector harboring its 3' base sequence. Specific examples of such a DNA unit fragment include a DNA unit fragment having an end capable of being joined repeatedly to a partner while maintaining a certain order due to complementation between the base sequences of their protruding ends. Such protrusion is not particularly limited in its structure, or in the difference in shape between one on the 5' protruding end and one on the 3' protruding end, provided that it has a non-palindromic sequence.

Each protruding end is preferably formed by the step of removing the corresponding auxiliary sequence from the DNA unit fragment with a restriction enzyme. Therefore, in construction of a DNA concatemer by the method of the present invention, the DNA unit fragment preferably comprises a restriction enzyme recognition sequence that allows removal of the corresponding auxiliary sequence with a restriction enzyme. The preparation of the DNA vector can also be conducted, for example, by restriction enzyme treatment that forms a protruding end and allows the DNA vector and the DNA unit fragment to join repeatedly while maintaining a certain order.

The restriction enzyme used above for removal of the corresponding auxiliary sequence is not particularly limited, but is preferably a Type II restriction enzyme, and is more preferably a Type IIS restriction enzyme that can form a protruding end having a certain sequence at a locus at a certain distance outside its recognition sequence, such as AarI, BbsI, BbvI, BcoDI, BfuAI, BsaI, BsaXI, BsmAI, BsmBI, BsmFI, BspMI, BspQI, BtgZI, FokI, and SfaNI. A Type IIS restriction enzyme can form different protruding ends for a single DNA unit fragment, and consequently can maintain the order in which DNA unit fragments are joined. Not only in the preparation of the DNA unit fragment but also in the preparation of the DNA vector, a Type IIS restriction enzyme is preferably used for forming a protruding end that allows the DNA vector and the DNA unit fragment to join repeatedly while maintaining a certain order.

The DNA unit fragments can be divided into groups, each group for a single restriction enzyme to be used for removal of the corresponding auxiliary sequence. In this case, each group can consist of two or more solutions each containing a different DNA unit fragment. The two or more solutions can be mixed together before the removal step. As a result, a separate session of restriction enzyme treatment is not required for respective DNA unit fragment, but, instead, a single session of restriction enzyme treatment is enough to treat an entire restriction-enzyme group. Especially when the DNA unit fragments are fractionated by electrophoresis, the DNA unit fragments can be recovered in a single session of fractionation and, as a result, operation efficiency is further enhanced. However, when there are multiple groups of the DNA unit fragments, fractionation is conducted for each group. When the DNA unit fragments are recovered, the recovered amounts can vary between different groups. Accordingly, the numbers of moles of DNA unit fragments that have been made substantially the same can also vary. For this reason, the number of groups each for a single restriction enzyme to be used for removal of the corresponding auxiliary sequence is preferably small, in other words, the number of kinds of restriction enzymes to be used for removal of the corresponding auxiliary sequence is preferably small. The number of kinds of restriction enzymes to be used is preferably not greater than 5, more preferably not greater than 3, and most preferably 1. Specifically, when only a single kind of restriction enzyme is used, all the solutions containing DNA unit fragments can be mixed together, leading to significant enhancement in operation efficiency and then to decreased probability of variation occurring in the number of moles of DNA unit fragments that have been made substantially the same. The number of moles of many DNA unit fragments are made substantially the same when mixed together, and therefore these many DNA unit fragments can be joined together as described above with a restriction enzyme.

When a Type IIS restriction enzyme recognition sequence is added to the sequence of the DNA unit fragment, the Type IIS restriction enzyme to be used is selected so that it recognizes none of the sequences of the DNA unit fragments in the same group. In other words, when a certain Type IIS restriction enzyme is used, each restriction enzyme recognition is designed such that the Type IIS restriction enzyme does not recognizes the sequence of one DNA unit fragment but recognizes the sequence of another DNA unit fragment, a different Type IIS restriction enzyme is selected for the another DNA unit fragment. In case of such design, different Type IIS restriction enzymes are used for different DNA unit fragments, and that the DNA unit fragments can then be divided into groups each for a different Type IIS restriction enzyme. If a Type IIS restriction enzyme is available that recognizes none of the sequences of the DNA unit fragments used, the recognition sequence of the Type IIS restriction enzyme can be added to the DNA unit fragments so that the corresponding auxiliary sequences can be removed from the DNA unit fragments all at once with the single Type IIS restriction enzyme.

The step of joining the DNA vector and the DNA unit fragment is not particularly limited, but can be conducted by, after restriction enzyme treatment, fractionating the DNA unit fragment from its corresponding auxiliary sequence treated with the restriction enzyme and then joining the DNA unit fragment thus fractionated and the DNA vector with DNA ligase or the like (ligation). In this way, a DNA concatemer to be used for microbial transformation can be constructed. It is noted that the DNA unit fragment used in the joining step has no restriction enzyme recognition sequence added thereinto.

The method of fractionation between the DNA unit fragment and its corresponding auxiliary sequence is not particularly limited. It is preferable that the molar ratio between the DNA unit fragments is maintained after restriction enzyme treatment, and agarose gel electrophoresis is specifically preferable.

The method of joining the DNA unit fragment and the DNA vector is not particularly limited, but the joining is preferably conducted in the presence of polyethylene glycol and a salt. The salt is more preferably a monovalent alkali metal salt. More specifically, the joining is further preferably conducted in a ligation reaction solution containing 10% polyethylene glycol 6000 and 250-mM sodium chloride. The concentration of each DNA unit fragment in the ligation reaction solution is not particularly limited, but is preferably not lower than 1 fmol/μl. The reaction temperature and the reaction time for ligation are not particularly limited, but are preferably 37° C. and for 30 minutes or longer. Preferably, the concentration of the DNA vector in the ligation reaction solution is measured before reaction and then the number of moles of the DNA vector and the number of moles of the DNA unit fragment are adjusted to be the same.

The method of preparing a DNA concatemer according to the present invention may or may not comprise, and preferably comprise a step of, based on a relation between the yield of a DNA fragment comprising a target number of DNA unit fragments joined together and a coefficient of variation for the concentration of this DNA fragment (hereinafter in the present specification, the coefficient is called "coefficient of variation 1") (hereinafter in the present specification, the relation is called "relation"), the yield being equal to the product of the number of DNA unit fragments per assembly unit and the number of the more than one assembly unit, adjusting a coefficient of variation for the concentrations of the DNA vector and each DNA unit fragment (hereinafter in the present specification, the coefficient is called "coefficient of variation 2") in the joining step. It is noted that the coefficient of variation 1 is a coefficient of variation used in the relation for convenience, and the coefficient of variation 2 is the coefficient of variation for the concentrations of each DNA unit fragment and the DNA vector in the actual joining step. By including this adjustment step, the coefficient of variation 2 is adjusted to fall within the range shown by the relation, a desired number of DNA unit fragments (for example, 50 DNA unit fragments) can be joined in the joining step.

The target number of DNA unit fragments joined together refers to the number of DNA fragments intended to be joined in the joining step, and more specifically refers to the product of the number of DNA unit fragments per assembly unit to be joined and the number of the more than one assembly unit. The "yield of a DNA fragment comprising a target number of DNA unit fragments joined together" refers to the proportion of the number of DNA fragments per DNA assembly unit joined together to the total number of DNA fragments used for joining.

The relation according to the present invention is a formula showing the relationship between the yield of a DNA fragment comprising a target number of DNA unit fragments joined together and the coefficient of variation 1. A formula determined by computer simulation of ligation, for example, can be used. More specifically, the relation can be obtained by conducting simulation of ligation, for example, for each of DNA unit fragment groups having a coefficient of variation 1 varying by 1% starting from 0% to 20% (10 to 30 groups, for example), determining the distribution of the number of DNA unit fragments per each resulting DNA concatemer (exponential distribution, for example), plotting a fitting curve of the resulting distributions, and using the fitting curve. A specific tool for use in ligation simulation is not particularly limited and a conventional known means can be used. For example, VBA (Visual Basic for Applications) of spreadsheet software Excel (registered trademark) 2007 can be used for programming as well as constructing algorithms to conduct simulation. The fitting curve can be plotted, for example, with a function of spreadsheet software Excel (registered trademark) 2007 that helps plotting exponential approximation curves. Adjustment of the coefficient of variation 2 based on the relation can be conducted, for example, after designing the relation, by substituting the yield of a target DNA fragment into the relation thus obtained, and adjusting the process in each pre-joining step so that the DNA fragment being joined has a coefficient of variation 1 equal to the thus-calculated coefficient of variation 1. The method of adjustment is not particularly limited. For example, the adjustment may be conducted by selecting, in a step such as the step of preparing the DNA vector, the step of preparing the DNA unit fragment, and/or the step of joining the DNA vector and the DNA unit fragment together, a measuring instrument (a spectrophotometer, a spectrofluorophotometer, or a real-time PCR apparatus, for example), that has its measurement errors known in advance for use in determining the concentration of the DNA vector or the DNA unit fragment in order to obtain the desired coefficient of variation 2.

The coefficient of variation 2 is not particularly limited. As the variation in the concentrations of the DNA unit fragments being joined is reduced, the number of DNA unit fragments that can be joined increases. Therefore, the coefficient of variation 2 is preferably not greater than 20%, more preferably not greater than 15%, further preferably not greater than 10%, further more preferably not greater than 8%, and most preferably not greater than 5%.

The method of preparing a DNA concatemer of the present invention may further comprise a step of inactivating the restriction enzyme after the removal step and before the joining step. A certain DNA unit fragment can have a restriction enzyme cleavage site that is the same as a restriction enzyme cleavage site for separating another DNA unit fragment from its corresponding auxiliary sequence. In this case, it is difficult to mix together different DNA unit fragment groups with their corresponding auxiliary sequences attached thereto while the restriction enzyme or enzymes are still active. Accordingly, the DNA unit fragments cannot be fractionated in a single session by combining these DNA unit fragment groups together. In contrast, when the restriction enzyme or enzymes have been inactivated, different DNA unit fragment groups with their corresponding auxiliary sequences attached thereto can be combined together after the inactivation, and, as a result, the DNA unit fragments can be fractionated in a single session. This advantage makes it easier to construct a DNA concatemer comprising even a greater number of DNA assemblies in the joining step, and, as a result, makes it easier to transform *Bacillus subtilis*. Inactivation of the restriction enzymes can be conducted by a well-known conventional method, for example, phenol-chloroform treatment.

The host microorganism to be transformed is not particularly limited provided that it has ability to undergo spontaneous transformation. Examples of the ability to undergo spontaneous transformation include ability to process DNA into a single strand prior to taking it up. Specific examples of the host microorganism include bacteria of the genus *Bacillus*, bacteria of the genus *Streptococcus*, bacteria of the genus *Haemophilus*, abacteria of the genus *Neisseria*, and the like. Examples of the bacteria of the genus *Bacillus* include *B. subtilis* (*Bacillus subtilis*), *B. megaterium* (*Bacil-* lus megaterium), *B. stearothermophilus* (*Bacillus stearothermophilus*), and the like. Examples of the most preferable microorganisms, among these, include *Bacillus subtilis* that has excellent ability to undergo spontaneous transformation and recombination.

The DNA concatemer constructed by the method of the present invention can be used for microbial cell transformation. The method of giving competency to a microorganism that is to be transformed can be a known method that is suitable for the selected microorganism. Specifically, for *Bacillus subtilis*, a method described in Anagnostopoulou, C. and Spizizen, J. J. Bacteriol., 81, 741-746(1961) is preferably used. Similarly, as the method of transformation, a known method that is suitable for the selected microorganism can be used. The amount of ligation product solution to give to the competent cell is not particularly limited, but is preferably from 1/20 to 20/20 and more preferably half the amount of the competent cell culture. The method of purifying the resulting plasmid from the transformant can also be a known method.

The presence of DNA assemblies in the plasmid purified from the transformant can be confirmed by checking the size-based patterns of fragments cleaved by a restriction enzyme or enzymes, PCR, or base sequencing. When the DNA insert for a substance-producing function, it can be confirmed by detecting the function.

EXAMPLES

The present invention will be described below more specifically by examples. The examples merely illustrate embodiments of the present invention, and therefore do not limit the scope of the present invention.
(Materials)

The microbial cells used for transformation were *Bacillus subtilis* cells. The strains of *Bacillus subtilis* used were strain RM125 (Uozumi, T., et al. Moi. Gen. Genet., 152, 65-69 (1977)) and its derivative strain BUSY9797. As a DNA vector capable of replication in *Bacillus subtilis*, pGETS118-AarI-pBR (see SEQ ID NO:1) constructed as described below by using pGET118 (Kaneko, S., et al. Nucleic Acids Res. 31, e112 (2003)) as well as pGETS151-pBR (see SEQ ID NO:2) were used. As a DNA assembly, lambda phage DNA (manufactured by Toyobo Co., Ltd.) (see SEQ ID NO:3) and an artificial operon of the mevalonate pathway described below (see SEQ ID NO:4) were used. For selecting an *Escherichia coli* having a DNA plasmid into which a DNA unit fragment is incorporated, the antibiotic carbenicillin (Wako Pure Chemical Industries, Ltd.) was used. For selecting *Bacillus subtilis*, the antibiotic tetracycline (Sigma) was used. As a Type IIS restriction enzyme, AarI (Thermo), BbsI (NEB), BsmBI (NEB), and SfiI (NEB) were used. The restriction enzymes HindIII, PvuII, and T4 DNA Ligase used were manufactured by Takara Bio Inc. For ligation that was normally conducted for constructing an *Escherichia coli* plasmid, Takara Ligation Kit (Mighty) (Takara Bio Inc.) was used. For PCR reaction for preparing a DNA unit fragment, KOD plus polymerase manufactured by Toyobo Co., Ltd. was used. For colony PCR for base sequencing DNA cloned in a plasmid, Ex-Taq HS manufactured by Takara Bio Inc. was used. As a DNA plasmid that was a corresponding auxiliary sequence to be attached to a DNA unit fragment, pMD-19 (simple) (Takara Bio Inc.) was used. The enzyme used for purifying a circular plasmid was Plasmid Safe manufactured by EPICENTRE. As the agarose gel for electrophoresis, 2-Hydroxyethyl agarose (Sigma), which was agarose gel for DNA electrophoresis having low melting temperature, or UltraPure Agarose (Invitrogen Limited) was used. For inactivation of a restriction enzyme, phenol:chloroform:isoamyl alcohol 25:24:1 and TE saturated phenol (containing 8-quinolinol) manufactured by Nacalai Tesque, Inc. were used. The lambda terminase used was manufactured by EPICENTRE. For lambda phage packaging, Gigapack III Plus Packaging Extract from Agilent Technologies was used. The lysozyme used was manufactured by Wako Pure Chemical Industries, Ltd. The medium component of the LB medium and the agar-agar manufactured by Becton, Dickinson and Company were used. The IPTG (isopropyl s-D-thiogalactopyranoside) used was manufactured by Wako Pure Chemical Industries, Ltd. All the medium components and biochemical reagents other than those described above manufactured by Wako Pure Chemical Industries, Ltd were used. For construction of a plasmid other than those particularly mentioned, one of *Escherichia coli* strains DH5a, JM109, and TOP10 was used. For purification of a small amount of constructed plasmid from *Escherichia coli*, QIAprep Spin Miniprep Kit from QIAGEN was used, while for purification of a large amount, QIAfilter Midi Kit from QIAGEN was used. For DNA cleanup from an enzymatic reaction solution, MinElute Reaction Cleanup Kit from QIAGEN or QIAquick PCR purification Kit from QIAGEN was used. For purification of a gel block resulting from ordinary agarose gel electrophoresis separation, MinElute Gel Extraction Kit from QIAGEN was used. As a spectrophotometer for trace amount detection, nano-drop 2000 from Thermo was used. For base sequencing, the automated fluorescence sequencer 3130×1 Genetic Analyzer manufactured by Applied Biosystems Inc. was used. Other common DNA handling was conducted according to a standard protocol (Sambrook, J., et al., Molecular Cloning: A Laboratory Manual. Cold Spring Harbor Laboratory Press, Cold Spring Harbor, N.Y. (1989)). *Bacillus subtilis* transformation and plasmid extraction were conducted according to a known method (Tsuge, K., et al., Nucleic Acids Res. 31, e133. (2003)).
(Construction of DNA Vector used in Assembly)

The DNA vector used in lambda phage DNA assembly, pGETS118-AarI-pBR (SEQ ID NO:1), was a plasmid constructed through multiple steps starting from the *Escherichia coli*-*Bacillus subtilis* shuttle plasmid vector pGETS118 harboring an origin of replication in *Escherichia coli* F factor, oriS, and an origin of replication in *Bacillus subtilis*, repA (Kaneko, et. al., Nucleic Acids Res., 31,e112. (2003)). The structure thereof is shown in FIG. 1. The cloning site for a gene assembly was the area between two AarI cleavage sites. This area between the two AarI cleavage sites, which was to be removed at the time of assembling, had an origin of replication of the *Escherichia coli* multicopy plasmid pBR322 for facilitating vector acquisition in *Escherichia coli*, as well as an ampicillin resistance gene, introduced thereinto. As for the AarI cleavage site naturally occurring in a tetracycline resistance gene of pGETS118, its recognition site was rendered ineffective by single base mutation that had no influence on the amino acid sequence of the tetracycline resistance gene (tetL). The DNA vector used in assembly of an artificial mevalonate-pathway operon, pGETS151-pBR (SEQ ID NO:2), was constructed by joining together fragments amplified from the pGETS118-AarI-pBR DNA described above as a template with three pairs of primers, PartA (5'-TAGGGTCTCAaagcggccgcaagctt-3' (see SEQ ID NO:5) and 5'-TAGGGTCTCAGCggccaagaaggcc-3' (see SEQ ID NO:6)), PartB (5'-TAGGGTCTCAccGCCCT-TCCCGGTCGATAT-3' (see SEQ ID NO:7) and 5'-TAGGGTCTCAtaTTAGCTTAATTGTTATCCGCTCA- CAATTCC-3' (see SEQ ID NO:8)), and PartC (5'-TAGGGTCTCAAAtaactggaaaaaattagtgtctcatggttcg-3' (see SEQ ID NO:9) and 5'-TAGGGTCTCAgcttaagtggtgggtagtt-gacc-3' (see SEQ ID NO:10)). Unlike the template plasmid, this DNA vector pGETS151-pBR did not have gene regions functioning only in *Escherichia coli* (the region between cat and oriS, and the region between parA and parC) (FIG. 1). Although this DNA vector with a gene assembly was capable of replicating only in *Bacillus subtilis*, it shared the same characteristics with pGETS118-AarI-pBR in terms of the gene-assembling process. To about 10 µl of a solution each containing one of the plasmids (equivalent to 5 µg), 29 µl of sterilized water, 5 µl of 10× Buffer_for_AarI that came with a restriction enzyme used, 1 µl of 50× Oligonucleotide for activation of cleavage that also came with the restriction enzyme used, and 5 µl of the restriction enzyme AarI (Thermo) were added, followed by reaction at 37° C. for 2 hours. The resulting liquid was subjected to separation by electrophoresis in agarose gel having low melting temperature. From the gel, a fragment of about 15 kb (in the case of pGETS118-AarI-pBR) or of 4.3 kb (in the case of pGETS151-pBR) attributed to the vector was cut out, followed by purification of the DNA vector in question, which was then dissolved in 20 µl of TE. The concentration of the DNA vector was measured by taking a 1-µl sample from the TE solution and subjecting the sample to measurement with a spectrophotometer for trace amount detection.

(Designing DNA Unit Fragment's Border Regions)

The number of different combinations of 4-base protruding was 4 raised to the 4th power, which was equal to 256. From these, protruding sequences used in the present invention were selected according to the following criterion. First, all the 16 palindromic sequences (Group 0) (AATT, ATAT, TATA, TTAA, CCGG, CGCG, GCGC, GGCC, ACGT, AGCT, TCGA, TGCA, CATG, CTAG, GATC, GTAC) were excluded because their complementary sequences had the same sequences as their own and therefore there was a possibility that identical fragments would join together, which was not appropriate in the present invention. The remaining 240 sequences included both a certain sequence (CCTA, for example) and its complementary sequence (TAGG), and therefore the theoretical number of combinations of protruding sequences applicable to DNA concatenation was 240/2=120 combinations. Then, based on the GC content and the appearance order in which the constituent G and C bases were aligned, these combinations were divided into groups of combinations of protruding ends as follows.

(Group I) 6 combinations of protruding ends consisting of A and T alone (AAAA/TTTT, TAAA/TTTA, ATAA/TTAT, AATA/TATT, AAAT/ATTT, ATTA/TAAT).

(Group II) All 32 combinations consisting of 3 bases selected from A and T and 1 base selected from C and G (CAAA/TTTG, ACAA/TTGT, AACA/TGTT, AAAC/GTTT, GAAA/TTTC, AGAA/TTCT, AAGA/TCTT, AAAG/CTTT, CAAT/ATTG, ACAT/ATGT, AACT/AGTT, AATC/GATT, GAAT/ATTC, AGAT/ATCT, AAGT/ACTT, AATG/CATT, CATA/TATG, ACTA/TAGT, ATCA/TGAT, ATAC/GTAT, GATA/TATC, AGTA/TACT, ATGA/TCAT, ATAG/CTAT, CTTA/TAAG, TCTA/TAGA, TTCA/TGAA, TTAC/GTAA, GTTA/TAAC, TGTA/TACA, TTGA/TCAA, TTAG/CTAA).

(Group III) 44 combinations, left by subtracting 8 palindromic combinations from all 52 combinations consisting of 2 bases selected from A and T and 2 bases selected from C and G (AACC/GGTT, AACG/CGTT, AAGC/GCTT, AAGG/CCTT, ACAC/GTGT, ACAG/CTGT, ACCA/TGGT, ACCT/AGGT, ACGA/TCGT, ACTC/GAGT, ACTG/CAGT, AGAC/GTCT, AGAG/CTCT, AGCA/TGCT, AGGA/TCCT, AGTC/GACT, AGTG/CACT, ATCC/GGAT, ATCG/CGAT, ATGC/GCAT, ATGG/CCAT, CAAC/GTTG, CAAG/CTTG, CACA/TGTG, CAGA/TCTG, CATC/GATG, CCAA/TTGG, CCTA/TAGG, CGAA/TTCG, CGTA/TACG, CTAC/GTAG, CTCA/TGAG, CTGA/TCAG, CTTC/GAAG, GAAC/GTTC, GACA/TGTC, GAGA/TCTC, GCAA/TTGC, GCTA/TAGC, GGAA/TTCC, GGTA/TACC, GTCA/TGAC, GTGA/TCAC, TCCA/TGGA).

(Group IV) 16 combinations with no 3 consecutive bases selected from C and G, out of all 32 combinations consisting of 1 base selected from A and T and 3 bases selected from C and G (CACC/GGTG, CCAC/GTGG, CTCC/GGAG, CCTC/GAGG, CACG/CGTG, CCAG/CTGG, CTCG/CGAG, CCTG/CAGG, CAGC/GCTG, CGAC/GTCG, CTGC/GCAG, CGTC/GACG, GAGC/GCTC, GGAC/GTCC, GTGC/GCAC, GGTC/GACC).

(Group V) All 16 combinations with 3 consecutive bases selected from C and G, out of all 32 combinations consisting of 1 base selected from A and T and 3 bases selected from C and G (ACCC/GGGT, CCCA/TGGG, TCCC/GGGA, CCCT/AGGG, ACCG/CGGT, CCGA/TCGG, TCCG/CGGA, CCGT/ACGG, ACGC/GCGT, CGCA/TGCG, TCGC/GCGA, CGCT/AGCG, AGGC/GCCT, GGCA/TGCC, TGGC/GCCA, GGCT/AGCC).

(Group VI) All 6 combinations consisting of bases selected from C and G alone (CCCC/GGGG, GCCC/GGGC, CGCC/GGCG, CCGC/GCGG, CCCG/CGGG, CGGC/GCCG).

Boundaries between a DNA vector and a DNA unit fragment in Examples 1 and 2 were selected from Group 1 among the groups divided as above. Boundaries between two DNA unit fragments as candidates were selected from 60 combinations in total of protruding ends included in Group III (44 combinations) and Group IV (16 combinations). Selection of a combination of protruding ends was conducted by determining the full-length final base sequence made up by the sequences to be assembled and then determining ideal dividing boundaries that divided the full-length base sequence into equal parts. The base sequence used in Example 1 is described below referring to specific examples.

Example 1 is an experiment of reconstruction of a 48522-bp molecule consisting of the 48502-bp full-length lambda phage genome, to which a 16-bp cos site and a 4-bp protruding sequence required for assembly are added. Table 1 below shows ideal dividing boundaries and actual dividing boundaries within DNA assemblies and protruding base sequences of the DNA assemblies in Example 1. Reconstruction was attempted by first dividing the molecule devoid of a plasmid vector for assembly into 50 DNA unit fragments having substantially the same size, and then joining these 50 DNA unit fragments together. Ideally, all of the 50 fragments are divided to have the same length. In order to avoid changing any base in the sequences to be assembled, it was necessary to construct 5' end protruding of 4 bases to be used for assembly, depending on the originally existing sequence. In reality, there was almost no chance that each single one of the ideal dividing boundaries had one of the protruding sequences described above, which means that it was impossible to divide the original sequence into equal DNA unit fragments at the ideal dividing boundaries. Therefore, in this example, in order to make the size of the unit as close to the size of the ideal dividing unit as possible, simulation was conducted to assign a protruding-end combination to each boundary. The simulation was conducted as follows: first, the full-length original molecule (48522 bp) was divided into 50 equal-sized ideal DNA unit fragments of 970 bp, which were then named as Fragment No. 01, Fragment No. 02, Fragment No. 03, . . . , and Fragment No. 50 in order of increasing absolute base number; and, then, the presence of any 4-base protruding end candidate was searched for within a 4-base sequence that extended the same distance from an absolute position of each ideal boundary (the ideal dividing boundaries lay between the 970th base and the 971th base, between the 1940th base and the 1941th base, between the 2910th base and the 2911th base, . . . , and between the 47530th base and the 47531th base), with the 4-base sequence being sequentially enlarged by 1 base at a time to each side of the ideal dividing boundary, namely, the 4-base sequence becoming sequentially enlarged to a 6-base sequence, an 8-base sequence, a 10-base sequence, a 12-base sequence, a 14-base sequence, a 16-base sequence, an 18-base sequence, a 20-base sequence, a 22-base sequence, and a 24-base sequence. This procedure is explained in the following specific example (Table 1). The ideal dividing boundary between Fragment No. 01 and Fragment No. 02 lay between the 970th base and the 971th base. Within the 16-base sequence extending the same distance from the ideal dividing boundary (the base sequence from the 963th base to the 988th base, namely, 5'-ATGCTGCTGGGTGTTT-3'), 7 protruding-end combination candidates were found (ACAC/GTGT, AGCA/TGCT, ATGC/GCAT, CACC/GGTG, CAGC/GCTG, CCAG/CTGG, CTGC/GCAG). This procedure was conducted for all the 49 ideal dividing boundaries, in an attempt to find at least one protruding sequence candidate within each base sequence of a certain length lying near each of the ideal dividing boundaries. When the length was extended to 24 bp, each base sequence had at least one 4-base protruding sequence candidate. Then, for each base sequence, a specific protruding sequence was selected from the protruding candidates, as follows: the least common protruding-end combination found (or not taken yet) in all of the (remaining) base sequences was assigned, preferentially, to the base sequence with the least number of protruding-end combination candidates; and this procedure was repeated so that a unique protruding-end combination was assigned to all the boundaries.

TABLE 1

| Ideal dividing boundary | 60 Bases near ideal dividing boundary ("\|" indicates each ideal dividing boundary) | Actual dividing | Protruding sequence | Complementary sequence |
|---|---|---|---|---|
| −1\|1 | tgagacgtctcggcctgtttggcc<u>atta</u>CG\|GGGCGGCGACCTCGCGGGTTTTCGCTATTT | −7/−6 | ATTA | TAAT |
| 970\|971 | TGCCCGTGTCGGTTATTCCAAA<u>ATG</u>CTGCT\|GGGTGTTTATGCCTACTTTATAGACCATAA | 962/963 | ATGC | GCAT |
| 1940\|1941 | GACTCCCAGCTGGACCGCTACGAAATGCGC\|GT<u>ATGG</u>GGATGGGGGCCGGGTGAGGAAAGC | 1942/1943 | ATGG | CCAT |
| 2910\|2911 | ACATCGCTGCGCGAATATGCCGGTTATCAC\|GGCGGTGGCAGCGGATTTGGAGGGCAGTTG | 2907/2908 | CACG | CGTG |
| 3880\|3881 | TGAACCTGCAGACGGCTCAGGATACGGAT<u>A</u>\|<u>ACG</u>GCTACTCCGTGTTTGAGCAGTCACTGC | 3879/3880 | AACG | CGTT |
| 4850\|4851 | GGATGGTGGCGGGGGCATTTGACTGCGCTG\|ACATCATCGCCCGTGTGCGTGACATAAAAC | 4847/4848 | CTGA | TCAG |
| 5820\|5821 | CAGTGACCCGGCTCATACCGCAACCGCGCC\|CGGC<u>GGAT</u>TGAGTGCGAAAGCGCCTGCAAT | 5824/5825 | GGAT | ATCC |
| 6790\|6791 | TTCCTTCAAAGCCGTCAAGGAGAAGCTGGA\|<u>TACC</u>CGTCGTGGCTCTAATTCCGAGCTGGA | 6790/6791 | TACC | GGTA |
| 7760\|7761 | TGGTGTTTTTGATGACCCTGAAAATATCA<u>G</u>\|<u>CTA</u>TGCCGGACAGGGCGTGCGCGTTGAAGG | 7759/7760 | GCTA | TAGC |
| 8730\|8731 | CGAAGAGCTGGACAGCGATACCTGGCAGGC\|<u>G</u>GAGCTGCATATCGAAGTTTTCCTGCCTGC | 8731/8732 | GAGC | GCTC |
| 9700\|9701 | AGAAATTACCGTCACCGCCAGTTAATCCGG\|<u>AGAG</u>TCAGCGATGTTCCTGAAAACCGAATC | 9700/9701 | AGAG | CTCT |
| 10670\|10671 | GAAAGTGATGCGAAAAAAACAGCGGC<u>AGTC</u>\|GTTGAACAGTCGCTGAGCCGACAGGCGCTG | 10666/10667 | AGTC | GACT |
| 11640\|11641 | GGGATGATCGTGAAAAGGCCCGTCTTGCGC\|TT<u>GAAG</u>CCGCCCGAAAGAAGGCTGAGCAGC | 11642/11643 | GAAG | CTTC |
| 12610\|12611 | CACCCGTTCCGTGCTGTCCATGATGA<u>CAGA</u>\|AATTCTGCTTAAGCAGGCAATGGTGGGAT | 12606/12607 | CAGA | TCTG |
| 13580\|13581 | GCAGAACGAAAAGGTGAGCCGGTCACCTG\|GCAGGGGCGACAGTATCAGCCGTATCCCAT | 13577/13578 | CTGG | CCAG |
| 14550\|14551 | TCTGGCGGGGATTGAGATGCCGGACTTTGA\|<u>TCGT</u>GAGGATGACTGGTGGCGTAACGGCCA | 14550/14551 | TCGT | ACGA |
| 15520\|15521 | ATGGAGCGTGAGGAATGGGTAAAGGA<u>AGCA</u>\|GTAAGGGGCATACCCCGCGCGAAGCGAAGG | 15516/15517 | AGCA | TGCT |
| 16490\|16491 | GGAGCCGCGCATCACCTGTAATGCGT<u>ACCT</u>\|GACCACACAGCGTAAGGCGTGGGATGTGCT | 16487/16488 | CCTG | CAGG |
| 17460\|17461 | ACACCGAAGGTGGTGAAGGGCGT<u>GAG</u>TTTC\|CTGCTGCGTCTGACCGTAACAGCGGACGAC | 17452/17453 | TGAG | CTCA |
| 18430\|18431 | TGAATGCGAACTCCGGGACGCTCAGTAA<u>TG</u>\|<u>TG</u>ACGATAGCTGAAAACTGTACGATAAACG | 18428/18429 | TGTG | CACA |
| 19400\|19401 | TGGATTACCGTAAGACGGAAATCA<u>CTCC</u>CG\|GGTATATGAAAGAGACGACCACTGCCAGGG | 19394/19395 | CTCC | GGAG |
| 20370\|20371 | AGGCCGCCACTTCAGCACGAGATGCG<u>GTGG</u>\|CCTCAAAAGAGGCAGCAAAATCATCAGAAA | 20366/20367 | GTGG | CCAC |
| 21340\|21341 | TTTGACAAATCAGCCTACCCAAAACTTGCT\|<u>GTCG</u>CGTATCCATCGGGTGTGCTTCCTGAT | 21340/21341 | GTCG | CGAC |
| 22310\|22311 | AGGGGAATATCAGAAGTGGAACG<u>GCAC</u>AGC\|CTGGGTGAAGGATACGGAAGCAGAAAAACT | 22303/22304 | GCAC | GTGC |

TABLE 1-continued

| Ideal dividing boundary | 60 Bases near ideal dividing boundary ("\|" indicates each ideal dividing boundary | Actual dividing | Pro-truding sequence | Comple-mentary sequence |
|---|---|---|---|---|
| 23280\|23281 | AATGACAATTTGCTTATGGAGTAATCTTTT\|AATTTTAAATAAGTTATTCTCCTGGCTTCA | 23268/23269 | GAGT | ACTC |
| 24250\|24251 | GGGTGTTGAATGATTTCCAGTTG<u>CTAC</u>CGA\|TTTTACATATTTTTTGCATGAGAGAATTTG | 24243/24244 | CTAC | GTAG |
| 25220\|25221 | ACTACTAAGGTTGTAGGCTCAAGAGGGTGT\|<u>GTCC</u>TGTCGTAGGTAAATAACTGACCTGTC | 25220/25221 | GTCC | GGAC |
| 26190\|26191 | TCCAATATAAAAGTATTGTGTACCTTTTGC\|T<u>GGGT</u>CAGGTTGTTCTTTAGGAGGAGTAAA | 26192/26193 | GGTC | GACC |
| 27160\|27161 | TCTGCTTCCTTTTGGATAACCC<u>ACTG</u>TTAT\|TCATGTTGCATGGTGCACTGTTTATACCAA | 27152/27153 | ACTG | CAGT |
| 28130\|28131 | TTATCAAGTGTTTCCTTCATTGATATTC<u>CG</u>\|<u>AG</u>AGCATCAATATGCAATGCTGTTGGGATG | 28128/28129 | CGAG | CTCG |
| 29100\|29101 | AAGTACATCGCAAAGTCTCCGCAATTACAC\|GCAAGAAAAAACCGCCATCAGGCGGCTTGG | 29096/29097 | ACAC | GTGT |
| 30070\|30071 | CAGGATGGCGAACAACAAGAAACTGGTTTC\|C<u>GTCTT</u>CACGGACTTCGTTGCTTTCCAGTT | 30071/30072 | GTCT | AGAC |
| 31040\|31041 | CTGGTTTCTCTCATCTGCTTCTGCTTTCGC\|C<u>ACCA</u>TCATTTCCAGCTTTTGTGAAAGGGA | 31041/31042 | ACCA | TGGT |
| 32010\|32011 | AGCTCTCACATCGATCCCGGTACGCTGC<u>AG</u>\|<u>GA</u>TAATGTCCGGTGTCATGCTGCCACCTTC | 32008/32009 | AGGA | TCCT |
| 32980\|32981 | GCGTTGCAAATGATCGATGCATAGCGATTC\|AAAC<u>AGGT</u>GCTGGGGCAGGCCTTTTTCCAT | 32984/32985 | AGGT | ACCT |
| 33950\|33951 | AGATAAAAAATCGCCCTCACAC<u>TGGA</u>GGGC\|AAAGAAGATTTCCAATAATCAGAACAAGTC | 33942/33943 | TGGA | TCCA |
| 34920\|34921 | TTGAGCTTGGTGTGTTGAACAAAACTTT<u>TT</u>\|<u>CC</u>CGATGGAATGGAAAGCATATATTATTCC | 34918/34919 | TTCC | GGAA |
| 35890\|35891 | AACAAGGATGCATATATGAATGAACGATGC\|AGAGG<u>CAA</u>TGCCGATGGCGATAGTGGGTAT | 35894/35895 | GCAA | TTGC |
| 36860\|36861 | AACAAAAAGATGGGAATCCCAATGATT<u>CG</u>\|<u>TC</u>ATCTGCGAGGCTGTTCTTAATATCTTCA | 36858/36859 | CGTC | GACG |
| 37830\|37831 | CCTGACTGCCCCATCCCCATCT<u>TGTC</u>TGCG\|ACAGATTCCTGGGATAAGCCAAGTTCATTT | 37822/37823 | TGTC | GACA |
| 38800\|38801 | ACGCCAGACTATCAAATATGCTGCTTGAGG\|CTTA<u>TTCG</u>GGCGCAGATCTGACCAAGCGAC | 38804/38805 | TTCG | CGAA |
| 39770\|39771 | AGCCTGGCTAACCGTGACCA<u>GAAC</u>GAAGTG\|AACGAAATCCGTCGCCAGTGGGTTCTGGCT | 39760/39761 | GAAC | GTTC |
| 40740\|40741 | AAATCCTTCCAGACCCAACCAAACCAAT<u>CG</u>\|<u>TA</u>GTAACCATTCAGGAACGCAACCGCAGCT | 40738/40739 | CGTA | TACG |
| 41710\|41711 | GCCTGCAAAGATGAGGAGGGATTGC<u>AGC</u>GT\|GTTTTTAATGAGGTCATCACGGGATCCCAT | 41704/41705 | CAGC | GCTG |
| 42680\|42681 | TTAAAGCCCCGCAGTTACTGGATTAAACAA\|GC<u>CCAA</u>CAAGCCGTAAACGCCTTCATCAGA | 42682/42683 | CCAA | TTGG |
| 43650\|43651 | AAAAATATGTTATCTGCCACGCCGATTATC\|C<u>CCTTT</u>GACGAATACGAGTTTGGAAAGCCAG | 43650/43651 | CCTT | AAGG |
| 44620\|44621 | ATGGGTTAATTCGCTCGTTGTGGTAGTGAG\|AT<u>GAAAA</u>GAGGCGGCGCTTACTACCGATTC | 44614/44615 | AGTG | CACT |
| 45590\|45591 | CGGACGTCAGAAAACGAGAAATCATGGTTA\|TGACGTCATTGTAGGCGGAGAGCTATTTAC | 45590/45591 | TGAC | GTCA |
| 46560\|46561 | TACGAATGTTTGCTGGGTTTCTGTTTTAA<u>C</u>\|<u>AAC</u>ATTTTCTGCGCCGCCACAAATTTTGGC | 46559/46560 | CAAC | GTTG |
| 47530\|47531 | TTTTATCGTTTCAATCTGGTCTGACCTC<u>CT</u>\|<u>TG</u>TGTTTTGTTGATGATTTATGTCAAATAT | 47528/47529 | CTTG | CAAG |
| 48500\|48501 | ACGGGTCCTTTCGGGTGATCCGACAGGTTA\|CGGGGCGGCGACCTCGaaaaggccttcttg | 48516/48517 | AAAA | TTTT |

Example 1, Construction of Lambda Phage Point Mutant with Assembly Comprising 50 DNA Unit Fragments and DNA Vector <Lambda Phage>

A lambda phage is a bacteriophage that infects *Escherichia coli*, and is studied in the molecular biology field the most widely among other phages. Its genome is 48502-bp double-stranded DNA at its full-length, and the entire base sequence has been identified. It has various variants, many of which have been identified. In this example, construction of a lambda phage point mutant from a short DNA unit fragment of about 1 kb was attempted.

<Division Design of Lambda Phage Genome>

As a lambda phage, λ phage DNA manufactured by Toyobo Co., Ltd. was used. This product had a linear cos site. The full-length genome sequence of the phage was sequenced (SEQ ID NO:3), revealing 6 differences (g.138delG, g.14266_14267insG, g.37589C>T, g.37743C>T, g.43082G>A, g.45352 G>A) from a base sequence registered in the database (Accession No. J02459.1) (the full-length sequence shown under SEQ ID NO:3 had a size of 48526 bp, consisting of 48522 by as described above and 4 bases of the other protruding end). In order to divide this 48522-bp full-length base sequence (including duplicated cos sites) into parts having substantially the same length, ideal dividing boundaries were designated every 970 bp, followed by the procedure described above in (Designing DNA unit fragment's dividing regions). As a result, a unique 5' protruding end that was a 4-base sequence to the right of a corresponding cleavage site was successfully assigned to each DNA unit fragment group, as shown in Table 1.

<Selection of Kind of Restriction Enzyme for Forming Protruding End>

Examples of a Type IIS restriction enzyme for forming an arbitrary 4-base protruding sequence include AarI (5'-CACCTGC(N)4/-3',5'-/(N)8 GCAGGTG-3'), BbsI (5'-GAAGAC(N)2/-3',5'-/(N)6 GTCTTC-3'), BbvI (5'-GCAGC(N)8/-3',5'-/(N)12 GCTGC-3'), BcoDI (5'-GTCTCN/-3',5'-/(N)5 GAGAC-3'), BfuAI (5'-ACCTGC(N)4/-3',5'-/(N)8 GCAGGT-3'), BsaI (5'-GGTCTCN/-3',5'-/(N)5 GAGACC-3'), BsmAI (a BcoDI isoschizomer), BsmBI (5'-CGTCTCN/-3', 5'-/(N)5 GAGACG-3'), BsmFI (5'-GGGAC(N)10/-3',5'-/(N)14 GTCCC-3'), BspMI (a BfuAI isoschizomer), BtgZI (5'-GCGATG(N)10/-3',5'-/(N)14CATCGC-3'), FokI (5'-GGATG(N)9/-3'5'-/(N)13CATCC-5'), and SfaNI (5'-GCATC(N)9/-3',5'-/(N)13 GATGC-5'). These restriction enzymes were screened for any restriction enzyme that did not have its recognition site in an *Escherichia coli* plasmid vector used for gene fragment subcloning (pMD19, Simple, TAKARA), or any restriction enzyme that had its recognition site in there but was capable of forming a fragment longer enough or shorter enough than the ideal dividing unit. As a result, a total of 6 kinds of restriction enzyme candidates were found, including 5 restriction enzymes (AarI, BbsI, BfuAI, BsmFI, and BtgZI) that did not had no cleavage and 1 restriction enzyme (BsmBI) that had its recognition sequence in the vector but was capable of forming a fragment longer enough or shorter enough than the ideal dividing unit. As for these restriction enzyme site candidates, the distribution of the restriction enzyme site within the entire lambda phage, namely, across Fragment No. 01 to Fragment No. 50 was searched. As a result, each of these restriction enzymes had its restriction enzyme recognition sites within the lambda phage genome, namely, 12 sites for AarI, 24 sites for BbsI, 41 sites for BfuAI, 38 sites for BsmFI, 45 sites for BtgZI, and 14 sites for BsmBI. Then, for each DNA unit fragment, a restriction enzyme that did not cleave inside the DNA unit fragment itself was used. It was confirmed that it is sufficient that the fewest number of the kinds of restriction enzymes to be used was only 3, namely, BbsI, AarI, and BsmBI. Each of these Type IIS restriction enzymes was assigned for cleaving a certain group of DNA unit fragments, as follows.

The group of fragments to be cleaved with BbsI consisted of Fragments Nos. 01 to 08, 12, 16 to 22, 24, 27, 28, 33 to 39, 43, and 45 to 50, a total of 33 fragments; the group to be cleaved with AarI consisted of Fragments Nos. 09 to 11, 13, 23, 25.30, 32, and 44, a total of 9 fragments; and the group to be cleaved with BsmBI consisted of Fragments Nos. 14, 15, 26, 29, 31, and 40 to 42, a total of 8 fragments.

<Cloning of Gene Fragment>

All of the 50 fragments, from Fragment No. 01 to Fragment No. 50, were amplified from the full-length lambda phage genome by PCR. First, to the 5' end of a primer for amplifying a DNA sequence between combinations of protruding-end sequences determined above, a corresponding restriction enzyme recognition site among those determined above was attached so that a protruding end was to be formed at the intended position. Then, to the resulting 5' end, a primer to which a TAG sequence was further attached was used. A pair of these primers made in this way was used to amplify a certain DNA fragment in the specified region from the full-length lambda phage genome. PCR reaction was allowed to proceed under the conditions where 50 µl for one cycle consisted of 5 µl of KOD Plus 10× buffer Ver.2, 3 µl of 25-mM MgSO4, 5 µl of dNTP (2 mM each), 1 µl of KOD Plus (1 unit/µl), 48 µg of lambda phage DNA (Toyobo Co., Ltd.), 15 pmol of primers (an F primer and an R primer respectively), and sterilized water, and on a GeneAmp PCR System 9700 (Applied Biosystems Inc.) programmed as follows.

One cycle consisted of incubation at 94° C. for 2 mM, at 98° C. for 10 s, 55° C. for 30 s, and then at 68° C. for 1 min. The cycle was repeated 30 times, followed by incubation at 68° C. for 7 mM The amplified DNA unit fragments were separated in 1% agarose gel (UltraPure Agarose, Invitrogen Ltd.) made of 1×TAE buffer (prepared by diluting "Tris-acetate-EDTA stock buffer (50× concentrated) pH8.3 (at 25° C.)" manufactured by Nacalai Tesque, Inc. 50 times with milliQ water) containing 2 mg/ml of Crystal Violet (Wako Pure Chemical Industries, Ltd.), on an electrophoresis system (i-MyRun. NC, Cosmo Bio Co., Ltd.) at a voltage of 100 V for 10 mM of electrophoresis. The DNA band in question was cut out from the electrophoresis gel with a razor to recover as the gel segment weighed about 200 mg. From this gel segment, a DNA unit fragment was purified with a Concert Rapid Gel Extraction System (Life Technologies). The specific procedure was as follows: L1 Buffer having a volume 3 times the weight of the gel segment was added to the gel segment; the gel segment was dissolved at 45° C. in a block incubator for about 10 min; the resulting solution was added into a spin column cartridge supplied (a 2-ml centrifuge tube into which a spin column was attached); centrifugation was conducted at 20,000×g for 1 mM and the flow-through was discarded; 750 µl of L2 Buffer was then added to the spin column; and centrifugation was conducted at 20,000×g for 1 mM and the flow-through was discarded. In order to remove as much residue such as the L2 Buffer remaining in the spin column as possible, the following procedure was conducted: the spin column was centrifuged at 20,000×g for 1 mM; the spin column was transferred from the 2-ml centrifuge tube which was discarded to a 1.5-ml centrifuge tube; into the spin column, 30 µl of TE buffer (10 mM Tris-HCl, 1 mM EDTA, pH8.0) was added; and the spin column was left for 2 mM and was then centrifuged at 20,000×g for 1 min to recover a DNA solution. The resulting DNA was preserved at −20° C. until it was used. The resulting DNA unit fragment was cloned into the *Escherichia coli* plasmid vector by the following TA cloning method.

To 8 µl of the DNA unit fragment solution, 1 µl of 10× Ex-Taq Buffer that came with TAKARA PCR reaction enzyme Ex-Taq, 0.5 µl of 100-mM dATP, and 0.5 µl of Ex-Taq was added, followed by incubation at 65° C. at 10 min. As a result, a protrusion of A was added to the 3' end of the DNA unit fragment. To 1 µl of the DNA unit fragment solution, 1 µl of TAKARA pMD19-Simple and 3 µl of sterilized water were added and mixed, and thereto, 5 µl of TAKARA Ligation (Mighty) Mix was added, followed by incubation at 16° C. for 30 min A 5-µl portion of the ligation solution was added to 50 µl of *Escherichia coli* DH5a chemically competent cell, followed by incubation on ice for 15 min, heat shock at 42° C. for 30 sec, and then being left on ice for 2 min. Thereto, 200 µl of an LB medium was added, followed by incubation at 37° C. for 1 h. The culture was streaked onto an LB plate supplemented with carbenicillin (100 µg/ml) and containing 1.5% agar-agar, followed by overnight culture at 37° C. As a result, a transformant transformed with the plasmid was obtained. A resulting colony was treated with a PCR template DNA preparation reagent (Cica Geneus DNA preparation reagent, KANTO CHEMICAL CO., INC.), and a PCR template DNA molecule was prepared. Specifically, Reagent a and Reagent b in the reagent kit were mixed in a ratio of 1:10, and into 2.5 µl of the resulting solution, a fraction of a colony taken from the plate with a toothpick was suspended, followed by treatment at 72° C. for 6 min and then at 94° C. for 3 min. To the resulting liquid, 2.5 µl of TAKARA Ex-Taq 10× enzyme, 2 µl of 2.5-mM dNTP solution, 0.25 µl of 10-pmol/µl M13F primer, 0.25 µl of 10-pmol/µl M13R primer, 17 µl of sterilized water, and 0.5 µl of Ex-TaqHS were added, followed by incubation at 94° C. for 5 min. A cycle of incubation at 98° C. for 20 sec, at 55° C. for 30 sec, and at 72° C. for 1 min was repeated 30 times for DNA amplification. The base sequence of the PCR product was analyzed to confirm complete agreement of it with the intended sequence. Consequently, all the clones gave the correct sequences. In this process, one of the variants obtained from Fragment No. 10 was found to have synonymous substitution within its gene-V-coding region (g.9515 G>C). Due to this mutation, in the phage genome, a restriction enzyme AvaI recognition site newly appears (FIG. 2). In this example, for the purpose of clearly demonstrating that the phage was artificially constructed, this variant with synonymous substitution (g.9515 G>C) was used instead of the wild-type one, as for Fragment No. 10.

<High-Purity Purification of Plasmid Harboring DNA Unit Fragment>

Figure 3:
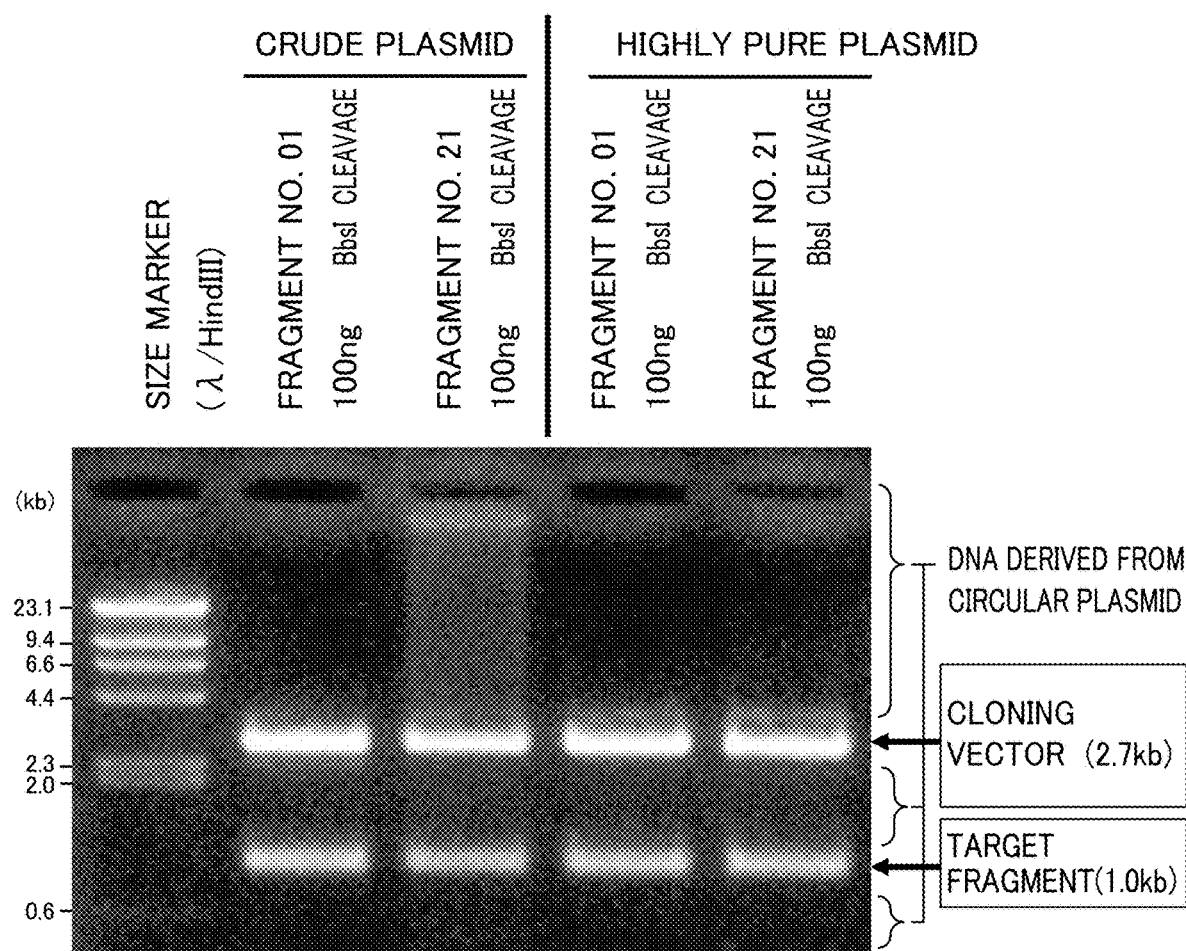
FIG. 3 a photograph showing the result of electrophoresis analyzing crude plasmids each harboring Fragment No. 01 or Fragment No. 21 among DNA unit fragments of Example 1 of the present invention, and highly pure plasmids resulting from purification of these crude plasmids, after restriction enzyme treatment.

Each of the all 50 kinds of *Escherichia coli* transformants each harboring a plasmid into which a corresponding one of Fragments Nos. 01 to 50 having the intended sequence had been cloned was cultured overnight at 37° C. for 120 spm in 50 ml of an LB medium supplemented with 100 µg/ml of carbenicillin. The resulting bacterial cells were subjected to purification with QIAfilter Plasmid Midi Kit (QIAGEN). To 50 µl of the resulting crude plasmid solution, 5 µl of a 3-M potassium acetate-acetic acid buffer solution (pH5.2) and 125 µl of ethanol were added, followed by centrifugation at 20,000×g for 10 min for ethanol precipitation of the DNA. The resulting precipitate was rinsed with 70% ethanol, and the residue was removed, followed by re-dissolution in 50 µl of TE (pH8.0). A 1-µl sample was taken from the crude plasmid solution for measurement of the DNA concentration with a spectrophotometer for trace amount detection (ND-2000, Thermo). The amount of DNA in the crude plasmid solution at this time was about 0.5 µg/µl to 4 µg/µl. Referring to the measurement value, 5 µg of DNA was taken from each crude plasmid solution and collected into a 1.5-ml tube, into which sterilized water was added so as to achieve a total volume of 50 µl. Thereto, 6 µl of Plasmid Safe (Epicentre) 10× reaction buffer, 2.4 µl of 25-mM ATP solution, and 2 µl of Plasmid Safe enzyme solution were added and mixed, followed by incubation at 37° C. for 1 h in the programmable block incubator BI-526T (ASTEC) and then incubation at 75° C. for 30 min for enzyme inactivation. The resulting solution was purified with PCR purification kit (QIAGEN). In the final step of purification with the kit, the DNA adsorbed on the column was eluted off not with the elution buffer that came with the kit but with 25 µl of TE buffer (pH8.0) so as to give a highly-pure plasmid solution. The plasmid harboring Fragment No. 01 and the plasmid harboring Fragment No. 21 before and after purification were analyzed by DNA electrophoresis (UltraPure Agarose, Invitrogen Limited), confirming incorporation of the intended fragments (DNA unit fragments) (FIG. 3).

<Precisely Adjusting Concentrations of Plasmids each Harboring DNA Unit Fragment, and Combining Equal Moles of Plasmids>

The resulting DNA solution was reanalyzed with a spectrophotometer for trace amount detection so as to determine the concentration of the highly-pure plasmid solution. The concentration of each sample was within the range from about 100 ng/µl to 200 ng/µl reflecting the degree of purification of the crude plasmid solution, where the theoretical maximum concentration was 200 ng/µl. Based on the measurement result, 15 µl of each plasmid solution was taken into a 1.5-ml tube, to which TE was added so as to achieve a concentration of each plasmid of 100 ng/µl. Reanalysis of the concentration of the resulting highly-pure plasmid solution with a spectrophotometer for trace amount detection showed variation from the target value of 100 ng/µl within the range of about several percent. As for each highly-pure plasmid solution, the volume (µl) of the solution containing 500 ng of the DNA was accurately calculated to the second decimal place. A portion of the DNA solution in an amount of this volume (about 5 µl) was combined with the other such portions that were to be cleaved later with the same kind of restriction enzyme (the BbsI group, the AarI group, and the BsmBI group). Between the portions combined together, the numbers of moles of the DNA unit fragments were adjusted to be substantially the same.

<Cleavage of Same-mole-number Plasmids Combined Together, in One Session with Restriction Enzyme>

The total volume of the combined same-mole-number plasmid solution was about 165 µl for the BbsI group, about 45 µl for the AarI group, and about 40 µl for the BsmBI group. The combined solution of each group was tripled in volume with sterilized water, giving a highly-pure plasmid solution having a volume of 495 µl, 135 µl, or 120 µl, which was cleaved with the corresponding kind of restriction enzyme as follows.

Figure 4:
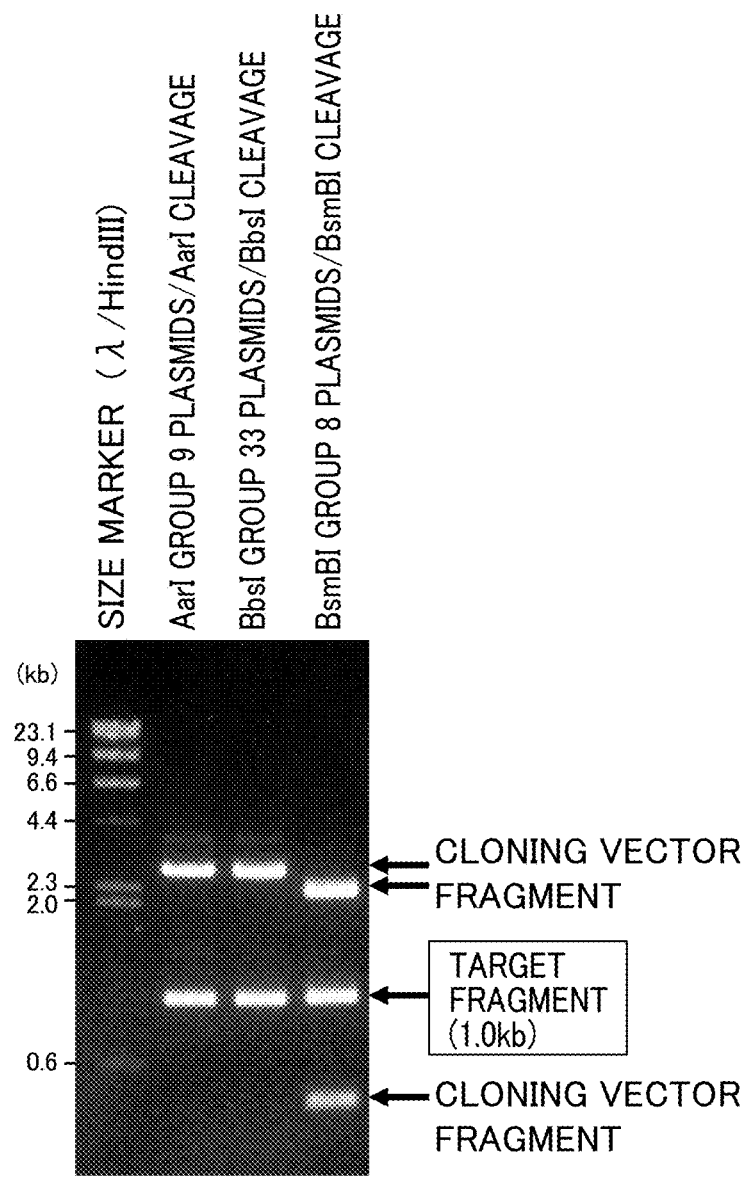
FIG. 4 a photograph showing the result of electrophoresis analyzing a group of plasmids to be treated with BbsI, a group of plasmids to be treated with AarI, and a group of plasmids to be treated with BsmBI, among plasmids harboring DNA unit fragments after purification in Example 1 of the present invention. Each group of plasmids had been treated with each restriction enzyme in one session prior to electrophoresis.

To the highly-pure plasmid solution of the BbsI group, 55 µl of 10×NEB buffer #2 and 27.5 µl of the restriction enzyme BbsI (NEB) were added to give about 577 µl of the resulting plasmid solution, which was subjected to reaction at 37° C. for 2 h. To the highly-pure plasmid solution of the AarI group, 15 µl of 10× Buffer_for_AarI that came with the restriction enzyme, 3 µl of 50× Oligonucleotide for activation of cleavage that also came with the restriction enzyme, and 7.5 µl of the restriction enzyme AarI (Thermo) were added to give about 160 µl of the resulting plasmid solution, which was subjected to reaction at 37° C. for 2 h. To the highly-pure plasmid solution of the BsmBI group, 13.3 µl of 10×NEB Buffer #3 and 6.3 µl of the restriction enzyme BsmBI (NEB) were added to give about 140 µl of the resulting plasmid solution, which was subjected to reaction at 55° C. for 2 h. After 2 h, a portion was taken from each plasmid solution without the same-mole-number relationship being lost, in other words, 33 µl from the BbsI group, 9 µl from the AarI group, and 8 µl from the BsmBI group were taken. A 5-µl sample from each portion was analyzed by DNA electrophoresis, and cleavage of the plasmids with the corresponding restriction enzyme was confirmed (FIG. 4).

<Fractionation, in One Session, of 50 DNA Unit Fragments by Agarose Gel Electrophoresis, and Purification>

Figure 5:
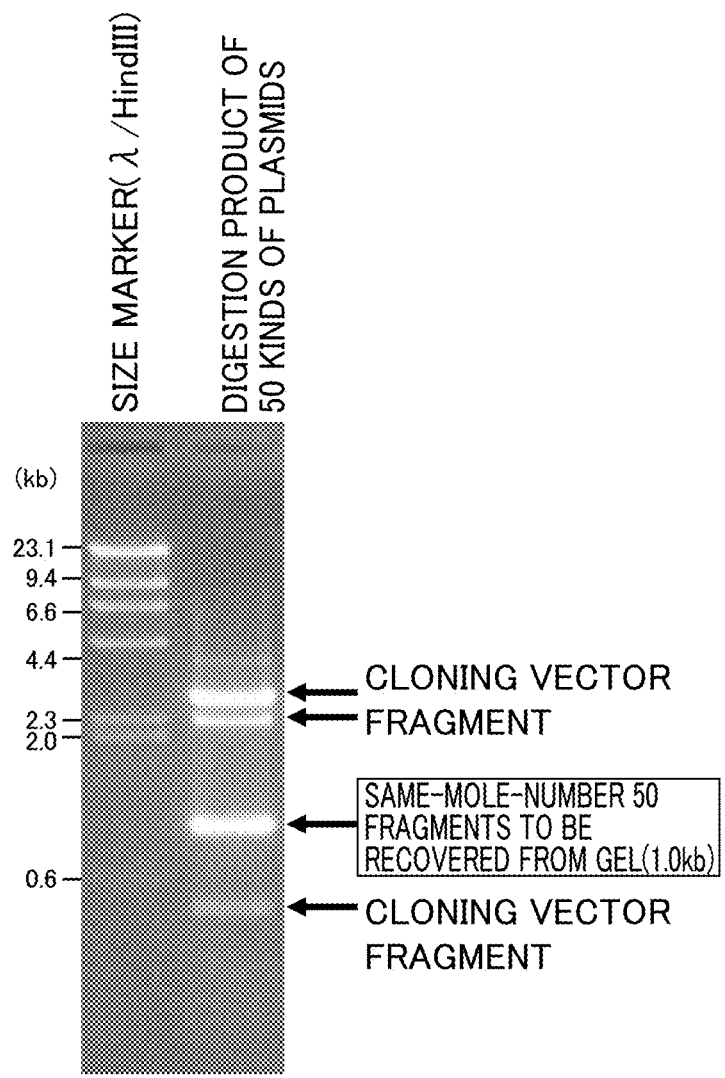
FIG. 5 a photograph showing the result of electrophoresis analyzing a group of plasmids to be treated with BbsI, a group of plasmids to be treated with AarI, and a group of plasmids to be treated with BsmBI, among plasmids harboring DNA unit fragments after purification in Example 1 of the present invention. Each group of plasmids had been treated with each restriction enzyme in one session and then combined together prior to electrophoresis.

After the confirmation above, an equal amount of phenol-chloroform-isoamyl alcohol (25:24:1) (Nacalai Tesque, Inc.) was added to and mixed well with each plasmid solution for restriction enzyme inactivation. The resulting mixture of the plasmid solution and phenol-chloroform-isoamyl alcohol (25:24:1) was combined with the other mixtures into a single tube, followed by centrifugation (20,000×g, 10 min) for separation into a phenol phase and an aqueous phase. The aqueous phase (about 900 µl) was transferred to another 1.5-ml tube, to which 500 µl of 1-butanol (Wako Pure Chemical Industries, Ltd.) was added and mixed well, and the resultant was centrifuged (20,000×g, 1 min) so as to remove water-saturated 1-butanol. This series of procedure was repeated until the aqueous phase was reduced to a volume of 450 µl or lower. To the resultant, 50 µl of a 3-M potassium acetate-acetic acid buffer (pH5.2) and 900 µl of ethanol were added, followed by centrifugation (20,000×g, 10 min) to precipitate the DNA, which was rinsed with 70% ethanol and dissolved in 20 µl of TE. To the resultant, 2 µl of 10× Dye for electrophoresis was added. The entire mixture was subjected to electrophoresis in 0.7% agarose gel with low melting temperature (2-Hydroxyethyl Agarose Type VII, Sigma) in the presence of 1×TAE (Tris-Acetate-EDTA Buffer) buffer on a commercially available agarose gel electrophoresis system (i-MyRun. N, nucleic acid electrophoresis system, Cosmo Bio Co., Ltd.) at a voltage of 35 V (about 2 V/cm) for 4 h of electrophoresis. As a result, Fragments Nos. 01 to 50 were separated from the plasmid vectors (FIG. 5). The gel after electrophoresis was stained in 100 ml of 1×TAE buffer containing 1 µg/ml of ethidium bromide (Sigma) for 30 min, followed by irradiation with ultraviolet having a long wavelength (366 mn). The band attributed to Fragments Nos. 01 to 50 (near about 1 kb) thus visualized was cut out with a razor, and was transferred into a 1.5-ml tube. To the agarose gel with low melting temperature (about 300 mg), 1×TAE buffer was added to achieve a total volume of about 700 followed by incubation at 65° C. for 10 min for gel dissolution. To the resulting gel solution, 500 µl of 1-butanol was added, and centrifugation (20,000×g, 1 min) was conducted for separation into an aqueous phase and a butanol phase, followed by discarding water-saturated butanol. This series of procedure was repeated until the aqueous phase was reduced to a volume of 450 µl or lower. To the resulting liquid, 50 µl of a 3-M potassium acetate-acetic acid buffer solution (pH 5.2) and 900 µl of ethanol were added, followed by centrifugation (20,000×g, 1 min) to precipitate the DNA, which was rinsed with 70% ethanol and dissolved in 20 µl of TE. A 1-µl sample was taken from the resultant for measurement of the concentration with a spectrophotometer for trace amount detection.

Figure 6:
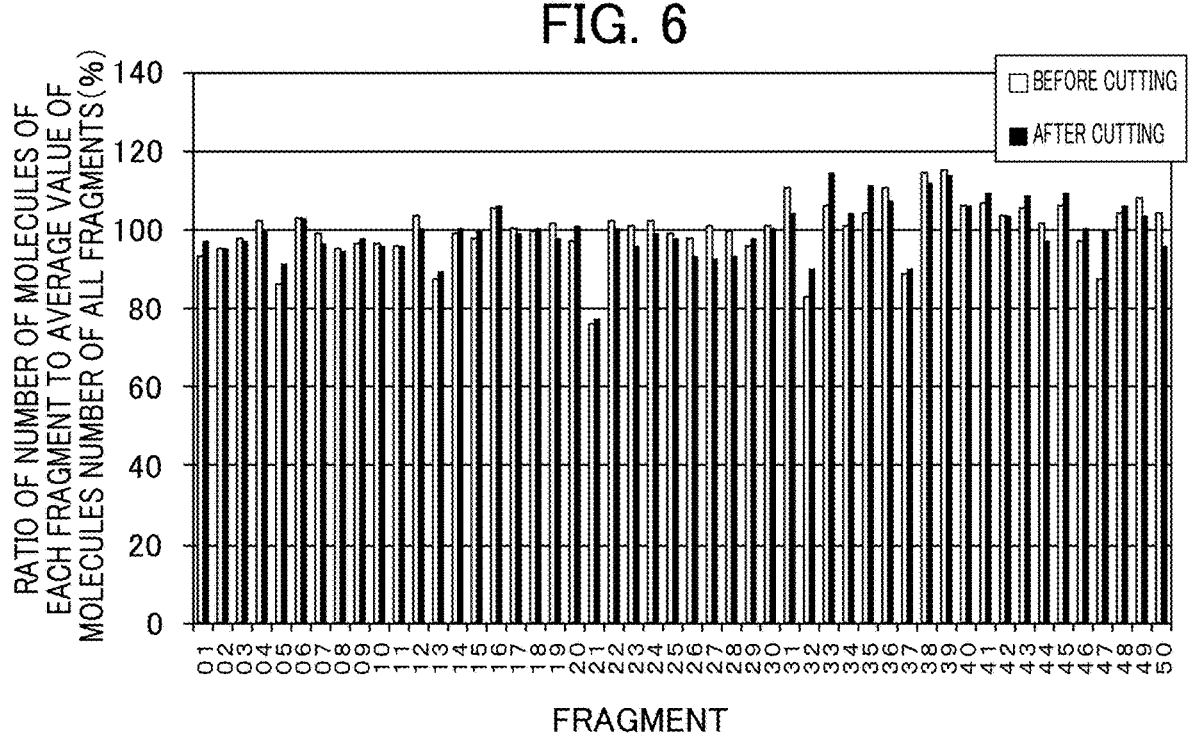
FIG. 6 an illustration showing the distribution of the number of molecules of each kind of DNA unit fragment before and after size-based selection. A group of plasmids to be treated with BbsI, a group of plasmids to be treated with AarI, and a group of plasmids to be treated with BsmBI, among plasmids harboring DNA unit fragments in Example 1 of the present invention, had been treated with each restriction enzyme in one session and then combined together.
Figure 7:
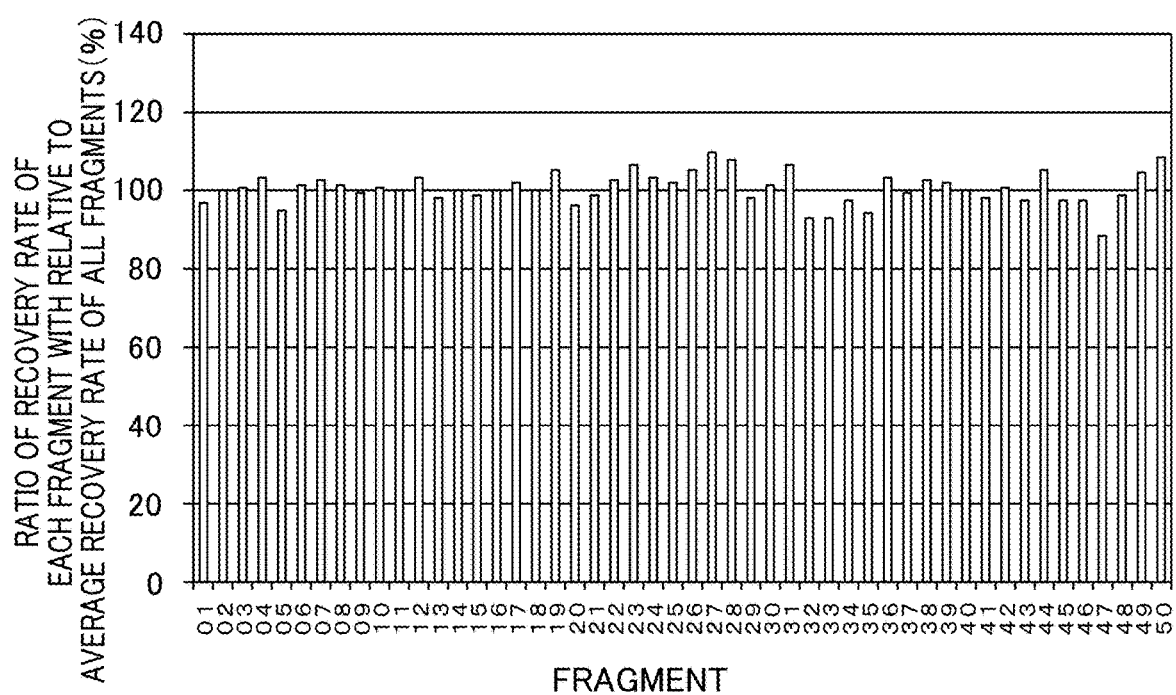
FIG. 7 an illustration showing the percentage change in the numbers of molecules of each kind of DNA unit fragment before and after size-based selection. A group of plasmids to be treated with BbsI, a group of plasmids to be treated with AarI, and a group of plasmids to be treated with BsmBI, among plasmids harboring DNA unit fragments in Example 1 of the present invention, had been treated with each restriction enzyme in one session and then combined together.

In order to confirm the number of moles contained in each group before and after size-based selection was determined by quantitative PCR. FIG. 6 shows distribution of the number of molecules of each DNA unit fragment before and after size-based selection, and FIG. 7 shows the percentage change in the number of molecules of each DNA unit fragment. It was confirmed that the molar ratio between the 50 fragments was substantially the same and was maintained after recovery.

<Gene Assembly>

Figure 8:
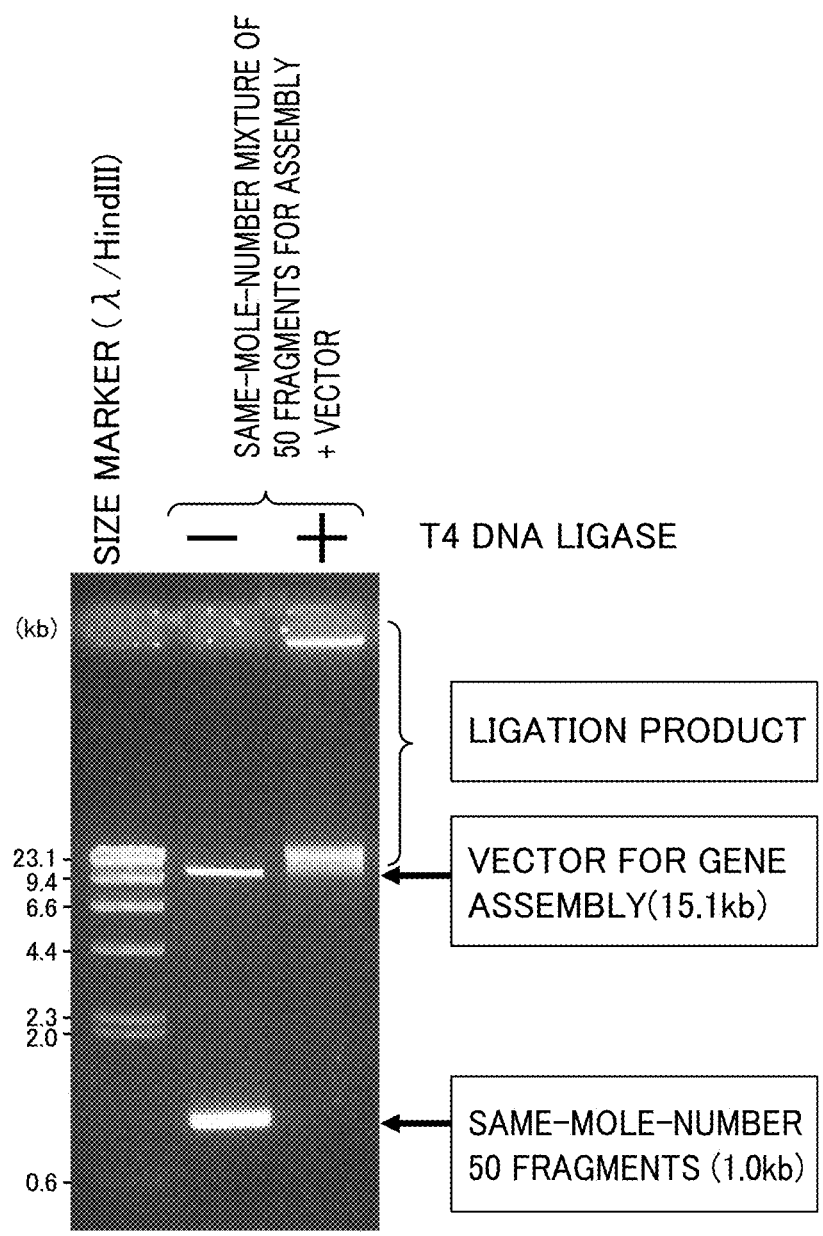
FIG. 8 a photograph showing the result of electrophoresis analyzing the product of ligation of a DNA unit fragment and a DNA vector in Example 1 of the present invention.

The resulting same-mole-number mixture of Fragments Nos. 01 to 50 had a DNA concentration by weight of 98 ng/µl and a sum of the lengths of the base sequences of 48,522 bp. On the other hand, the DNA vector (pGETS118-AarI/AarI) had a DNA concentration by weight of 190 ng/µl, and its full length was 15,139 bp. This length-weight ratio was used for obtaining a same-mole-number mixture of the both DNA molecules, in other words, the same-mole-number mixture of Fragments Nos. 01 to 50 was mixed with the DNA vector at a ratio of 6.21 µl:1.00 µl. To 7.2 µl of the resulting same-mole-number mixed solution, 8.2 µl of 2× ligation buffer was added, and the entire mixture was incubated at 37° C. for 5 min. Thereto, 1 µl of T4 DNA ligase (Takara) was added, followed by incubation at 37° C. for 4 h. A portion of the resulting mixture was analyzed by electrophoresis, and successful ligation was confirmed (FIG. 8). An 8-µl portion of the mixture was collected to a tube, to which 100 µl of a *Bacillus subtilis* competent cell was added, followed by rotation culture at 37° C. for 30 min in a duck rotor. After 300 µl of an LB medium was added thereto, another session of rotation culture was conducted at 37° C. for 1 h in a culture rotator. The resulting culture medium was spread onto an LB plate supplemented with 10 µg/ml tetracycline, followed by overnight culture at 37° C. As a result, 250 colonies were obtained.

<Checking Structures of Plasmid in Transformant>

Figure 9:
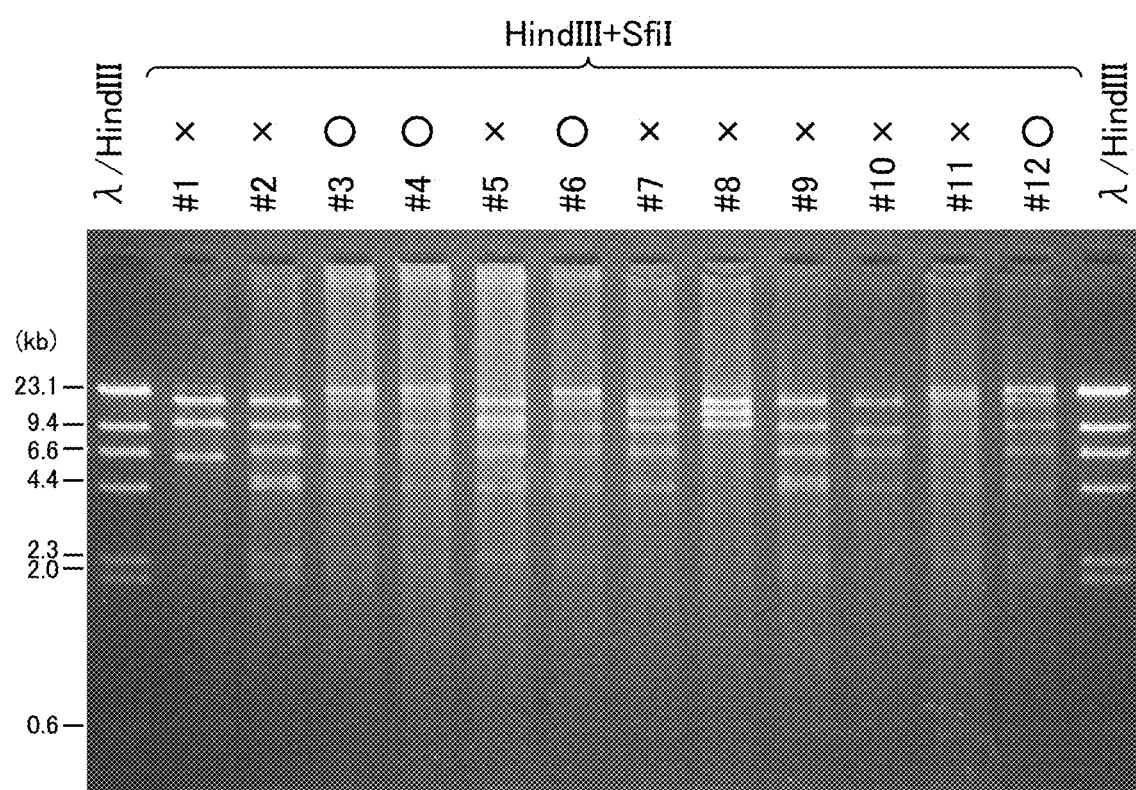
FIG. 9 a photograph showing the result of electrophoresis in Example 1 of the present invention, conducted after transforming *Bacillus subtilis* with a DNA concatemer obtained by ligation of a DNA unit fragment and a DNA vector, extracting plasmids from the resulting plurality of transformant strains of *Bacillus subtilis*, and subjecting the resulting plasmids to restriction enzyme treatment.
Figure 10:
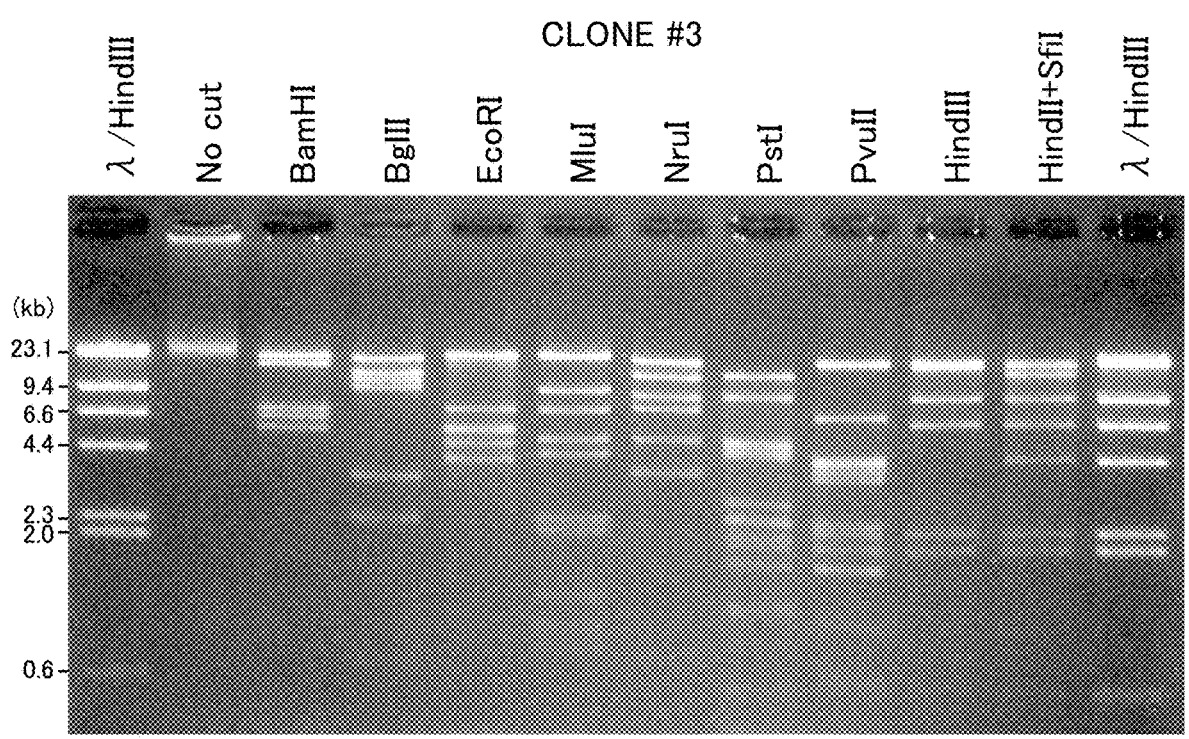
FIG. 10 a photograph showing the result of electrophoresis in Example 1 of the present invention, conducted after extracting plasmids from a plurality of transformant strains of *Bacillus subtilis*, subjecting the resulting plasmids to restriction enzyme treatment and electrophoresis, selecting a *Bacillus subtilis* clone containing a target DNA assembly based on the electrophoresis photograph, and conducting restriction enzyme treatment.

12 strains of colonies were randomly selected, and each of them was cultured overnight in an LB medium supplemented with 2 ml of 10 µg/ml tetracycline. For increasing the number of copies of the plasmid inside, IPTG was added to achieve a final concentration of 1 mM, followed by culturing at 37° C. for 3 h. The plasmid was extracted from the resulting bacterial cells, followed by double digestion with the restriction enzymes HindIII and SfiI. Electrophoresis analysis was conducted, and 4 out of the 12 strains gave the desired cleavage pattern (FIG. 9). Each of these 4 strains was subjected to cesium chloride-ethidium bromide density gradient ultracentrifugation to give a large amount of the plasmid, and the plasmid was cleaved with 13 kinds of restriction enzymes. Electrophoresis analysis revealed that all the cleaved fragments derived from each of the 4 strains gave expected patterns (FIG. 10). Further, the entire region, except for the vector region, of the plasmid derived from each of the 4 strains was sequenced, and, as a result, the resulting base sequence was in complete agreement with the expected base sequence.

<Checking Functions of Gene Assemblies>

Figure 11:
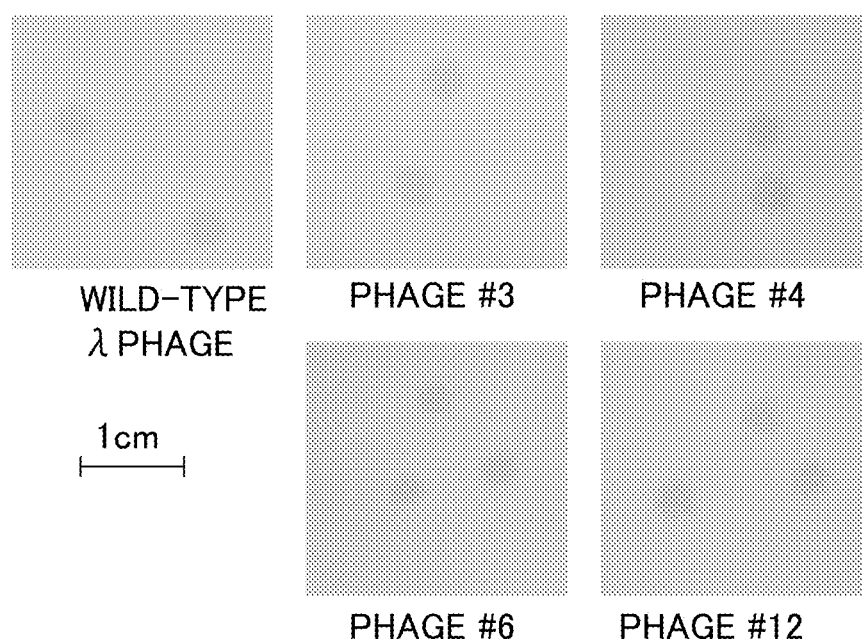
FIG. 11 an illustration showing that selected DNA assemblies formed lambda phage DNA plaques in Example 1 of the present invention.
Figure 12:
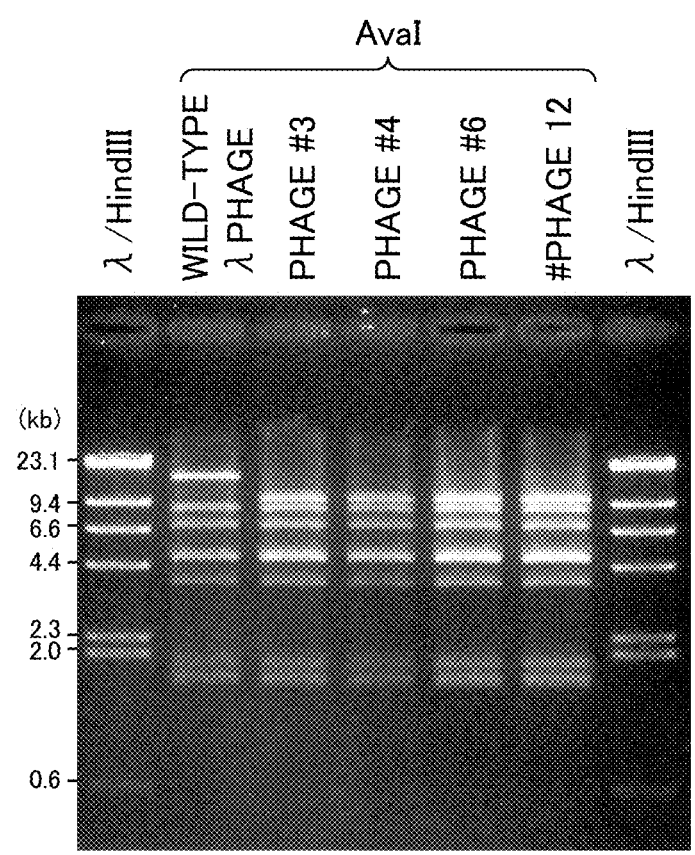
FIG. 12 a photograph showing genomes of selected DNA assemblies and wild-type lambda phage after treated with the restriction enzyme AvaI, in Example 1 of the present invention.

Lambda phage functions of the plasmid derived from each of the 4 strains were checked in terms of plaque-forming ability, as follows. Each of the assembly-harboring plasmids called #3, #4, #6, and #12 was cleaved with lambda terminase (Lambda terminase, Epicentre) to give a vector part and a gene assembly part. The latter was added to a lambda packaging extract (Gigapack III Plus Packaging Extract, Agilent Technologies). *Escherichia coli* (strain VCS257) was infected with the resultant, and was spread on an LB plate, followed by overnight culture at 37° C. As a result, plaque formation was observed. It was confirmed that the shape of the plaques was similar to that of the plaques concurrently obtained by lambda phage DNA manufactured by Toyobo Co., Ltd. (FIG. 11). Phage DNA was purified from the plaques formed by the plasmid, and was cleaved with the restriction enzyme AvaI for checking the presence of the mutation introduced. As shown in FIG. 12, the resulting cleavage pattern displayed was different from the one displayed by the lambda phage DNA manufactured by Toyobo Co., Ltd., and the presence of an AvaI site was confirmed in each phage as planned. Thus, it was confirmed that the lambda phage genome constructed by assembling all the 50 fragments, namely, Fragments Nos. 01 to 50, was fully adequate in terms of its base sequence and its plaque-forming ability.

These results showed that the 50 DNA unit fragments as constituents of lambda phage DNA and the DNA vector (pGETS118-AarI/AarI), a total of 51 DNA fragments, were successfully joined together.

Example 2, Construction of Artificial Operon of Mevalonate Pathway by Assembling 55 DNA Unit Fragments and DNA Vector The isoprenoids are known to be a large class of compounds having an isoprene unit as a skeleton and are synthesized from a common starting compound, which is isopentenyl diphosphate (IPP). There are two pathways known for IPP production starting from the glycolytic pathway, namely, the mevalonate pathway and the non-mevalonate pathway. Both of these pathways may be present in a single living organism, but *Escherichia coli* only has the non-mevalonate pathway. In order to enhance the ability of *Escherichia coli* to produce IPP, a part of the genes coding for the mevalonate pathway in yeast, a eukaryote, was artificially constructed by assembling synthetic DNA fragments according to the frequency in use of codons occurring in *Escherichia coli*, as follows.

<Designing Sequence of Artificial Operon of Mevalonate>

There are 3 genes (ERG10 (1.2 kb), ERG13 (1.5 kb), and HMG1 (3.2 kb)) necessary in the first half of the mevalonate pathway in yeast, namely, the metabolic pathway starting from acetyl CoA to mevalonic acid. The codons in these 3 genes were redesigned according to the frequency in use of codons occurring in *Escherichia coli* to give 3 artificial genes, which were then made into an artificial operon (5,951 bp) (SEQ ID NO:4) (the full-length sequence shown under SEQ ID NO:4 had a size of 5,955 by including 4 bases to serve as a protruding end, as described below. The redesigning of the gene codons in yeast to gene codons in *Escherichia coli* was conducted by ranking yeast synonymous codons based on the frequency in appearance of them occurring among all genes in yeast, also ranking *Escherichia coli* synonymous codons based on the frequency in appearance of them occurring among all genes in *Escherichia coli*, and exchanging between codons in the same rank.

<Designing DNA Unit Fragment>

A restriction enzyme that had no potential to cleave the 5,951-bp DNA sequence after the exchange between synonymous codons was looked for, in the same manner as in Example 1. The result showed that the DNA sequence contained no recognition sequence of the restriction enzyme AarI and therefore had no potential to be cleaved with AarI. Therefore, AarI was selected for cleaving in the process of all clone preparation. The full-length sequence (5,951 bp) was divided into 55 fragments, each of which was 108 by long on average. This size was designated as the size of each ideal dividing unit. Near boundaries between these dividing units, the presence of any one of particular sequences (60 combinations in total, consisting of 44 combinations left by subtracting 8 palindromic combinations from all 52 combinations consisting of 2 bases in total selected from A and T and 2 bases in total selected from C and G (Group III described above) and all 16 combinations with no 3 consecutive bases selected from C and G out of all 32 combinations consisting of 1 base in total selected from A and T and 3 bases in total selected from C and G (Group IV described above)) was searched for. As a result, one of these particular sequences were found to be occurred within ±7 by to each side of the ideal dividing boundary. Based on these results, the full-length sequence was divided into 55 fragments, each having a size from 98 by to 115 bp. Table 2 shows the dividing units and the protruding base sequences within a DNA assembly in Example 2. To the boundary between a mevalonate-pathway gene group and a gene-assembling vector, the protruding sequences (ATTA and AAAA) consisting only of A and/or T were utilized.

TABLE 2

| Fragment | Sequence (Including AarI site. Four nucleotides underlined indicates protrusion sequence. 5'→3') | Full-length (bp) | SEQ ID NO: |
|---|---|---|---|
| MEV001 | cacctgcacgt<br>attaGGCCTgttTGGCCGTGACACCGGACAATGAGTAatgTCGCAAAATGTGTACA<br>TTGTCTCAACCGCACGCACTCCGATTGGCTCCTTCCAAGGCTCGTTGTCacgtgcaggtg | 127 | 11 |
| MEV002 | cacctgcacgtTGTCTTCTAAGACGGCCGTAGAACTGGGCGCGGTGGCGTTAAAAGGAGCAC<br>TGGCGAAGGTGCCGGAACTGGATGCCTCTAAGGATTTTGACGAAATTATTTTTGGCAAT<br>GTGCTCTCacgtgcaggtg | 140 | 12 |
| MEV003 | cacctgcacgtTCTCGGCAAACCTGGGACAGGCGCCCGCACGCCAGGTGGCGCTGGCGGCAG<br>GCCTGAGCAACCATATAGTGGCCAGTACGGTGAATAAGGTTTGCGCCTCTGCGATGacgt<br>gcaggtg | 129 | 13 |
| MEV004 | cacctgcacgtGATGAAGGCCATAATTCTGGGCGCGCAGTCTATAAAATGCGGCAACGCGGA<br>TGTGGTTGTCGCGGGCGGCTGCGAATCGATGACCAATGCCCCGTACTACATGCCGGCCG<br>CACGacgtgcaggtg | 136 | 14 |
| MEV005 | cacctgcacgtCACGGGCTGGCGCAAAATTTGGACAGACCGTGCTCGTGGATGGCGTTGAAC<br>GCGATGGGCTGAATGATGCTTACGATGGCTTGGCAATGGGCGTCCACGCCGAAAAGTG<br>CGCACacgtgcaggtg | 136 | 15 |
| MEV006 | cacctgcacgtGCACGGGATTGGGATATTACCCGCGAACAGCAGGACAACTTTGCAATAGAA<br>TCTTACCAGAAATCGCAGAAATCGCAGAAGGAAGGCAAATTCGACAACGAAATTGTCC<br>acgtgcaggtg | 131 | 16 |
| MEV007 | cacctgcacgtGTCCCAGTGACTATTAAGGGTTTTCGCGGCAAGCCAGATACCCAGGTTACAA<br>AGGACGAGGAACCAGCGCGCTTACACGTGGAAAAACTGCGCTCGGCCCGTACCGTGTT<br>CCAacgtgcaggtg | 135 | 17 |
| MEV008 | cacctgcacgtTCCAGAAAGAAAATGGCACCGTGACCGCAGCGAATGCGTCGCCGATAAATG<br>ATGGCGCGGCCGCAGTTATACTGGTGTCTGAAAAAGTGCTGAAGGAAAAGAACCTGAA<br>GCCACTGacgtgcaggtg | 138 | 18 |
| MEV009 | cacctgcacgtACTGGCGATTATAAAAGGCTGGGGCGAGGCAGCGCATCAGCCGGCGGATTT<br>TACGTGGGCGCCGTCGCTCGCCGTGCCGAAGGCGCTGAAACATGCGGGAATAGAAGAC<br>ATAAACTCacgtgcaggtg | 139 | 19 |
| MEV010 | cacctgcacgtACTCGGTGGATTACTTTGAATTCAACGAAGCATTTTCAGTGGTTGGCCTGGT<br>AAATACCAAGATTCTGAAGTTGGACCCGTCGAAGGTGAACGTCTATGGCGGCGCGGTG<br>Gacgtgcaggtg | 133 | 20 |

TABLE 2-continued

| Fragment | Sequence (Including AarI site. Four nucleotides underlined indicates protrusion sequence. 5'→3') | Full-length (bp) | SEQ ID NO: |
|---|---|---|---|
| MEV011 | cacctgcacgt<u>GTGG</u>CGTTGGGCCACCCGCTGGGCTGCTCGGGCGCGCGTAGTGGTGACGCTTTTGTCTATATTACAACAGGAAGGTGGCAAGATAGGCGTGGCAGCAATTTG<u>CAAC</u>acgtgcaggtg | 130 | 21 |
| MEV012 | cacctgcacgt<u>CAAC</u>GGCGGCGGCGGCGCGTCTTCGATTGTTATTGAAAAGATCtaaGGCCTtgaTGGCCAACGCGGGAGATTTTTCatgAAACTATCCACCAAACTCTGCTGGTGCGGCATTAA<u>AGGT</u>acgtgcaggtg | 140 | 22 |
| MEV013 | cacctgcacgt<u>AGGT</u>CGCCTCCGTCCCCAGAAGCAGCAGCAGTTACACAACACGAATCTGCAGATGACCGAATTGAAAAAACAGAAGACTGCGGAACAGAAAACTCGCCCACAG<u>AACG</u>acgtgcaggtg | 129 | 23 |
| MEV014 | cacctgcacgt<u>AACG</u>TTGGCATTAAAGGCATACAGATTTACATACCGACCCAGTCGCGTTAATCAGTCGGAGTTGGAGAAATTTGATGGAGTGTCGCAGGGCAAATACACGATTGGCCTTGG<u>ACAG</u>acgtgcaggtg | 136 | 24 |
| MEV015 | cacctgcacgt<u>ACAG</u>ACTAATATGTCGTTTGTTAACGACCGCGAAGATATATACTCAATGTCTTTGACCGTGCTGTCGAAGCTGATAAAGAGCTACAATATAGACACTAATAAAA<u>TTGG</u>acgtgcaggtg | 130 | 25 |
| MEV016 | cacctgcacgt<u>TTGG</u>CCGCTTAGAAGTTGGCACCGAAACCCTTATTGACAAGTCTAAGTCGGTTAAGTCGGTTCTGATGCAGCTGTTTGGCGAAAATACCGACGTTGAAGGCATTGACACAC<u>TCA</u>acgtgcaggtg | 136 | 26 |
| MEV017 | cacctgcacgt<u>CTCA</u>ACGCATGCTACGCGGCACTAATGCTCTGTTCAATTCGCTGAATTGGATTGAATCGAATGCCTGGGATGGCCGCGACGCAATTGTCGTGTGTGGCGATATTGCAATA<u>TACG</u>acgtgcaggtg | 137 | 27 |
| MEV018 | cacctgcacgt<u>TACG</u>ATAAGGGCGCAGCCCGCCCGACTGGCGGCGCAGGCACCGTGGCGATGTGGATAGGCCCAGATGCGCCGATTGTCTTTGACTCGGTCCGCGCGTCGTACATG<u>GAAC</u>acgtgcaggtg | 131 | 28 |
| MEV019 | cacctgcacgt<u>GAAC</u>ACGCATACGATTTTTACAAGCCGGATTTCACTAGTGAATATCCATACGTTGATGGCCATTTTTCCTTAACCTGCTACGTTAAGGCGCTCGATCAGGTGTACAAGA<u>GCTA</u>acgtgcaggtg | 135 | 29 |
| MEV020 | cacctgcacgt<u>GCTA</u>TTCTAAGAAGGCGATTTCGAAAGGGCTGGTGAGTGATCCTGCGGGCTCAGATGCGCTGAATGTGCTGAAATATTTCGACTACAATGTGTTCCATGTGCCGACTT<u>GCAA</u>acgtgcaggtg | 134 | 30 |
| MEV021 | cacctgcacgt<u>GCAA</u>ACTGGTTACGAAATCCTACGGCCGCTTATTGTATAATGATTTCCGCGCAAACCCACAGCTGTTCCCGGAAGTGGACGCAGAATTAGCGACCAGAGATTATGACGAA<u>TCG</u>acgtgcaggtg | 135 | 31 |
| MEV022 | cacctgcacgt<u>ATCG</u>TTAACTGATAAGAATATTGAAAAAACCTTTGTGAACGTGGCGAAGCCGTTCCACAAAGAGCGCGTGGCACAGTCGCTGATTGTGCCGACGAATACGGGCAATATGTACA<u>CTGC</u>acgtgcaggtg | 139 | 32 |
| MEV023 | cacctgcacgt<u>CTGC</u>CTCGGTGTATGCAGCATTTGCCTCGTTGTTAAATTATGTGGGTTCGGACGACTTACAGGGAAAGCGGGTGGGCTTATTTTCGTACGGCTCTGGCTTAGCGGC<u>CTCG</u>acgtgcaggtg | 132 | 33 |
| MEV024 | cacctgcacgt<u>CTCG</u>TTGTATTCGTGTAAAATTGTGGGCGACGTTCAGCATATTATAAAGGAATTAGATATTACCAATAAATTAGCAAAGCGCATAACTGAAACCCCGAAGGATTAC<u>GAA</u>acgtgcaggtg | 131 | 34 |
| MEV025 | cacctgcacgt<u>CGAA</u>GCGGCAATAGAACTGCGCGAAAACGCACATCTGAAGAAGAATTTCAAACCACAGGGCTCTATTGAGCATCTGCAGAGCGGCGTGTACTACCTGACTAATATAGATGACacgtgcaggtg | 134 | 35 |
| MEV026 | cacctgcacgt<u>TGAC</u>AAATTTCGCCGCTCGTACGATGTGAAAAAAtaaGGCCTcgaTGGCCGTGAACTGGATAGTGAAATAatgCCCCCCTTGTTCAAGGGTCTTAAACAAATGGC<u>CAAG</u>acgtgcaggtg | 131 | 36 |
| MEV027 | cacctgcacgt<u>CAAG</u>CCGATTGCATATGTGTCCCGCTTTTCAGCTAAACGACCGATTCATATCATCCTCTTTTCGTTGATAATCTCTGCCTTCGCGTATTTGTCTGTTATTCAATATTACTTCAACGG<u>CTGG</u>acgtgcaggtg | 143 | 37 |
| MEV028 | cacctgcacgt<u>CTGG</u>CAGTTGGATTCCAACAGCGTGTTTGAAACCGCGCCGAACAAAGACTCTAATACCTTGTTTCAGGAATGCTCTCATTACTACCGCGATTCTTCGTTGGATGGCTGGG<u>TCTA</u>acgtgcaggtg | 135 | 38 |
| MEV029 | cacctgcacgt<u>GTCT</u>CCATAACTGCTCATGAAGCGAGCGAGTTACCGGCACCGCACCATTACTATTTGTTAAATCTTAATTTCAACAGCCCAAACGAAACCGACTCTATTCC<u>GGAA</u>acgtgcaggtg | 127 | 39 |

TABLE 2-continued

| Fragment | Sequence (Including AarI site. Four nucleotides underlined indicates protrusion sequence. 5'→3') | Full-length (bp) | SEQ ID NO: |
|---|---|---|---|
| MEV030 | cacctgcacgt<u>GGAA</u>TTGGCGAATACAGTGTTTGAGAAAGATAACACGAAATATATTCTTCAGGAAGATCTAAGCGTGTCTAAAGAAATTTCGTCGACCGATGGTACAAAATGGCGTTTACGCAGC<u>GACC</u>acgtgcaggtg | 141 | 40 |
| MEV031 | cacctgcacgt<u>GACC</u>GCAAAAGCCTCTTCGACGTCAAGACATTAGCCTATTCGCTATACGATGTCTTTTCCGAAAACGTCACTCAGGCCGACCCCTTTGACGTTCTCATTA<u>TGGT</u>acgtgcaggtg | 126 | 41 |
| MEV032 | cacctgcacgt<u>TGGT</u>GACCGCATACTTGATGATGTTCTACACTATCTTCGGACTATTCAACGACATGCGTAAGACTGGGTCCAACTTTTGGCTGAGTGCATCGACGGTAGTTAACTCGGCC<u>TCCT</u>acgtgcaggtg | 136 | 42 |
| MEV033 | cacctgcacgt<u>TCCT</u>CCCTCTTCTTAGCCCTGTATGTTACTCAGTGCATTTTGGGAAAAGAAGTGTCTGCCTTAACCCTCTTTGAAGGCCTGCCATTCATTGTCGTGGTGGTGGGCTTC<u>AGCA</u>acgtgcaggtg | 135 | 43 |
| MEV034 | cacctgcacgt<u>AGCA</u>CAAAATAAAGATTGCACAATATGCACTTGAGAAATTTGAACGCGTTGGCTTATCGAAACGTATTACCACTGATGAAATAGTGTTTGAATCTGTAAGTGAAGAGGGCGGCCG<u>GCTG</u>acgtgcaggtg | 141 | 44 |
| MEV035 | cacctgcacgt<u>GCTG</u>ATTCAGGACCATCTGCTCTGCATTTTTGCATTTATAGGTTGTTCGATGTATGCGCACCAGCTGAAGACCCTGACGAATTTCTGTATCTTATCCG<u>CCTT</u>acgtgcaggtg | 124 | 45 |
| MEV036 | cacctgcacgt<u>CCTT</u>TATATTGATTTTTGAACTGATTTTAACCCCAACGTTTTATTCGGCGATATTAGCTCTCCGCCTTGAAATGAACGTGATACACCGCTCGACCATTATAAAGCAGACGTTA<u>GAAG</u>acgtgcaggtg | 139 | 46 |
| MEV037 | cacctgcacgt<u>GAAG</u>AAGACGGCGTGGTGCCGTCGACGGCCCGCATAATTTCGAAAGCCGAAAAGAAATCTGTCTCGTCGTTCTTAAACCTAAGCGTAGTGGTTATTATAATGAAACTATC<u>GGTT</u>acgtgcaggtg | 136 | 47 |
| MEV038 | cacctgcacgt<u>GGTT</u>ATCCTTCTGTTTGTTTTCATAAATTTTTATAATTTTGGCGCCAACTGGGTTAACGATGCATTCAACTCCCTGTACTTCGATAAGGAACGGGTGTCGTTGCC<u>GGAT</u>acgtgcaggtg | 131 | 48 |
| MEV039 | cacctgcacgt<u>GGAT</u>TTTATTACTTCAAACGCATCGGAAAATTTTAAAGAGCAGGCGATTGTGAGCGTTACTCCGTTATTATATTACAAACCTATTAAGTCTTACCAGAGAATTGAGGATATGGT<u>GCTC</u>acgtgcaggtg | 140 | 49 |
| MEV040 | cacctgcacgt<u>GCTC</u>TTGCTGCTCCGGAACGTTAGCGTGGCAATTCGGGATCGTTTCGTTAGCAAATTAGTGCTCTCTGCATTAGTCTGTAGCGCGGTTATAAACGTATATTTA<u>CTGA</u>acgtgcaggtg | 129 | 50 |
| MEV041 | cacctgcacgt<u>CTGA</u>ACGCGGCGCGCATTCATACTAGCTATACCGCCGACCAGCTGGTAAAAACCGAAGTTACTAAGAAGTCGTTTACCGCGCCAGTCCAGAAGGCGTCGACGCCG<u>GTGT</u>acgtgcaggtg | 131 | 51 |
| MEV042 | cacctgcacgt<u>GTGT</u>AACTAACAAAACGGTTATTTCGGGTTCAAAAGTTAAAAGCTTATCCTCGGCTCAGTCAAGTTCCTCCGGTCCATCCTCCTCGAGCGAGGAAGATGATTCTAGAGATATTGAA<u>AGTC</u>acgtgcaggtg | 143 | 52 |
| MEV043 | cacctgcacgt<u>AGTC</u>TGGATAAGAAAATCCGGCCATTAGAAGAATTAGAAGCCTTATTAAGCAGCGGTAACACGAAACAGCTGAAGAATAAAGAGGTTGCGGCACTGGTGATT<u>CAC</u>acgtgcaggtg | 127 | 53 |
| MEV044 | cacctgcacgt<u>TCAC</u>GGCAAGTTACCACTGTACGCGCTGGAGAAAAAATTAGGCGATACCACACGCGCTGTGGCTGTCCGGCGTAAGGCGCTCTCCATTCTGGCCGAAGCGCCAGTCTTAG<u>CCTC</u>acgtgcaggtg | 136 | 54 |
| MEV045 | cacctgcacgt<u>CCTC</u>GGATCGGTTACCGTATAAAAACTATGACTACGACAGAGTCTTTGGAGCGTGCTGCGAAAACGTGATCGGCTACATGCCACTGCCTGTGGGCGTGATCGGACC<u>TCTG</u>acgtgcaggtg | 132 | 55 |
| MEV046 | cacctgcacgt<u>TCTG</u>GTGATAGATGGCACGTCGTATCATATCCCGATGGCCACCACGGAGGGCTGCCTGGTCGCGTCGGCAATGCGGGGATGCAAGGCCATAAACGCGGGAGGCGGCGCC<u>ACGA</u>acgtgcaggtg | 135 | 56 |
| MEV047 | cacctgcacgt<u>ACGA</u>CCGTGTTAACCAAGGATGGCATGACGCGCGGACCGGTCGTTCGGTTCCCGACCCCTGAAACGCTCGGGCGCATGCAAGATCTGGTTAGACTCCGAAGAGGGTCAGAATG<u>CCAT</u>acgtgcaggtg | 138 | 57 |
| MEV048 | cacctgcacgt<u>CCAT</u>TAAAAAAGCGTTTAATTCGACGTCCCGCTTTGCCCGGCTTCAGCATATTCAGACCTGCTTGGCCGGTGATTTACTATTCATGCGCTTTCGCACGACCACCGG<u>CGAC</u>acgtgcaggtg | 132 | 58 |

TABLE 2-continued

| Fragment | Sequence (Including AarI site. Four nucleotides underlined indicates protrusion sequence. 5'→3') | Full-length (bp) | SEQ ID NO: |
|---|---|---|---|
| MEV049 | cacctgcacgt<u>CGAC</u>GCCATGGGCATGAACATGATTTCGAAAGGCGTTGAATACTCCTTAAAGCAGATGGTCGAAGAGTATGGATGGGAAGATATGGAGGTGGTTTCTGTGTCGGGCAATTACTG<u>CACT</u>acgtgcaggtg | 140 | 59 |
| MEV050 | cacctgcacgt<u>CACT</u>GACAAAAAACCGGCGGCAATAAATTGGATAGAAGGCCGGGCAAGAGCGTTGTTGCCGAAGCGACCATTCCAGGCGATGTGGTTCGCAAAGTATTAAA<u>AAGC</u>acgtgcaggtg | 128 | 60 |
| MEV051 | cacctgcacgt<u>AAGC</u>GATGTGTCTGCCCTGGTGGAGCTGAATATTGCGAAGAACCTGGTGGGTTCGGCCATGGCGGGGTCGGTGGGCGGTTTTAATGCCCATGCCGCGAACTTAGTAACGGC<u>GGTG</u>acgtgcaggtg | 137 | 61 |
| MEV052 | cacctgcacgt<u>GGTG</u>TTCCTGGCCTTAGGTCAGGATCCAGCCCAGAACGTGGAAAGCTCTAATTGCATCACGCTGATGAAAGAAGTAGACGGCGATCTGCGCATTTCTGTCTCTATGC<u>CGTC</u>acgtgcaggtg | 133 | 62 |
| MEV053 | cacctgcacgt<u>CGTC</u>TATAGAAGTCGGCACTATAGGCGGCGGCACCGTGTTGGAACCGCAGGGCGCAATGCTGGACTTATTAGGCGTCCGCGGACCCCATGCGACTGCGCCAGGCACTA<u>ATGC</u>acgtgcaggtg | 134 | 63 |
| MEV054 | cacctgcacgt<u>ATGC</u>CCGGCAGTTAGCCCGCATCGTGGCATGCGCAGTTCTGGCCGGCGAATTATCTTTATGCGCGGCATTGGCCGCAGGACATCTGGTGCAGAGCCATATGACT<u>CACA</u>acgtgcaggtg | 130 | 64 |
| MEV055 | cacctgcacgt<u>CACA</u>ATCGTAAACCAGCGGAACCGACGAAACCAAATAACCTGGACGCAACCGATATCAACCGGCTGAAAGATGGGTCTGTTACTTGTATTAAATCTtaaGGCCTTCTTGGCCaaaaacgtgcaggtg | 138 | 65 |

<Construction of DNA Unit Fragment from Synthetic DNA>

Each of the divided fragments obtained was prepared with 2 molecules of chemically synthesized 80-base DNA, according to a method by Rossi et al. (Rossi, J. J., and Itakura, K. 1982. J. Biol. Chem. 257, 9226-9229 (1982)). Specifically, each of the resulting divided fragments had these 2 chemically synthesized DNA molecules hybridizing to each other at the 3' end for a span of several tens bp, and also had an AarI recognition site introduced to the 5' end side so that the above-designed protruding sequence was to be formed between the AarI cleavage site and the 5' end by digestion. The hybridization between these 2 synthetic DNA molecules followed by template-dependent elongation reaction gave a double-stranded DNA unit fragment, which was then amplified by PCR in the way to be described below. The resultant double-stranded DNA unit fragment as well as a pair of PCR primers designed to hybridize with the AarI recognition site on each end, namely, a total of 3 kinds of DNA molecules, were used to be added in the PCR reaction, and consequently a DNA unit fragment flanked by AarI cleavage sites was obtained. The resultant DNA unit fragment was joined to *Escherichia coli* plasmid vector pMD19 by TA cloning method, followed by transformation of *Escherichia coli* for cloning method. Sequencing was then conducted to select a clone having a base sequence desirable for each fragment.

<Mixing Same Mole Numbers of Plasmids each Harboring DNA Unit Fragment>

Each of the 55 strains of *Escherichia coli* each harboring the resulting desired clone was cultured and then subjected to treatment with Plasmid mini-prep (QIAGEN), whereby 50 μl of a crude plasmid solution was obtained. A 1-μl sample of the resultant was analyzed with a spectrophotometer for trace amount detection, and the DNA concentration of it was determined as 82 ng/μl to 180 ng/μl. Each plasmid weighing about 5 μg was treated with Plasmid Safe, followed by enzyme inactivation by heating. Purification with Mini-elute PCR purification Kit (QIAGEN) gave 25 μl of a highly-pure plasmid solution. A 1-μl sample of the resultant was analyzed with a spectrophotometer for trace amount detection, and the concentration of it was determined as 108 ng/μl to 213 ng/μl. A 20-μl portion of the highly-pure plasmid solution was transferred into a separate tube and diluted with TE so as to make the concentration of the plasmid be mathematically 100 ng/μl. The resulting purified plasmid solution was reanalyzed with a microspectrophotometer to calculate the concentration, and, based on the concentration measurement, the volume (μl) of the solution containing 500 ng of the highly pure plasmid was accurately calculated to the second decimal place. A portion of each plasmid solution in an amount of this volume (about 5 μl) was separated into one tube, where this portion was combined with the other such portions. To the resulting same-mole-number plasmid mixture solution, which was about 275 μl in total volume, sterilized water having a volume twice the volume of the same-mole-number plasmid mixture solution, 137.5 μl of 10× Buffer_for_AarI, and 67.5 μl of the restriction enzyme AarI were added, followed by reaction at 37° C. overnight.

<Size-based Selection of 55 DNA Unit Fragments in One Session>

Figure 13:
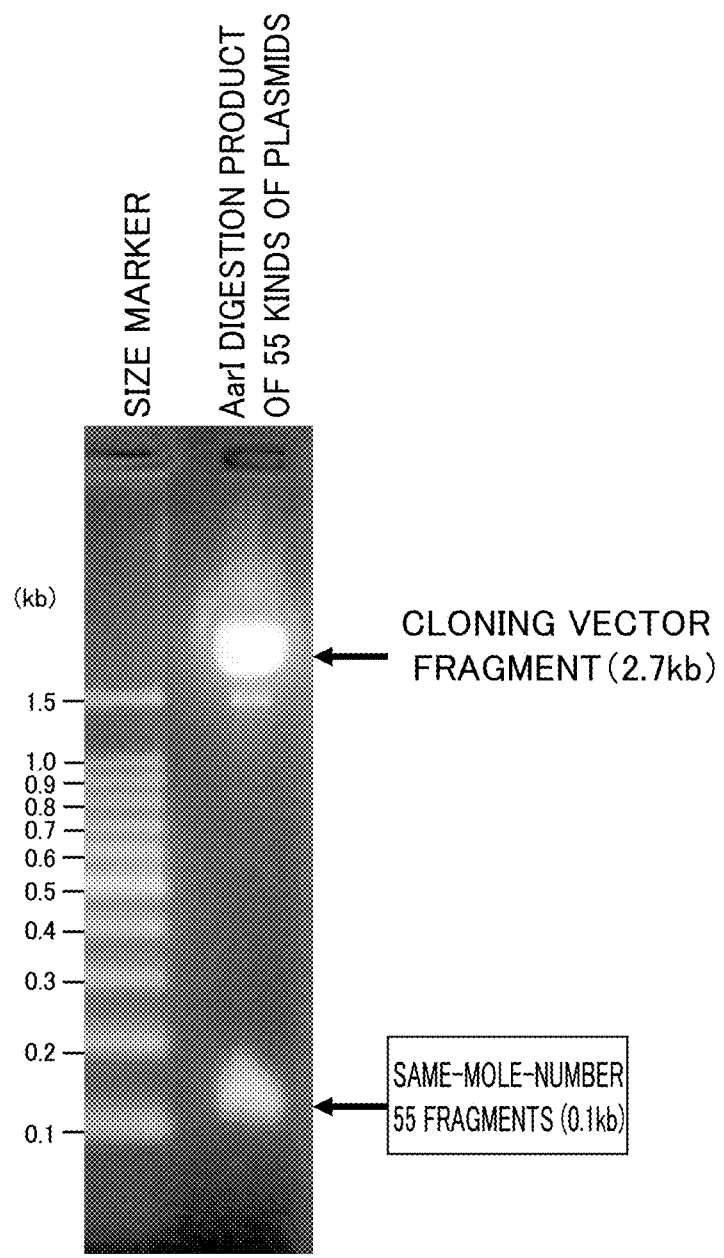
FIG. 13 a photograph showing the result of electrophoresis analyzing plasmids harboring DNA unit fragments after purification in Example 2 of the present invention. The plasmids had been treated with the restriction enzyme AarI in one session prior to electrophoresis.

To the resulting reaction solution, an equal amount of phenol-chloroform-isoamyl alcohol (25:24:1) was added for AarI inactivation, followed by centrifugation. The resulting supernatant was purified by ethanol precipitation, and the precipitate was dissolved in 20 μl of TE. The resultant, combined with xylene cyanol as a coloring agent for electrophoresis, was subjected to electrophoresis in 2.5% agarose gel with TAE buffer for 30 minutes at 100 V so as to separate the DNA vector pMD19 and the insert DNA unit fragment (FIG. 13). The gel was divided with a razor into segments, and one segment was stained with ethidium bromide to check the position of the target band that was attributed to the same-mole-number mixture of the 55 fragments. Then, from another segment of the gel left unstained, the target DNA band was cut out.

<Purification of Same-mole-number Mixture of DNA Unit Fragments>

DNA purification from the obtained gel segment was conducted with MiniElute Gel Extraction Kit (QIAGEN) as follows.

The volume of the gel was measured from the weight thereof, and CG Buffer having a volume 15 times the volume thus calculated was added, followed by incubation at 50° C. for 10 min for dissolving the gel. Thereto, isopropyl alcohol having a volume 5 times the volume of the gel segment was added, and the resulting liquid was placed in the column, followed by centrifugation to make the DNA adsorbed on the column. To the column, 500 µl of CG Buffer was added, followed by centrifugation for washing, and then 750 µl of PE Buffer was further added, followed by centrifugation for washing. In this way, the column was washed. The column was centrifuged one more time for complete removal of any residue. To the column, 10 µl of TE buffer was added, followed by centrifugation. Thus, a mixed solution of substantially the same number of moles of the 55 DNA unit fragments was obtained.

<Addition of DNA having Origin of Replication, to Same-mole-number Mixed Solution of DNA Unit Fragments>

The mixed solution was analyzed with a spectrophotometer for trace amount detection to measure the concentration, and the DNA concentration thereof was determined as 20 ng/µl. pGET151/AarI was also prepared at the same time in a concentration of 67 ng/µl. In consideration of these results as well as the ratio between the lengths of these (5955 bp:4306 bp), the same-mole-number mixed solution of the 55 fragments and the pGETS151/AarI were mixed in a ratio of 4.63:1.

<Gene Assembling>

Figure 14:
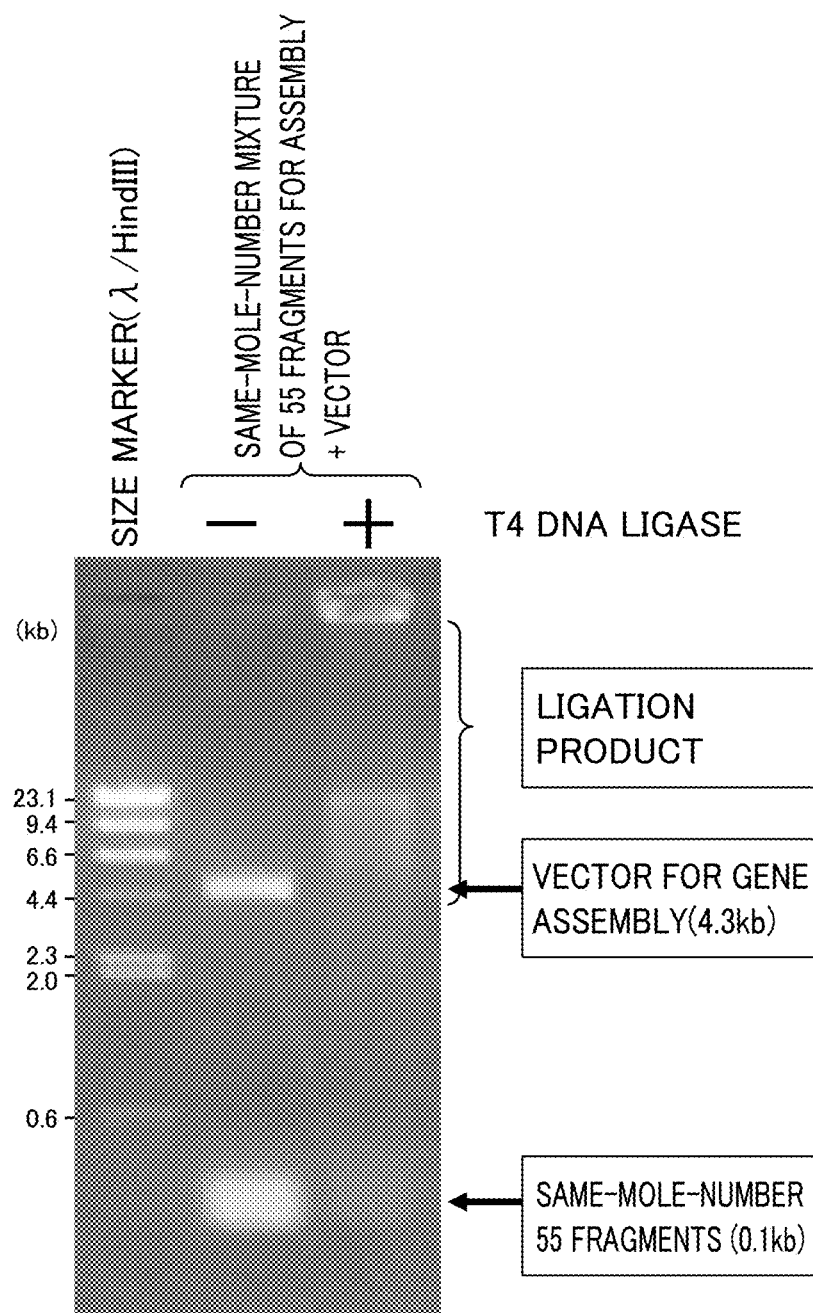
FIG. 14 a photograph showing the result of electrophoresis analyzing the product of ligation of a DNA unit fragment and a DNA vector in Example 2 of the present invention.

To 5.63 µl of the resulting same-mole-number mixed solution, 6.63 µl of 2× ligation buffer was added, followed by incubation at 37° C. for 5 mM. Thereto, 1 µl of T4 DNA ligase (Takara) was added, followed by incubation at 37° C. for 4 h. A sample of the resultant was analyzed by electrophoresis for checking whether or not ligation between the DNA unit fragments and the DNA vector in a tandem-repeat structure was successful (FIG. 14). After ligation, 8 µl of the resulting solution was added to a separate tube, to which 100 µl of a *Bacillus subtilis* competent cell was added, followed by rotation culture at 37° C. for 30 min in a duck rotor. Then, after 300 µl of an LB medium was added thereto, another session of rotation culture was conducted at 37° C. for 1 h in a culture rotator. The resulting culture medium was spread onto an LB plate supplemented with 10 µg/ml tetracycline.

<Transformation, and Checking Structures of Assembly>

Figure 16:
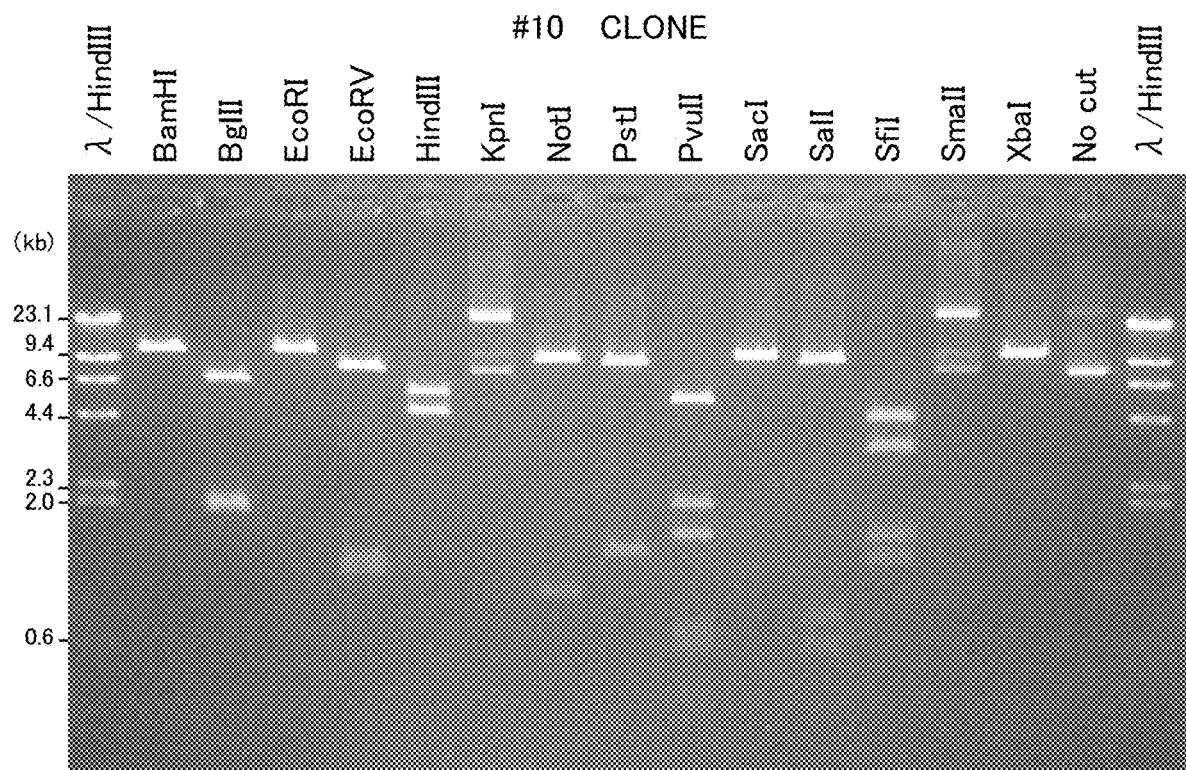
FIG. 16 a photograph showing the result of electrophoresis in Example 2 of the present invention, conducted after extracting plasmids from a plurality of transformant strains of *Bacillus subtilis*, subjecting the resulting plasmids to restriction enzyme treatment and electrophoresis, selecting a *Bacillus subtilis* clone containing a target DNA assembly based on the electrophoresis photograph, and conducting restriction enzyme treatment.

From the resulting 154 colonies, 24 clones were randomly selected and inoculated into an LB medium supplemented with 10 µg/ml tetracycline. IPTG was added thereto so as to achieve a final concentration of 1 mM during the logarithmic phase, followed by culturing to reach the stationary phase. The DNA plasmid was extracted and was treated with the restriction enzyme PvuII, followed by electrophoresis for checking the cleavage pattern (FIG. 15). As a result, 2 clones (#10 and #20) were found to have the expected base sequence, and these plasmids were subjected to treatment with other restriction enzymes and then to electrophoresis for determining their structures in more detail, which were found to be in agreement with the target structure (FIG. 16). It was confirmed that sequencing these plasmids indicated that these clones #10 and #20 had base sequences as designed.

These results showed that the 55 DNA unit fragments as constituents of the artificial operon of the mevalonate pathway and the DNA vector (pGETS151-pBR), a total of 56 DNA fragments, were successfully joined together.

Thus, it was confirmed that the method of the present invention of constructing a DNA concatemer was capable of joining 50 or more DNA fragments together. The reason for this many DNA fragments being successfully joined together was probably that the numbers of moles of DNA unit fragments are close to one another more accurately.

The reason that the numbers of moles of DNA unit fragments in the DNA unit fragment composition prepared by the method of the present invention were close to one another more accurately was probably the following.

When the concentration of each DNA unit fragment in the solution containing the DNA unit fragment was measured in Examples 1 and 2, the DNA unit fragment being measured had the corresponding auxiliary sequence attached thereto (specifically, a circular DNA plasmid). Even if the base sequences of different kinds of DNA unit fragments varied greatly, the corresponding auxiliary sequences thus attached contributed to reduction in distribution of the lengths of different base sequences being measured. As a result, when the measurement result was used to calculate the number of moles of each kind of DNA unit fragment, errors in the calculation were reduced. Then, when the resulting measurement result was used for taking a portion from each of the solutions so that the number of moles of DNA unit fragment in each portion was adjusted to be substantially the same, the molar ratio between different portions tended to be close to 1. Probably for this reason, the numbers of moles of DNA unit fragments became more accurately substantially the same.

In Example 1, the standard deviation of the distribution of the sum of the lengths of the base sequence of each DNA unit fragment and the base sequence of the corresponding auxiliary sequence attached to the DNA unit fragment was 3691.4 bp±6.6 bp, and ranged from −0.18% to 0.18% of the average value of the sum of the lengths. In Example 2, the standard deviation of the distribution of the sum of the lengths of the base sequence of each DNA unit fragment and the base sequence of the corresponding auxiliary sequence attached to the DNA unit fragment was 2828.2 bp±4.5 bp, and ranged from −0.16% to 0.16% of the average value of the sum of the lengths. In Examples 1 and 2, the standard deviation was smaller than the average value of the sum of the lengths, and probably for this reason, errors in the calculation of the number of moles of each DNA unit fragment conducted based on the measurement result of the DNA concentration in the solution were reduced.

The ratio of the average length of the base sequence of the corresponding auxiliary sequence attached to each DNA unit fragment to the average length of the base sequence of the DNA unit fragment was about 2.7 in Example 1 and about 27 in Example 2. Because the average length of the base sequence of the corresponding auxiliary sequence attached to each DNA unit fragment was longer than the average length of the base sequence of the DNA unit fragment, errors in the calculation of the number of moles of each DNA unit fragment conducted based on the measurement of the DNA concentration in the solution were further reduced, and probably for this reason, errors in the calculation of the number of moles of each DNA unit fragment conducted based on the measurement of the DNA concentration in the solution were further reduced.

In Example 1 and Example 2, designing each DNA unit fragment was conducted in a way that the base sequence of each DNA assembly when divided by the number of kinds of its constituent DNA unit fragments into equal parts had a non-palindromic sequence near each boundary between two adjacent equal parts, and that each DNA unit fragment was separated by the non-palindromic sequence from an adjacent DNA unit fragment. The DNA unit fragments thus designed had substantially the same length. When the DNA unit fragments were subjected to removal of corresponding auxiliary sequences with restriction enzymes and to subsequent electrophoresis for size-based selection, the DNA unit fragments were observed as a band at substantially the same position, allowing recovery of all the DNA unit fragments to be completed in a single session of size-based selection. Therefore, operation efficiency was enhanced.

In Example 1, the DNA unit fragments were divided into groups, each group for a single restriction enzyme to be used for removal of the corresponding auxiliary sequence (3 kinds of restriction enzymes in Example 1, 1 kind of restriction enzyme in Example 2). In this case, each group consisted of two or more solutions each containing a different DNA unit fragment. The two kinds or more solutions could be mixed together before the removal step. As a result, a separate session of restriction enzyme treatment was not required for respective DNA unit fragment, but, instead, a single session of restriction enzyme treatment was enough to treat an entire restriction-enzyme group. Consequently, the operation efficiency of DNA concatemer construction was enhanced. It was confirmed that even such mixture is used, the number of moles of many DNA unit fragments were substantially the same when mixed together, and therefore the many DNA unit fragments were successfully joined together as described above.

Test Example 1, Checking Level of Repeating Unit of Redundancy (r) of DNA Assembly Unit Required for Transformation of *Bacillus subtilis* DNA Plasmid In order to check the level of the repeating number (redundancy) r of DNA assembly unit required for transformation of *Bacillus subtilis* DNA plasmid, the following test was conducted.

Figure 17:
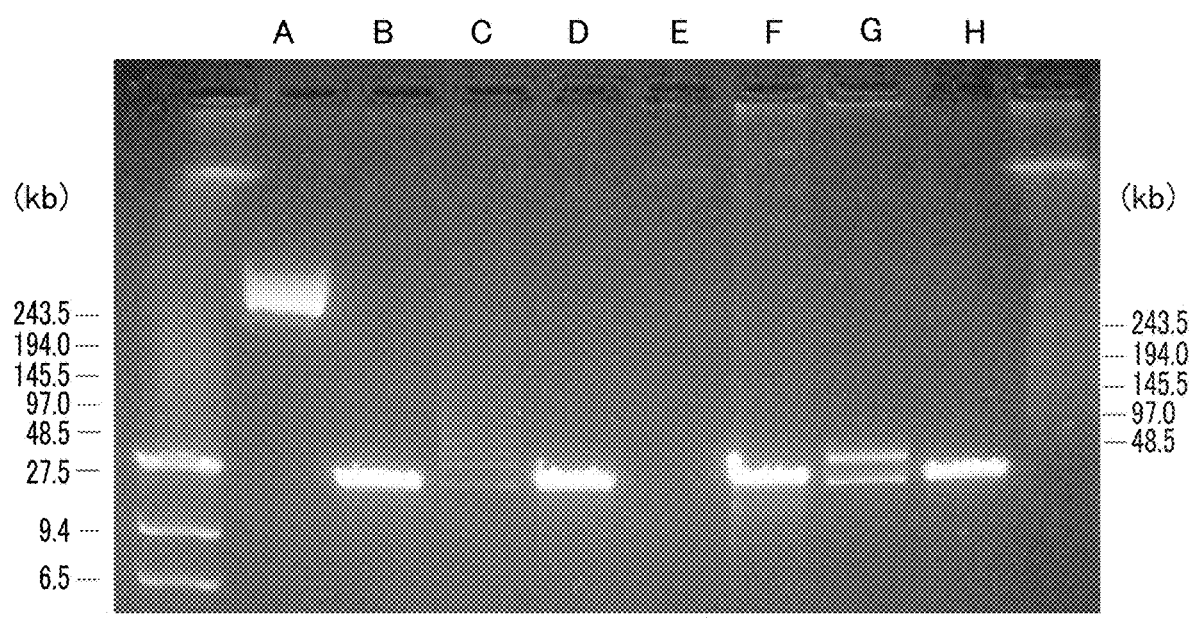
FIG. 17 a photograph showing the result of electrophoresis analyzing a DNA (A) to a DNA (H) used in Test Example 1.

The plasmid pGETS11840-Pr-SfiI-pBR (SEQ ID NO:1) harboring an origin of replication effective in *Bacillus subtilis* was used to prepare the following DNA molecules (A) to (H).
<Preparation of DNA (A)>
The DNA (A) was a circular monomeric DNA plasmid with redundancy of r=1. First, *Escherichia coli* was transformed with pGETS118-t0-Pr-SfiI-pBR. Most of the plasmids obtained from the resulting transformant were the DNA (A), but a small amount of multimers were also contained. In order to remove the multimers, all the plasmids obtained were subjected to electrophoresis in agarose gel with low melting temperature for DNA-size-based selection, and only the monomeric DNA plasmid region was cut out from the gel and purified. Thus, the DNA (A) was prepared.
<Preparation of DNA (B)>
The DNA (B) was a linear monomeric DNA plasmid with redundancy of r=1. The DNA (B) was prepared by treating the DNA (A) with the restriction enzyme BlpI (the recognition site thereof was (5'-GC/TNAGC-3')).
<Preparation of DNA (C)>
The DNA (C) was a tandem-repeat linear multimeric DNA plasmid with redundancy of r>1. BlpI used for preparing the DNA (B) above formed a 3-base non-palindromic protruding sequence at the 5' end. Accordingly, by joining molecules of the DNA (B) to each other with DNA ligase, a continuous linear multimeric DNA plasmid having its plasmid units arranged in a certain orientation was prepared, which was the DNA (C).
<Preparation of DNA (D)>
The DNA (D) was a linear monomeric DNA plasmid with redundancy of r=1. The DNA (D) was prepared by treating the DNA (A) with the restriction enzyme EcoRI (the recognition site thereof was (5'-G/AATTC-3')).
<Preparation of DNA (E)>
The DNA (E) was a linear multimeric DNA plasmid including a portion with partially redundancy of r>1 and composed of molecules of the DNA (D) joined together in a random orientation. EcoRI used for preparing the DNA (D) above formed a 3-base palindromic protruding sequence at the 5' end. Accordingly, by joining DNA plasmids that were cleaved with EcoRI, it was possible to construct a multimeric DNA plasmid having its plasmid units joined in a random orientation. The DNA (E) was prepared by joining molecules of the DNA (D) above to each other with DNA ligase.
<Preparation of DNA (F)>
The DNA (F) was a linear semi-monomeric mixture with r≈1. The DNA (F) was prepared as follows: the DNA (A) was cleaved only at a single site with the restriction enzyme KasI, dephosphorylated, and then cleaved with BlpI at a site near the above-cleaved site to give a DNA fragment; the DNA (A) was cleaved only at a single site with the restriction enzyme AfeI, dephosphorylated, and then cleaved with BlpI at a site near the above-cleaved site to give a DNA fragment; and mixing both of these resulting DNA fragments in equal amount. Each of the DNA fragments in the mixture (F) had redundancy r which is slightly lower than 1.
<Preparation of DNA (G)>
The DNA (G) was a linear semi-dimer DNA plasmid with redundancy of r=1.98. The DNA (G) was prepared by joining 2 DNA fragments (F) above with DNA ligase, and the orientation therein was regulated by its BlpI sites alone.
<Preparation of DNA (H)>
The cleavage site in the DNA (B) and the cleavage site in the DNA (D) were away from each other. The DNA (H) was a mixture prepared by not joining but mixing the DNA (B) and the DNA (D) in equal number of moles.
<Transformation of *Bacillus subtilis* Competent Cell with DNA (A) to DNA (H)>
A *Bacillus subtilis* competent cell was transformed with each of the DNA (A) to the DNA (H). Based on the appearance number of the tetracycline-resistant strains as index, the number of transformants per 1 μg was determined Each of the DNA (A) to the DNA (H) for use in transformation was dissolved in ligation buffer regardless of whether the DNA was to be subjected to ligation reaction. FIG. 17 is a photograph showing the result of electrophoresis analyzing the DNA (A) to the DNA (H), and FIG. 18 shows the appearance number of transformants obtained by transformation of *Bacillus subtilis* competent cell with the DNA (A) to the DNA (H). It is noted that in the photograph of electrophoresis in FIG. 17, the lanes of the DNA (C) and the DNA (E) had DNA molecules of various sizes widely distributed across each lane, making the bands difficult to distinguish. As for the lane "G" in FIG. 17, the upper band was attributed to the DNA (G) with redundancy of r=1.97, and the lower band was attributed to DNA with redundancy of r=0.95 as a contaminant in the DNA (G).

It was confirmed that these results showed that transformants were obtained only with the ligation, namely, the DNA (C), the DNA (E), and the DNA (G), with the circular DNA (A) not counted. As indicated by these results, no transformant would be obtained with redundancy being r=1 or r<1 even when the DNA molecule was prepared by mixing 2 kinds of linear plasmid molecules having different cleavage sites that would be able to compensate for each other. As a result, it was indicated that redundancy of a linear DNA molecule needed to satisfy r>1 at lowest.

(Simulation 1, Ligation Simulation)
<Setting Algorithm for Ligation Simulation>

Simulation was programmed on VBA of spreadsheet software Excel® 2007. The DNA fragment F used in virtual ligation was expressed as 3 parameters, Fi(Ni, Li, Ri). "i" referred to the identification number of the fragment, more specifically the number on the cell in the row i on Excel. "N" referred to the number of DNA unit fragments in a single ligation DNA fragment molecule in virtual ligation. "L" referred to an arbitrary natural number that represented the sequence of the left protruding end of the ligation product. Similarly to "L", "R" referred to an arbitrary natural number that represented the sequence of the right protruding end of the ligation product. When L=R, the 2 protruding sequences were complementary to each other. Therefore, the relationship L=R defines that ligation was eligible to occur. Ligation simulation was conducted as follows.

The random number j that satisfied i≠j was obtained by generating a uniform random number between 0 and 1 by the RAND ( ) method, multiplying the resulting number by m (described below), and rounding off the resulting number to give an integer. This resulting integer was applied to the fragment Fi(Ni, Li, Ri) to give the fragment Fj(Nj, Lj, Rj). Whether these 2 fragments were to be successfully joined together was determined according to the following discrimination formulae, and when they were to be successfully joined together, the parameters of these fragments were converted as follows.

When Li=Rj was satisfied, in other words, when the left end of Fi and the right end of Fj were to be successfully joined together, conversion was made to give the fragment Fi(new)(Ni(old)+Nj(old), Lj(old), Ri(old)) and the fragment Fj(new)(0, 0, 0). In contrast, when Ri=Lj was satisfied, in other words, when the right end of the fragment Fi and the left end of the fragment Fj were to be successfully joined together, conversion was made to give the fragment Fi(new)(Ni(old)+Nj(old), Li(old), Rj(old)) and the fragment Fj(new)(0, 0, 0). When Li≠Rj and Ri≠Lj were satisfied, no conversion was made (giving (the fragment Fi(new)(Ni(old), Li(old), Ri(old)) and the fragment Fj(new)(Nj(old), Lj(old), Rj(old))), where no virtual ligation was to occur. The same calculation conducted sequentially with i=1→m was defined as 1 cycle of virtual ligation. Here, the variable m referred to the total number of DNA fragments in the virtual ligation cycles, and for the 1st simulation cycle, the variable m referred to the total number of DNA unit fragments to start with. After calculation for the 1st cycle of virtual ligation, calculation for the next cycle of virtual ligation was conducted by rearranging the fragments Fi by the sorting function (the Sort method) in the VBA command of Excel 2007 so that the values Li were arranged in descending order, counting the total number of the fragments Fi except for the fragment F(0, 0, 0), and using the resulting total number as a variable m for the new cycle. Virtual ligation was repeated until the number of fragments reached the minimum mmin where there were no more protruding fragments complementary to each other and therefore no more cycle of virtual ligation was possibly conducted. The value mmin was determined according to the following calculation based on data about the starting DNA unit fragments, namely, the pre-ligation DNA unit fragments.

mmin=(total number of DNA unit fragments)−(total number, across entire system, of 1 out of 2 kinds of DNA unit fragments both satisfying L=R, that was fewer than the other)

<Ligation Simulation>

Virtual DNA unit fragment groups each of which consisted of 6 fragments, 13 fragments, 26 fragments, or 51 fragments assembled together were formed as follows. The virtual DNA unit fragment groups contained a fixed number, 640, of DNA unit fragments on average, and had a coefficient of variation (CV) that was set to increase sequentially by 1% from 0% to 20%.

The virtual DNA unit fragment groups were formed respectively by generating a group of random numbers from 0 to 1 corresponding to each assembly size by the uniform random number command RAND ( ) of Excel, standardizing the group of random numbers with average value of 0 and variance of 1, multiplying each standardized random number by (fragment average value*CV(%)/100), and adding the average value of fragments to the resulting number. For each assembly size, independent 20 groups of random numbers were constructed each for one of the CV (%) values. Each of these groups of random numbers underwent virtual ligation by the simulation, which was conducted until mmin was reached. The resulting 20 virtual ligation fragments were combined together, and the total number of ligation fragments for each N value was obtained. The ratio of (N value×number of ligation fragments) to the total number of DNA unit fragments used in ligation was determined. A 100-% stacked graph was created such that the value attributed to a molecule with a higher N value was plotted lower in the graph. Such graphs are shown in FIG. 19. FIG. 19 shows distribution of the sizes of ligation products to which the starting DNA unit fragments were eventually taken up. FIG. 19A is a graph for the 6-fragment assembly, FIG. 19B is a graph for the 13-fragment assembly, FIG. 19C is a graph for the 26-fragment assembly, and FIG. 19D is a graph for the 51-fragment assembly. In the case of the 6-fragment assembly, redundancy of r=1 region was reached at n=6 and the upper right region indicated where redundancy satisfied r<1. These results showed that: in the case of the 6-fragment assembly, most DNA unit fragments were taken up by DNA fragments that had redundancy of r>1, at any CV value; and, in contrast, in the case of the 51-fragment assembly, redundancy was lower than 1 in most of the region except for the region where CV was near 0%.

<Obtaining Theoretical Formula for Ligation from Ligation Simulation>

Figure 20:
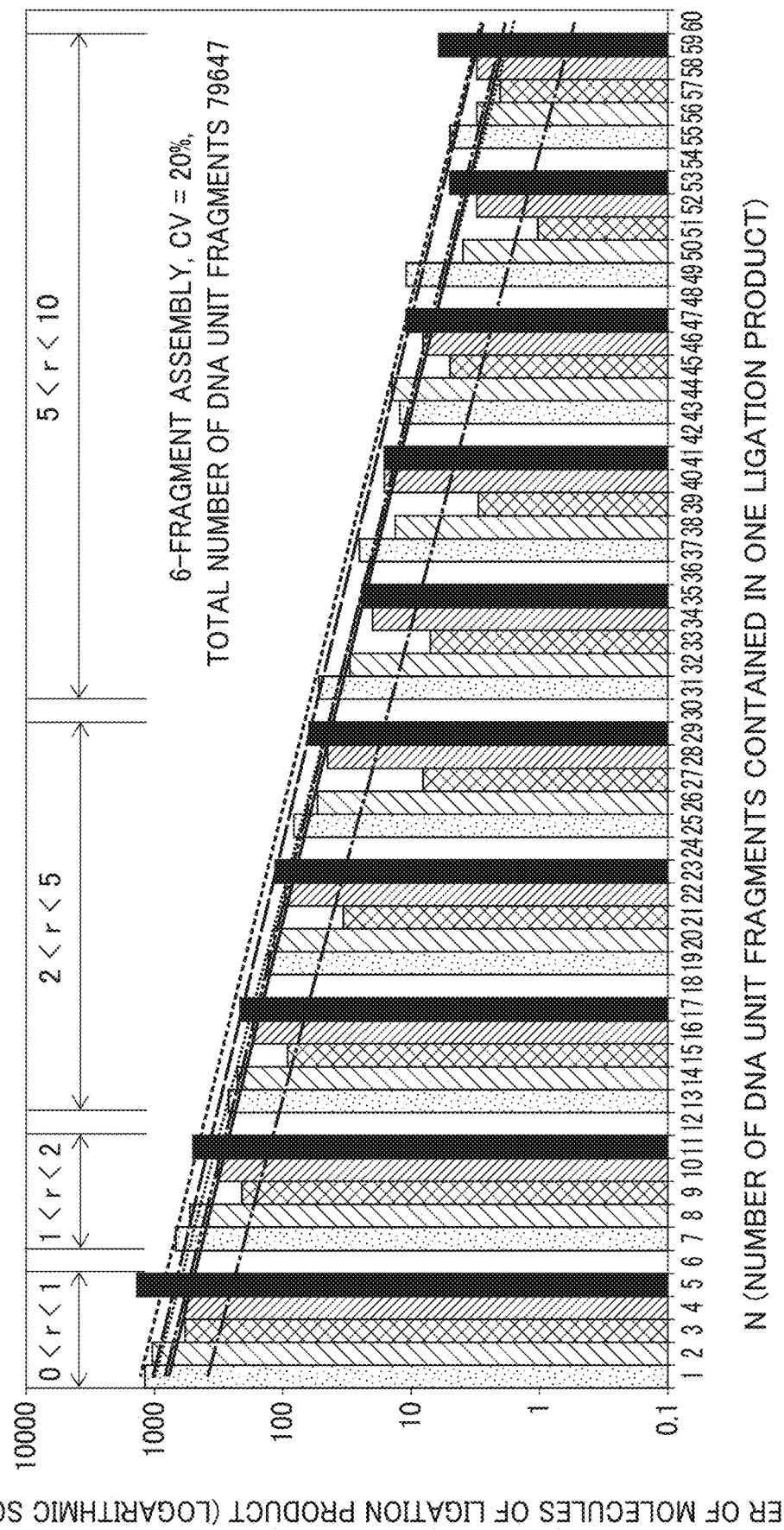
FIG. 20 a graph showing the relationship between N (the number of DNA unit fragments in one ligation product) and the number of molecules of ligation products, analyzed for a 6-fragment assembly in simulation 1 with CV=20%.

The results of the ligation simulation were numerically analyzed in order to obtain a general formula for the ligation mechanism. First, whether it was possible to plot a fitting curve for the distribution of the sizes of ligation products for each CV value for each assembly size was evaluated. FIG. 20 is a diagram for the case of the 6-fragment assembly comprising 640 fragments on average, and it shows distribution of the number of DNA unit fragments contained in a ligation product at CV=20%. In FIG. 20, different patterns that filled the rectangles drawn for the same redundancy (0<r<1, 1<r<2, 2<r<5, or 5<r<10) indicated the different components generated by dividing N for each pattern by r for each redundancy range (5 components in the case of the 6-fragment assembly, calculated by subtracting 1 component that gave a reminder of 0 when dividing N by r and therefore was not eligible for logarithmic transformation, from 6 components each of which gave a remainder of 0, 1, 2, 3, 4, or 5). Rectangles with the same pattern across different redundancy ranges were attributed to the same kind of component generated by dividing N value by r. Each linear approximation curve in the diagram shown in FIG. 20 was plotted for components that shared the same pattern.

The number of molecules contained in a ligation product for each N value shown in the histogram had a general tendency to exponentially decrease as N value increased, and appeared to be close to geometric distribution, which was one type of discrete probability distribution. Microscopically, however, the histogram displayed a periodic model consisting of cycles each of the size of the gene assembly, namely, the size of one redundancy unit (6 in the case of the 6-fragment assembly). The histogram displayed a characteristic pattern where no fragment occurred for N value being equal to an integral multiple of the size of the gene assembly. This particular characteristic was not in complete agreement with geometric distribution or with exponential distribution regarded as continuous probability distribution. However, when converting the axis that showed the number of molecules in a ligation product into logarithmic expression, selecting and taking out, from each cycle, the components that constituted the same microscopic cycle, in other words, the components that gave the same remainder when N was divided by 6 or the size of the assembly, and plotting a linear approximation curve, the resulting linear approximation curve had the second power of a very high correlation coefficient (0.94 or greater). Therefore, it was considered that there was no problem when a linear approximation curve created for each component displayed exponential distribution. The same distribution as displayed by the case of the 6-fragment assembly where CV value as variation in the concentration was 20%, shown in FIG. 20, was also observed for other assembly sizes and other CVs. Thus, based on the assumption that this mechanism was eligible to be heuristically approximated to exponential distribution, fitting to exponential distribution function ($f(n)=\lambda^* \exp(-\lambda^* n)$) was conducted hereinafter.

Figure 21B:
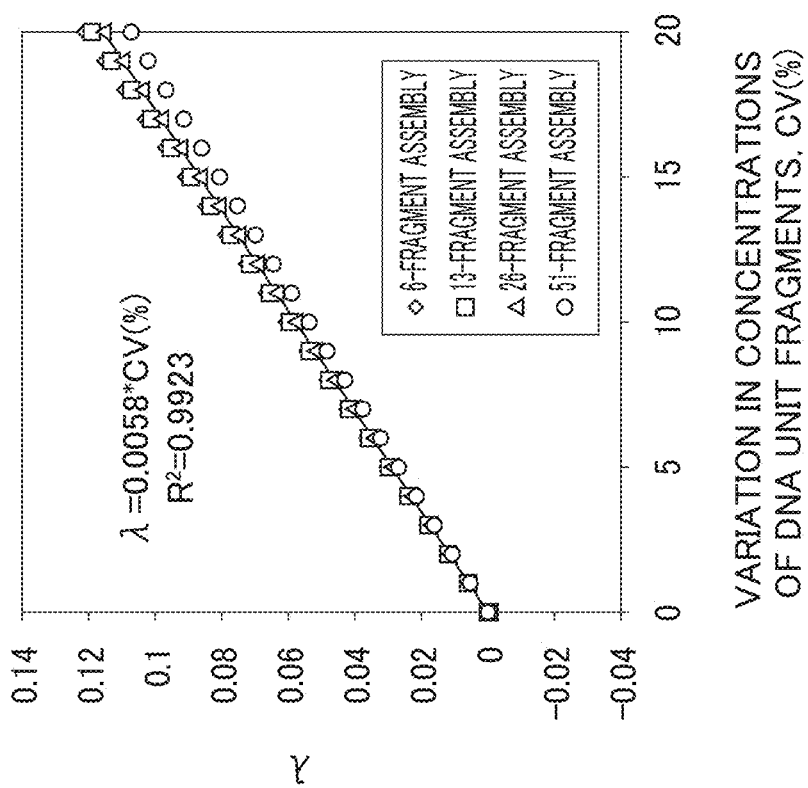
FIG. 21B is a graph showing λ function of CV (%) indicating variation in the concentrations of DNA unit fragments determined from the average N value of virtual ligation product.
Figure 21A:
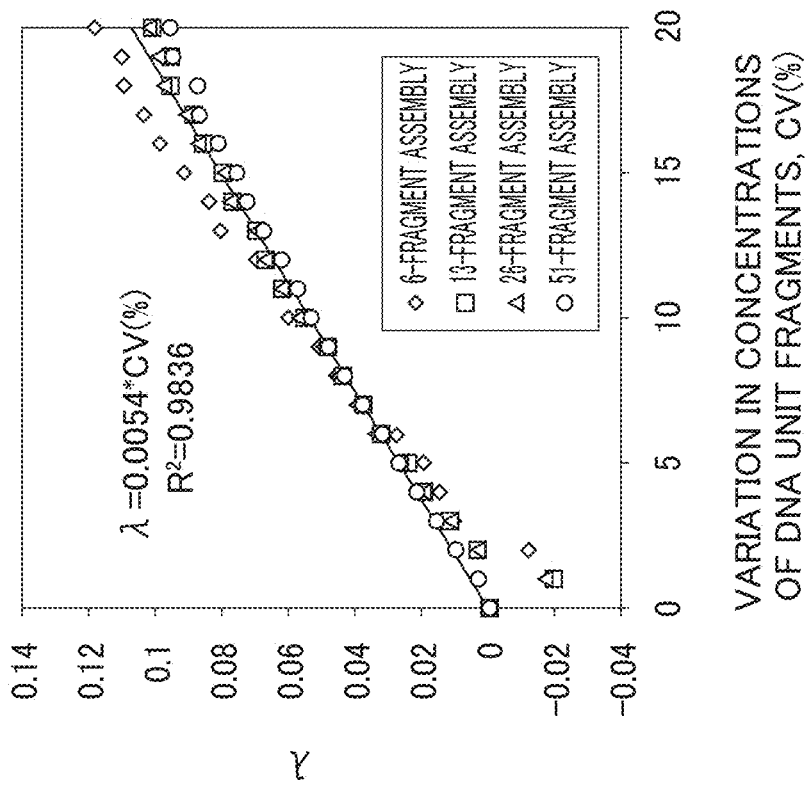

Specific procedure was as follows: (1) in the results of simulation conducted for each assembly size described above, the number of molecules for about 3 cycles as for each of the components that gave the same remainder when N was divided by the size of the assembly was subjected to logarithmic transformation, and the resulting values were used to create a linear approximation curve, followed by determining the slope ($-\lambda$) of the straight line and calculating the value $\lambda$;

and (2) next, in consideration that the average value of $f(N)$ in the exponential distribution function was the reciprocal of the parameter $\lambda$, namely, $1/\lambda$, the average value of N of ligation products for the 20 groups of random numbers was determined, and the reciprocal of the resulting average value was used to determine $\lambda$ for each CV (%) (CV (%)). The results of (1) and (2) were plotted, with setting the abscissa showing the CV (%) value of variation of concentrations of DNA unit fragments and the ordinate showing the $\lambda$ value. As a result, it was shown that all the plottings for each size of the gene assembly were on a direct proportional straight line passing through a certain original point. A linear approximation curve was determined for each set of these plottings, as shown in FIG. 21. In FIG. 21, A is a graph showing the relationship between the slope $\lambda$ determined for the 3 cycles in (1) and variation in the concentrations of DNA unit fragments, and B is a graph showing the relationship between $\lambda$ determined from the reciprocal of the average N value in (2) and variation in the concentrations of DNA unit fragments. From (2) with higher accuracy, the general formula of these linear approximation curves was derived: $f(N)=0.0058^*CV(\%)^* \exp(-0.0058CV(\%)^*N)$. From FIG. 21, it was found that the second power of correlation coefficient of $\lambda=0.0058^*CV(\%)$ was expressed as 0.99, indicating high correlation. Thus, this general formula was confirmed to have no problem.

<Qualitative Analysis of Reaction Rate of Ligation>

The ligation simulation described above was intended to represent a state where ligation between all reasonable protruding-end combinations had been fully completed. Here, in order to examine how close the ligation reaction conditions in actual gene assembly were to reaction conditions in simulation, the kinetics of ligation reaction were analyzed.

First, in ligation reaction conducted under the conditions in actual gene assembly, samples of the ligation products were taken at various reaction times. A 51-fragment concatemer for $\lambda$ phage reconstruction was used, and all the 51 joints were qualitatively analyzed to evaluate the degree of actual joining. The average concentration of the DNA unit fragments used in ligation was about 0.2 fmol/µl. To the DNA unit fragment solution, T4 DNA ligase was added. After 0 minute, 1.25 minutes, 2.5 minutes, 5 minutes, 10 minutes, 20 minutes, 40 minutes, 80 minutes, 160 minutes, and 320 minutes at 37° C., a sample of each reaction solution was taken. Then the progress of ligation of each fragment was evaluated using a primer set for quantitative PCR designed to amplify DNA stretching across the joint between 2 DNA unit fragments being reasonably joined, a primer set for quantitative PCR designed to amplify only inside each DNA unit fragment, and, as an indicator, the dilution series of DNA that was produced by cleaving with a restriction enzyme a commercially available $\lambda$ phage genomic DNA (Toyobo Co., Ltd.) or an assembly-harboring plasmid constructed in advance and then rendering the resulting DNA fragment linear. The results showed that ligation had been completed in about 10 minutes at any joint under these reaction conditions, indicating that ligation would be substantially fully completed in the actual reaction time of 4 hours (240 minutes). The results also showed that the ratio of the number of joints after sufficient time (after 40 minutes) to the number of the kind of the DNA unit fragments that was fewer than the other was substantially 1, indicating that most of the ligated DNA fragments joined to their correct ligation partners.

<Estimation of Misligation Rate>

Figure 22:
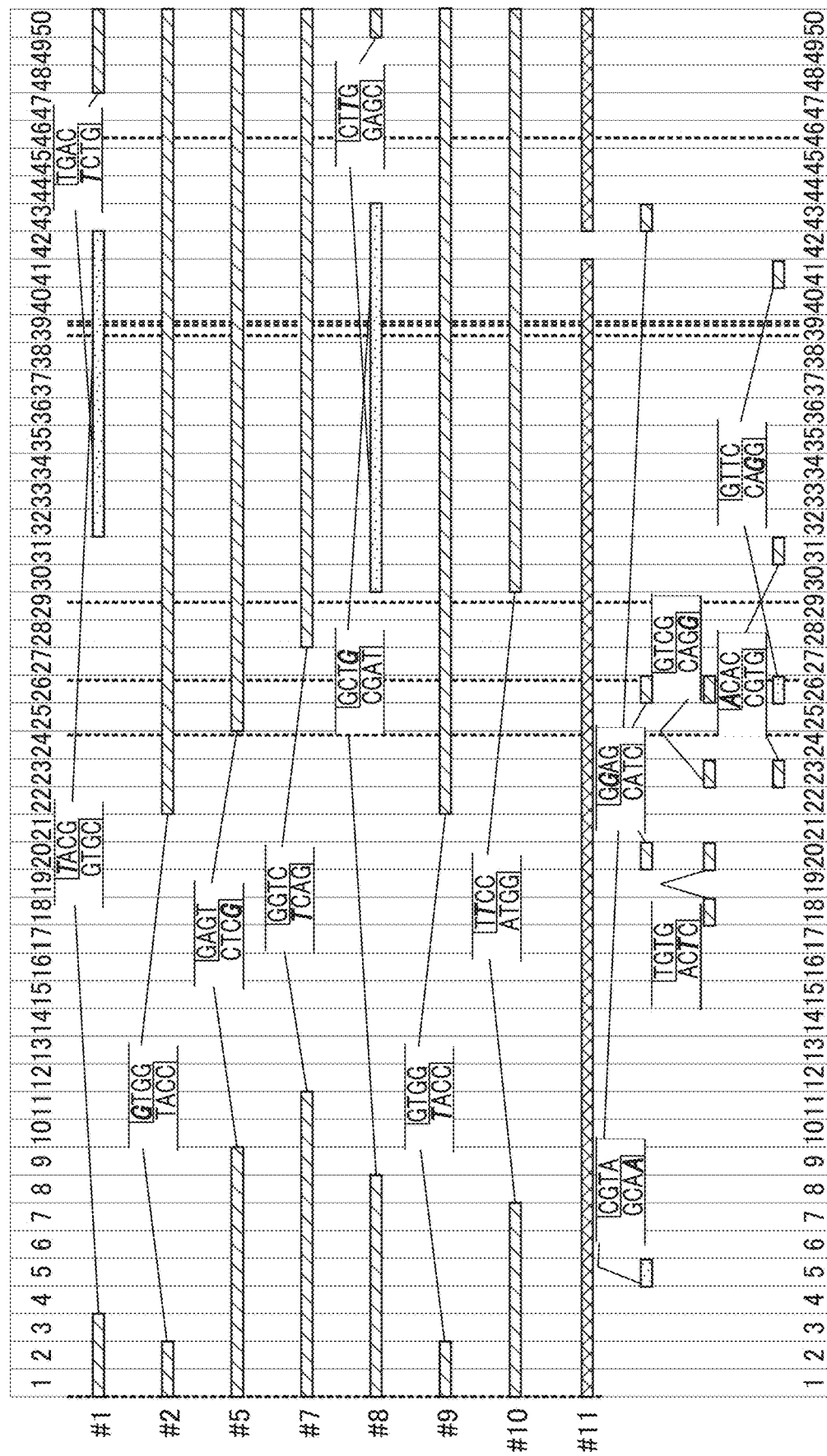
FIG. 22 an illustration showing misligation sites in assemblies #1, #2, #5, #7, #8, #9, #10, and #11 among assemblies resulting from experiment of reconstruction of X phage genome in simulation 1.

The state of ligation was studied in more detail. Among the assemblies obtained in the experiment above of reconstruction of $\lambda$ phage genome, all the clones except for clones #3, #4, #6, and #12 with their entire base sequences completely determined (namely, clones #1, #2, #5, #7, #8, #9, #10, and #11) were subjected to base sequencing in order to identify ligation site between a wrong combination. FIG. 22 shows misligation sites for each of these clones. The results showed that each of the 7 clones except for the clone #11 had 1 or 2 misligation sites within the sequence, and all of these misligation sites were successfully identified. The clone #11 had the same DNA unit fragments occurring repeatedly within the DNA assembly and was found to have 6 misligation sites in total. No thorough structural identification was conducted. As for all the clones except for the clone #11 with its accurate number of DNA unit fragments unknown, the appearance frequency of misligation was determined. As a result, the rate of misligation was found to be about 1 in 46 joints, which was equal to a relatively low rate of misligation of about 2.2%. These results were in agreement with the results from quantitative PCR above.

<Distribution of Sizes of Actual Ligation Products, and Verification of Agreement with Simulation>

From these two analyses described above, namely, estimation of the misligation rate and qualitative analysis of reaction rate of ligation, it was presumed that ligation would be substantially fully completed in actual ligation reaction after a sufficient amount of time of 4 hours and that the probability of misligation was low. Then, as for actual DNA unit fragment groups with variation occurring in the concentration of the starting DNA unit fragments, whether distribution of the sizes of actual ligation products was predictable by simulation was studied, as follows.

Figure 23:
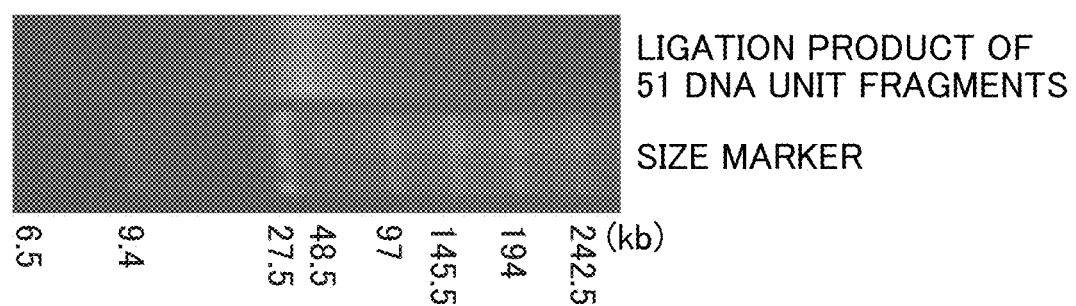
FIG. 23 a photograph showing the result of pulsed-field gel electrophoresis analyzing the product of ligation of 51 DNA unit fragments with CV=6.6% variation in the number of fragments in experiment of reconstruction of X phage genome in simulation 1.
Figure 24A:
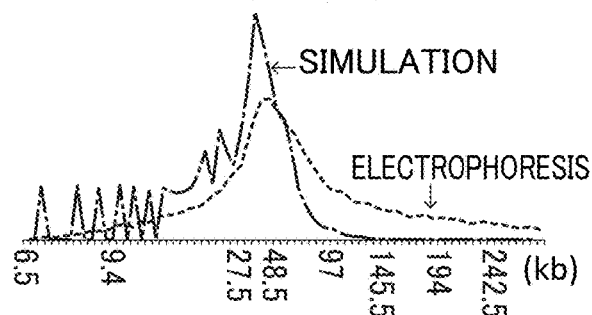
FIG. 24A is a graph comparing with simulation with a ligation-eligible rate of 95%.
Figure 24D:
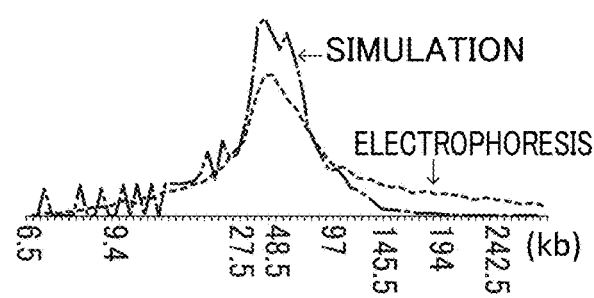
FIG. 24D is a graph comparing with simulation with a ligation-eligible rate of 98%.
Figure 24B:
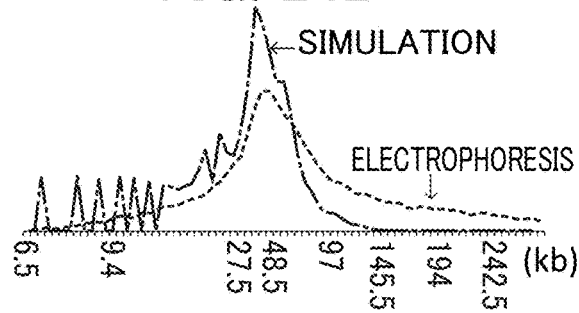
FIG. 24B is a graph comparing with simulation with a ligation-eligible rate of 96%.
Figure 24E:
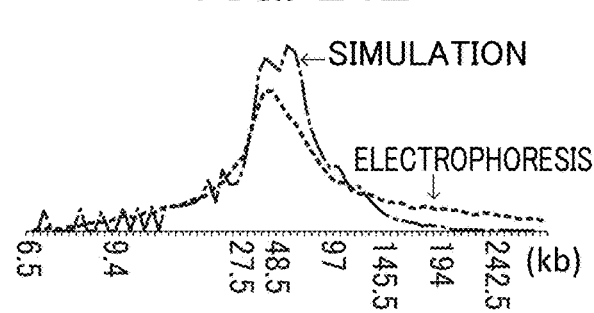
FIG. 24E is a graph comparing with simulation with a ligation-eligible rate of 99%.
Figure 24C:
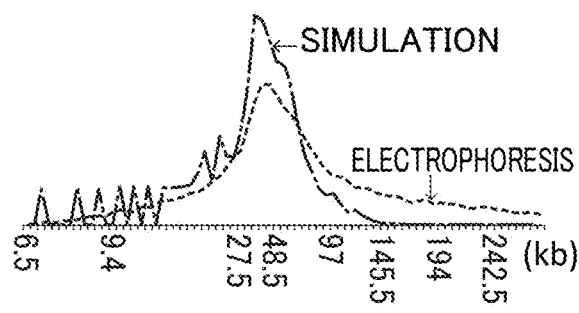
FIG. 24C is a graph comparing with simulation with a ligation-eligible rate of 97%.
Figure 24F:
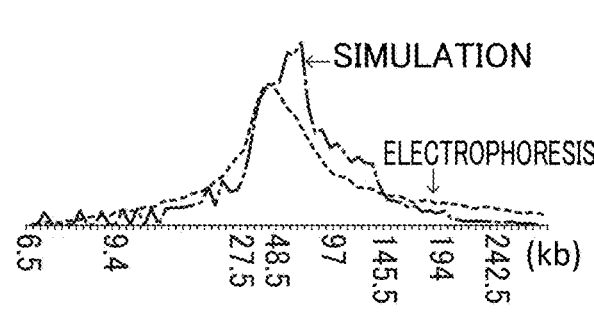
FIG. 24F is a graph comparing with simulation with a ligation-eligible rate of 100%.

Analysis was conducted on the groups used in the experiment of reconstruction of λ phage genome. The groups had variation in the concentrations of DNA unit fragments with 7.5% of CV as observed by quantitative PCR. An observed value resulting from quantitative PCR involved measurement errors of CV=3.6%. Therefore, the true CV value for DNA unit fragment variation was presumably and possibly lower than CV=7.5%. Simulation was conducted to determine a CV value that was potentially the true CV value. As a result, when the true CV value was 6.6%, the observed value was presumably and possibly CV=7.5% due to measurement errors of CV=3.6%. In consideration of the true DNA unit fragment variation being CV=6.6%, simulation was conducted so as to simulate ligation of 51 kinds of starting DNA unit fragments under conditions of average 640 fragments prepared for the RAND ( ) method and CV=6.6%. The simulation reaction was conducted until not only mmin indicating 100% reaction rate was reached but also a designated m value was reached. The designated m value was obtained by determining m values for ligation-eligible rates of 95%, 96%, 97%, 98%, and 99% ligation, preparing 100 independent groups of random numbers for each m value, and determining the designated m value. The distribution patterns of obtained ligation products displayed by these 100 groups were combined together, and the length (bp) of DNA of each virtual ligation product of DNA unit fragments was determined by using the parameters F(N, L, R). Then, the actual DNA unit fragment groups used in experiment of reconstruction of λ phage genome with variation in the number of fragments of CV=6.6% were, as described in the paragraph "Qualitative analysis of reaction rate of ligation" above, subjected to reaction at 37° C. for 4 hours, followed by electrophoresis on a CHEF-type pulsed-field gel electrophoresis system (manufactured by Bio Craft Co., Ltd.) for 16 hours under electrophoresis conditions of 0.5× TBE, 5 V/cm, and 30 sec per cycle, in order to see the actual distribution of the molecular weight of DNA. FIG. 23 is a photograph showing the result of the electrophoresis. From the resulting electrophoresis photograph, a DNA density distribution pattern was acquired on NIH image software, and the pattern thus acquired was overlaid with expected DNA distribution patterns obtained for each ligation efficiency determined from simulation, for comparison. The results are shown in FIG. 24. FIG. 24 showed that the distribution pattern of the molecular weight of DNA resulting from the electrophoresis was in near agreement with the expected DNA distribution patterns for ligation efficiency from 98% to 100%. In particular, the maximum molecular weight indicating the maximum concentration was in excellent agreement with the expected DNA distribution pattern for ligation efficiency of 98%. These simulation results showed that ligation was substantially fully completed within 4 hours of ligation reaction and simulation was able to nearly perfectly reproduce ligation with mere misligation of about 2%.

<Generalization of Ligation Simulation>

Figure 25:
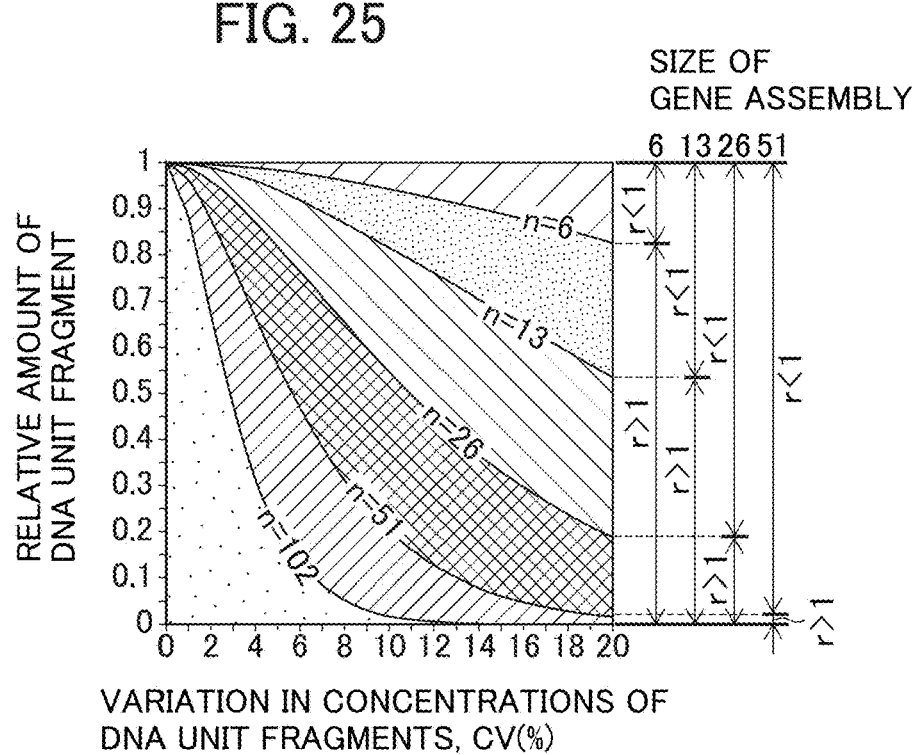
FIG. 25 a graph showing the relationship between CV (%) indicating variation in the concentrations of DNA unit fragments and the relative amount of each kind of DNA unit fragment, obtained by using the formula $f(N)=0.0058*CV(\%)*\exp(-0.058*CV(\%)*N)$. The analysis was conducted for each gene assembly size in simulation 1.
Figure 26:
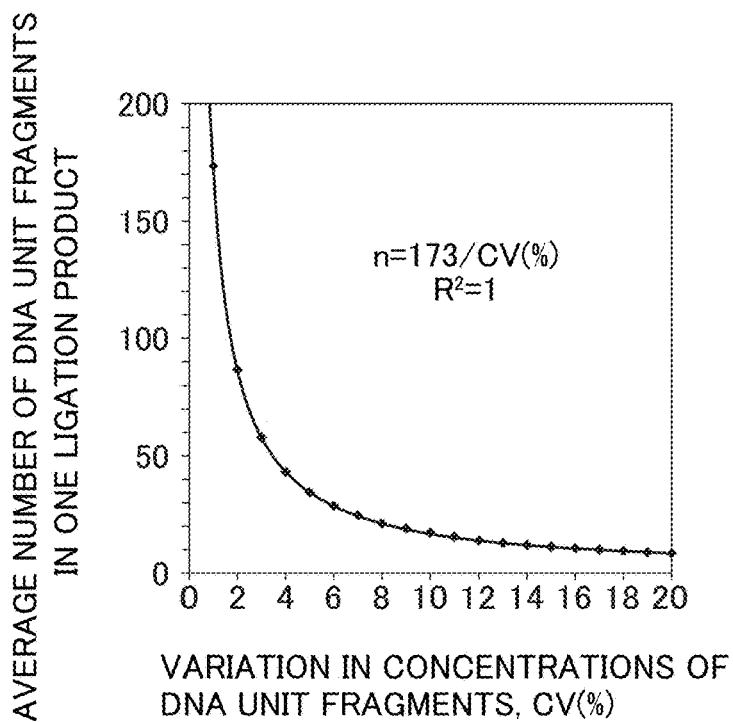
FIG. 26 a graph showing the relationship between variation in the concentrations of DNA unit fragments and the average number of DNA unit fragments in one ligation product, obtained by using the formula $f(N)=0.0058*CV(\%)*\exp(-0.0058*CV(\%)*N)$.

DNA unit fragments used in actual assembly cannot be free from variation in the concentration. How well actual variation in the concentrations of DNA unit fragments needed to be regulated was summarized based on the general formula $f(N)=0.0058*CV(\%)*exp(-0.0058*CV(\%)*N)$ determined above, and was shown in FIG. 25. Although variation in DNA concentration was approximately CV(%)= 6.6 in the gene-assembling experiment above, FIG. 25 shows that, when CV(%)=6.6, about 40% of the DNA unit fragments used in the 51-fragment assembly was taken up by a ligation product with an r value of greater than 1. FIG. 25 also shows that, when a novel 102-fragment gene assembly, twice the size of the 51-fragment assembly, is designed, it is necessary to achieve CV(%)=3.3 in order to obtain the same level of assembly efficiency as for the 51-fragment assembly. By the formula $f(N)=0.0058*CV(\%)*exp(-0.0058*CV(\%)*N)$, the relationship between variation in the concentrations of DNA unit fragments and the average number of DNA unit fragments in one ligation product was determined. The results are shown in FIG. 26. It was shown that, the formula $f(N)=0.0058*CV(\%)*exp(-0.0058*CV(\%)*N)$ made it possible to easily presume the average number of DNA unit fragments contained in one ligation product with a CV (%) value.

[Sequence Listing]

The invention claimed is:

1. A method of preparing a DNA unit fragment composition, comprising:
a step of preparing solutions containing multiple kinds of DNA unit fragments, each solution containing one of the multiple kinds of DNA unit fragments, each DNA unit fragment being attached to a corresponding auxiliary sequence; and
a step of, after preparing each solution, measuring the concentration of each kind of DNA unit fragment with the corresponding auxiliary sequence attached thereto in each of the solutions, and then based on the measurement result, taking a portion from each of the solutions so that the number of moles of DNA unit fragment in one portion is the same as the number of moles of DNA unit fragment in another portion, and combining each of the portions to prepare the DNA unit fragment composition.

2. The method of preparing a DNA unit fragment composition according to claim 1, wherein each DNA unit fragment with the corresponding auxiliary sequence attached thereto has a circular structure, and each corresponding auxiliary sequence is a plasmid DNA sequence harboring an origin of replication.

3. The method of preparing a DNA unit fragment composition according to claim 1, wherein a standard deviation of the sum of the length of the base sequence of each DNA unit fragment and the length of the base sequence of the corresponding auxiliary sequence attached to the DNA unit fragment is −20% to within 20% plus or minus the average value of the sum of the lengths.

4. The method of preparing a DNA unit fragment composition according to claim 1, wherein the average length of the base sequence of the corresponding auxiliary sequence attached to each DNA unit fragment is twice or greater than the average length of the base sequence of the DNA unit fragment.

5. The method of preparing a DNA unit fragment composition according to claim 1, wherein each DNA unit fragment is not longer than 1600 bp.

6. The method of preparing a DNA unit fragment composition according to claim 1, wherein
the DNA unit fragments are used to construct a DNA concatemer, the DNA concatemer comprising DNA assemblies each comprising the DNA unit fragments, and
the step of preparing solutions containing multiple kinds of DNA unit fragments comprises a step of designing of DNA unit fragment, the designing being conducted in a way that in the base sequence of each DNA assembly a non-palindromic sequence is present near each boundary between two adjacent DNA unit fragments, and each DNA unit fragment has the non-palindromic sequence at an end and is separated by the non-palindromic sequence from an adjacent DNA unit fragment.

7. A method of constructing a DNA concatemer to be used for microbial cell transformation, the DNA concatemer comprising more than one DNA assembly unit, each of the more than one DNA assembly unit comprising a DNA vector harboring an origin of replication effective in a host microorganism and a DNA assembly, the method comprising:
a step of preparing a DNA unit fragment composition in a solution by the method as claimed in claim 1;
a step of preparing the DNA vector;
a step of removing with a restriction enzyme a corresponding auxiliary sequence from each DNA unit fragment with the corresponding auxiliary sequence attached thereto contained in the solution after preparation; and
a step of, after the removal step, joining the DNA vector and each of the DNA unit fragment together,
wherein
each of the DNA vector and the DNA unit fragment is structurally capable of being joined repeatedly while maintaining a certain order, and
each DNA assembly comprises of a DNA molecule in which the DNA unit fragment is joined to one another.

8. The method of constructing a DNA concatemer according to claim 7, further comprising:
a step of, adjusting a coefficient of variation for the concentrations of the DNA vector and each DNA unit fragment in the combining step based on a relation between a yield of a DNA fragment comprising a target number of DNA unit fragments joined together and a coefficient of variation for the concentration of this DNA fragment, the yield being equal to the product of the number of DNA unit fragments per assembly unit and the number of the assembly unit.

9. The method of constructing a DNA concatemer according to claim 7, wherein the restriction enzyme is a Type II restriction enzyme.

10. The method of constructing a DNA concatemer according to claim 7, further comprising:
a step of, before the removal step, mixing two or more solutions containing DNA unit fragments selected from the solutions containing DNA unit fragments.

11. The method of constructing a DNA concatemer according to claim 7, further comprising:
a step of, after the removal step and before the joining step, inactivating the restriction enzyme.

12. The method of constructing a DNA concatemer according to claim 7, wherein the microorganism is *Bacillus subtilis*.

13. The method of claim 1, wherein a molar ratio among each of the different portions is 1.

* * * * *

```
                        SEQUENCE LISTING

<160> NUMBER OF SEQ ID NOS: 65

<210> SEQ ID NO 1
<211> LENGTH: 17749
<212> TYPE: DNA
<213> ORGANISM: Artificial Sequence
<220> FEATURE:
<223> OTHER INFORMATION: Artificial plasmid

<400> SEQUENCE: 1
gcggccgcaa gcttgaagag ctcttctttc agaacgctcg gttgccgccg ggcgtttttt      60
atgagacgtc tcggcctgtt tggccattaa cgtgcaggtg gatccagatc taagcttcta     120
tagaagcttg gtaccgacgt ctcggcctgt ttggcccgcc gcatccatac cgccagttgt     180
ttaccctcac aacgttccag taaccgggca tgttcatcat cagtaacccg tatcgtgagc     240
```

-continued

```
atcctctctc gtttcatcgg tatcattacc cccatgaaca gaaatccccc ttacacggag    300
gcatcagtga ccaaacagga aaaaaccgcc cttaacatgg cccgctttat cagaagccag    360
acattaacgc ttctggagaa actcaacgag ctggacgcgg atgaacaggc agacatctgt    420
gaatcgcttc acgaccacgc tgatgagctt taccgcagct gcctcgcgcg tttcggtgat    480
gacggtgaaa acctctgaca catgcagctc ccgaagacgg tcacagcttg tctgtaagcg    540
gatgccggga gcagacaagc ccgtcagggc gcgtcagcgg gtgttggcgg gtgtcggggc    600
gcagccatga cccagtcacg tagcgatagc ggagtgtata ctggcttaac tatgcggcat    660
cagagcagat tgtactgaga gtgcaccata tgcggtgtga ataccgcac agatgcgtaa    720 ggagaaaata ccgcatcagg cactcttccg cttcctcgct cactgactcg ctgcgctcgg    780
tcgttcggct gcggcgagcg gtatcagctc actcaaaggc ggtaatacgg ttatccacag    840
aatcagggga taacgcagga agaacatgt gagcaaaagg ccagcaaaag gccaggaacc    900
gtaaaaaggc cgcgttgctg gcgttttttcc ataggctccg ccccctgac gagcatcaca    960 aaaatcgacg ctcaagtcag aggtggcgaa acccgacagg actataaaga taccaggcgt   1020
ttccccctgg aagctccctc gtgcgctctc ctgttccgac cctgccgctt accggatacc   1080
tgtccgcctt tctcccttcg ggaagcgtgg cgctttctca tagctcacgc tgtaggtatc   1140
tcagttcggt gtaggtcgtt cgctccaagc tgggctgtgt gcacgaaccc cccgttcagc   1200
ccgaccgctg cgccttatcc ggtaactatc gtcttgagtc caacccggta agacacgact   1260
tatcgccact ggcagcagcc actggtaaca ggattagcag agcgaggtat gtaggcggtg   1320
ctacagagtt cttgaagtgg tggcctaact acggctacac tagaaggaca gtatttggta   1380
tctgcgctct gctgaagcca gttaccttcg gaaaaagagt tggtagctct tgatccggca   1440
aacaaaccac cgctggtagc ggtggttttt tgtttgcaa gcagcagatt acgcgcagaa   1500
aaaaaggatc tcaagaagat cctttgatct tttctacggg gtctgacgct cagtggaacg   1560
aaaactcacg ttaagggatt ttggtcatga gattatcaaa aaggatcttc acctagatcc   1620
ttttaaatta aaaatgaagt tttaaatcaa tctaaagtat atatgagtaa acttggtctg   1680
acagttacca atgcttaatc agtgaggcac ctatctcagc gatctgtcta tttcgttcat   1740
ccatagttgc ctgactcccc gtcgtgtaga taactacgat acgggagggc ttaccatctg   1800
gccccagtgc tgcaatgata ccgcgagacc cacgctcacc ggctccagat ttatcagcaa   1860
taaaccagcc agccggaagg gccgagcgca gaagtggtcc tgcaacttta tccgcctcca   1920
tccagtctat taattgttgc cgggaagcta gagtaagtag ttcgccagtt aatagtttgc   1980
gcaacgttgt tgccattgct gcaggcatcg tggtgtcacg ctcgtcgttt ggtatggctt   2040
cattcagctc cggttcccaa cgatcaaggc gagttacatg atccccatg ttgtgcaaaa   2100 aagcggttag ctccttcggt cctccgatcg ttgtcagaag taagttggcc gcagtgttat   2160
cactcatggt tatggcagca ctgcataatt ctcttactgt catgccatcc gtaagatgct   2220
tttctgtgac tggtgagtac tcaaccaagt cattctgaga atagtgtatg cggcgaccga   2280
gttgctcttg cccggcgtca acacgggata ataccgcgcc acatagcaga actttaaaag   2340
tgctcatcat tggaaaacgt tcttcggggc gaaaactctc aaggatctta ccgctgttga   2400
gatccagttc gatgtaaccc actcgtgcac ccaactgatc ttcagcatct tttactttca   2460
ccagcgtttc tgggtgagca aaaacaggaa ggcaaaatgc cgcaaaaaag gaataagggg   2520
cgacacggaa atgttgaata ctcatactct tcctttttca atattattga agcatttatc   2580
agggttattg tctcatgagc ggatacatat ttgaatgtat ttagaaaaat aaacaaatag   2640
```

```
gggttccgcg cacatttccc cgaaaagtgc cacctggatc cacctgcacg taaaaggcct    2700
tcttggccac cccgggccgt cgaccaattc tcatgtttga cagcttatca tcgaatttct    2760
gccattcatc cgcttattat cacttattca ggcgtagcaa ccaggcgttt aagggcacca    2820
ataactgcct taaaaaaatt acgccccgcc ctgccactca tcgcagtact gttgtaattc    2880
attaagcatt ctgccgacat ggaagccatc acaaacggca tgatgaacct gaatcgccag    2940
cggcatcagc accttgtcgc cttgcgtata atatttgccc atggtgaaaa cggggggcgaa   3000
gaagttgtcc atattggcca cgtttaaatc aaaactggtg aaactcaccc agggattggc    3060
tgagacgaaa aacatattct caataaaccc tttagggaaa taggccaggt tttcaccgta    3120
acacgccaca tcttgcgaat atatgtgtag aaactgccgg aaatcgtcgt ggtattcact    3180
ccagagcgat gaaaacgttt cagtttgctc atggaaaacg gtgtaacaag ggtgaacact    3240
atcccatatc accagctcac cgtctttcat tgccatacgg aattccggat gagcattcat    3300
caggcgggca agaatgtgaa taaaggccgg ataaaacttg tgcttatttt tctttacggt    3360
cttttaaaaag gccgtaatat ccagctgaac ggtctggtta taggtacatt gagcaactga   3420
ctgaaatgcc tcaaaatgtt ctttacgatg ccattgggat atatcaacgg tggtatatcc    3480
agtgattttt ttctccattt tagcttcctt agctcctgaa atctcgata actcaaaaaa     3540
tacgcccggt agtgatctta tttcattatg gtgaaagttg gaacctctta cgtgccgatc    3600
aacgtctcat tttcgccaaa agttggccca gggcttcccg gtatcaacag ggacaccagg    3660
atttatttat tctgcgaagt gatcttccgt cacaggtatt tattcgcgat aagctcatgg    3720
agcggcgtaa ccgtcgcaca ggaaggacag agaaagcgcg gatctgggaa gtgacggaca    3780
gaacggtcag gacctggatt ggggaggcgg ttgccgccgc tgctgctgac ggtgtgacgt    3840
tctctgttcc ggtcacacca catacgttcc gccattccta tgcgatgcac atgctgtatg    3900
ccggtatacc gctgaaagtt ctgcaaagcc tgatgggaca taagtccatc agttcaacgg    3960
aagtctacac gaaggttttt gcgctggatg tggctgcccg gcaccgggtg cagtttgcga    4020
tgccggagtc tgatgcggtt gcgatgctga acaattatc ctgagaataa atgccttggc     4080
ctttatatgg aaatgtggaa ctgagtggat atgctgtttt tgtctgttaa acagagaagc    4140
tggctgttat ccactgagaa gcgaacgaaa cagtcgggaa aatctcccat tatcgtagag    4200
atccgcatta ttaatctcag gagcctgtgt agcgtttata ggaagtagtg ttctgtcatg    4260
atgcctgcaa gcggtaacga aaacgatttg aatatgcctt caggaacaat agaaatcttc    4320
gtgcggtgtt acgttgaagt ggagcggatt atgtcagcaa tggacagaac aacctaatga    4380
acacagaacc atgatgtggt ctgtcctttt acagccagta gtgctcgccg cagtcgagcg    4440
acagggcgaa gccctcgagt gagcgaggaa gcaccaggga acagcactta tatattctgc    4500
ttacacacga tgcctgaaaa aacttccctt ggggttatcc acttatccac ggggatattt    4560
ttataattat ttttttttata gttttttagat cttcttttttt agagcgcctt gtaggccttt   4620
atccatgctg gttctagaga aggtgttgtg acaaattgcc ctttcagtgt gacaaatcac    4680
cctcaaatga cagtcctgtc tgtgacaaat tgcccttaac cctgtgacaa attgccctca    4740
gaagaagctg ttttttcaca aagttatccc tgcttattga ctcttttttta tttagtgtga    4800
caatctaaaa acttgtcaca cttcacatgg atctgtcatg gcggaaacag cggttatcaa    4860
tcacaagaaa cgtaaaaaata gcccgcgaat cgtccagtca aacgacctca ctgaggcggc    4920
atatagtctc tcccgggatc aaaaacgtat gctgtatctg ttcgttgacc agatcagaaa    4980
atctgatggc accctacagg aacatgacgg tatctgcgag atccatgttg ctaaatatgc    5040
```

```
tgaaatattc ggattgacct ctgcggaagc cagtaaggat atacggcagg cattgaagag    5100
tttcgcgggg aaggaagtgg ttttttatcg ccctgaagag gatgccggcg atgaaaaagg    5160
ctatgaatct tttccttggt ttatcaaacg tgcgcacagt ccatccagag ggctttacag    5220
tgtacatatc aacccatatc tcattccctt ctttatcggg ttacagaacc ggtttacgca    5280
gtttcggctt agtgaaacaa agaaatcac caatccgtat gccatgcgtt tatacgaatc    5340
cctgtgtcag tatcgtaagc cggatggctc aggcatcgtc tctctgaaaa tcgactggat    5400
catagagcgt taccagctgc ctcaaagtta ccagcgtatg cctgacttcc gccgccgctt    5460
cctgcaggtc tgtgttaatg agatcaacag cagaactcca atgcgcctct catacattga    5520
gaaaaagaaa ggccgccaga cgactcatat cgtatttttcc ttccgcgata tcacttccat    5580
gacgacagga tagtctgagg gttatctgtc acagatttga gggtggttcg tcacatttgt    5640
tctgacctac tgagggtaat ttgtcacagt tttgctgttt ccttcagcct gcatggattt    5700
tctcatactt tttgaactgt aattttttaag gaagccaaat tgagggcag tttgtcacag    5760 ttgatttcct tctcttttccc ttcgtcatgt gacctgatac gcgtgctacc ttaagagagt    5820
caattcgccc ttcccggtcg atatgaacag cttatttaca taattcacgt tattggtagt    5880
tataaatgaa attcctaata tcggttatga agtgaaattg aatttctact tgatctttct    5940 ctctatttt gtaaaataaa attaagaata tttaaatatt caatgattca tttttgcaga    6000
aatcggagga agaagaatat atgaaaacat ttaacatttc tcaacaagat ccccccatat    6060
tgttgtataa gtgatgaaat actgaattta aaacttagtt tatatgtggt aaaatgtttt    6120
aatcaagttt aggaggaatt aattatgaag tgtaatgaat aatgaatgta acagggttca    6180
attaaaagag ggaagcgtat cattaaccct ataaactacg tctgccctca ttattggagg    6240
gtgaaatgtg aatacatcct attcacaatc gaatttacga cacaaccaaa ttttaatttg    6300
gctttgcatt ttatcttttt ttagcgtatt aaatgaaatg gttttgaacg tctcattacc    6360
tgatattgca aatgatttta ataaaccacc agcgagtaca aactgggtga acacagcctt    6420
tatgttaacc ttttccattg gaacagctgt atatggaaag ctatctgatc aattaggcat    6480
caaaaggtta ctcctatttg gaattataat aaattgtttc gggtcggtaa ttgggtttgt    6540
tggccattct ttcttttcct tacttattat ggctcgtttt attcaagggg ctggtgcagc    6600
tgcatttcca gcactcgtaa tggttgtagt tgcgcgctat attccaaagg aaaatagggg    6660
taaagcattt ggtcttattg gatcgatagt agccatggga gaaggagtcg gtccagcgat    6720
tggtggaatg atagcccatt atattcattg gtcctatctt ctactcattc ctatgataac    6780
aattatcact gttccgtttc ttatgaaatt attaaagaaa gaagtaagga taaaggtca    6840 ttttgatatc aaaggaatta tactaatgtc tgtaggcatt gtattttta tgttgtttac    6900 aacatcatat agcatttctt ttcttatcgt tagcgtgctg tcattcctga tatttgtaaa    6960
acatatcagg aaagtaacag atccttttgt tgatcccgga ttagggaaaa atatacccttt    7020 tatgattgga gttctttgtg ggggaattat atttggaaca gtagcagggt ttgtctctat    7080
ggttccttat atgatgaaag atgttcacca gctaagtact gccgaaatcg gaagtgtaat    7140 tatttttccct ggaacaatga gtgtcattat tttcggctac attggtggga tacttgttga    7200
tagaagaggt cctttatacg tgttaaacat cggagttaca tttctttctg ttagcttttt    7260
aactgcttcc tttcttttag aaacaacatc atggttcatg acaattataa tcgtatttgt    7320
tttaggtggg ctttcgttca ccaaaacagt tatatcaaca attgtttcaa gtagcttgaa    7380
acagcaggaa gctggtgctg gaatgagttt gcttaacttt accagctttt tatcagaggg    7440
```

```
aacaggtatt gcaattgtag gtggtttatt atccatacccc ttacttgatc aaaggttgtt    7500
acctatggaa gttgatcagt caacttatct gtatagtaat ttgttattac ttttttcagg    7560
aatcattgtc attagttggc tggttacctt gaatgtatat aaacattctc aaagggattt    7620
ctaaatcgtt aagggatcaa ctttgggaga gagttcaaaa ttgatccttt ttttataaca    7680
ggaattgggc atcaaataaa acgaaaggct cagtcgaaag actgggcctt tcgttttatc    7740
tgttgtttgt cggtgaacgc tctcctgagt aggacaaatc cgccgggagc ggatttgaac    7800
gttgcgaagc aacggcccgg agggtggcgg gcaggacgcc cgccataaac tgccaggcat    7860
caaattaagc agaaggccat cctgacggat ggccttttg cgtttctaca aactcttcct    7920
gtcgtcatat ctacaattct acacagccca gtccagacta ttcggcactg aaattatggg    7980
tgaagtggtc aagacctcac taggcacctt aaaaatagcg caccctgaag aagatttatt    8040
tgaggtagcc cttgcctacc tagcttccaa gaaagatatc ctaacagcac aagagcggaa    8100
agatgttttg ttctacatcc agaacaacct ctgctaaaat tcctgaaaaa ttttgcaaaa    8160
agttgttgac tttatctaca aggtgtggca taatgtgtgg aattgtgagc ggataacaat    8220
taagctaatt ctatggtaaa agcattcctg aacccaatat ccttattttt agtggacaag    8280
gccttgttct catatggttg cttgagccag tgccttacaa ggctcttccg ctttggcagg    8340
ctgttcaaaa ttatttatta gagcaactca aggaactagg cggagatcca aaagcaaccg    8400
atgcagcacg tgtttttcgg attgctggga gcgtcaatga taagaatgga gcggaagtaa    8460
gagcggaata tcggcacgat tacagatatg agttaaggca gattcaattt gattaccttc    8520
cagaactcaa tgaggttatt aatcccgctc acaaaagaa aaaacggggg cgtaaaaga    8580 aagtagttca gttattcaat acctacaaac tccattacgc tcgcctattg gatatagtga    8640
aattggtgga actacgaaat tatgaggtaa ctggatacag ggaaatcatt tgcttttat    8700 accgttattg gttgtgctgt tacacgaacg accctgtaga ggcttaaat caaacacaga    8760 cacttaattt acagttcact gagcctttac ccttaaaaga ggttgaaagg gctacacgga    8820
gcgcagaaaa ggcgtgggaa gcacgaaata acgaagaggc taaccggatt gcaatcgaaa    8880
aaggatatcc cagtgctgga tacaatatta gcaataaaaa gttgattgaa tggctagata    8940
tcacaccaga agaacagaag catttacaga cgattataga cgctaatgag aaacggagaa    9000
gaaagcggga aagggatagg atttatcaag aacaaaaacg tcgtgagcgg ggagatatga    9060
cccgacagga gtatattaag caacaacagg ataaaacaga tgataaatta tttaaattgc    9120
aggagttatt agaacagaat cccaaaatct caaaaattaa attagcaaaa atacttggtg    9180
tagataaatc gcacttatac agactgctga aacaactata actggaaaaa attagtgtct    9240
catggttcgt cgcccttata ttatgggcgt tagcctgctt gctaattgga taggtgttat    9300
tgtcatttca acgtcggacg ttttggtaga tgaacgtcgg acgttatttg cttcaataga    9360
ttgttgatgt attaagggtt gcagtgaatc gacaagcaaa aagttatgac gttgtgaaaa    9420
aattgaatag aaaattggaa attacgtcgg acgttctaac ttaaaaaccc tgttatatca    9480
atgatttaaa aggaaattaa cgtcataaaa gacctttctg caacaaaagt ttttctggaa    9540
gagttgaggt tatttatag gtattatgga cttttgtaga cttttgtgt acttttgtg    9600 gactccacac tcgctggtat cgtgttattt tttaattgag atatgaatat ggaaattaaa    9660
cgttttaggc gttggtttgg tgatgacaaa aaaataagag tacccgctca caacggatac    9720
tctttcgaga aatgtacgaa acgctataaa taaaaaataa ctagatacat ttacattgta    9780
tcacgtttcg tacatttctc caataacaaa ttgattggag gaatgcaaag tgaataatga    9840
```

```
accagtaaaa cgtggtaaga agaacagatg ggaattaaac ctacctataa tgacttatgt   9900
agtagctgat gattggattg ataaactagg acacgaaacg tttactttat ggttgaggtt   9960
ccatacttgg gtagatagag aagatgaact ccgagattat gatcgcatac ctagaagttt  10020
tgagaacata tataaaaaga cactaggaat ctcaaaaagt aagttttata gattgataaa  10080
acctttatgg gaatatggat taatagacat catagaatac gaagaatcta accgtaattc  10140
tactaaacct aaaaatataa ttgtttatga gtatcccttta cacgaaatag aaagaaagta  10200
taaaccacta gaaaaattaa gagattggga taaagactat aattccgttt ctaaagaatt  10260
aggtaaaaca ggtggtagac caaggaaaaa agatagtgaa gaagaacccg aaaagaaacc  10320
cgaagaagta actaaaaaga aacgtaaata taagttaaaa agagttatcc acaacggttt  10380
caaaaatgaa acgtggagg gtttcaaaaa tgaaacggtg gagggtttca aaaatgaaac  10440
ggtgaccgtt tcaaaaataa aacccaataa ttattcaaat atctttaata acttatcaaa  10500
tatttctact aatgtttcaa ataatttatt aattgatgat gatgaggaaa tcgaaaatga  10560
accaactggt cgtacaataa ataggtcatt acttttttca caagaagata ttaaacaggc  10620
ctatcaattt attaatagat tttcagttat acagttacgt gaaaacttta gctttgataa  10680
acactttgaa gaacggttgg tatgttattt atggaaagca gggatttcta cttttttacac  10740 gcacgaaatc agtaaaatga taaaaaaaat agcagactat gaaaaatcta aaaaaggtag  10800
attaaaccca atacgtgacc gagccttata tatggtaaat ggtcttgtaa tgaatagagc  10860
ttcttcccaa agtgaacatg ctacttataa actaaaccaa tataaaaaac agaaggaaca  10920
ggaaaaacaa caacaggagc aacaaagatc aagagtaccg ttctataatt ggttggagga  10980
aagagaagaa caaaccgaag gtcaactacc caccacttaa agcctaacgg cttttgaagt  11040
ggggcttgta aaaagccccta gttgactacc ccaagtctttt cgaggactac gttggaaagg  11100
tcatgacacc tacaaatgct cctctagttc gtagccactg tcgttgatgg ttaaaagtcc  11160
tgatgggtag ggacggtgct gtcaacatca caagcccttc caacatgggg gaagaggaag  11220
aacactccga gaaggagggg ggctgtcgta cacgccttgt tcgtgtacgt gattttaac  11280 acttttatct ctaatataat ctctccttga gttagcagag actaagaata aaacacatta  11340
ggatttttta tctacataag gaggttcaat acatgcctac tatttcgttt aagggaaagt  11400
cttttgtaca aaatcatcac ttgactgtaa aatatcatga attgatccca gaaccagaaa  11460
aaagtctgac cgataaagtt agtcttcatg acaatcttat cattcatggg gacaatttaa  11520
aggcgttgaa agctctacta cctacatatg ctggtaagat agattgcatc tatattgacc  11580
caccatacaa tactggaact gaaaaatgga tttataatga taatgtcaac tccccaatga  11640
ttagggaatg gcttggaaaa gtggtagaca agaagactt atcccgacat gataagtggc  11700
tttgtatgat gatgccgagg ttaaaactgt tgaaagagtt gttgtcagaa gacggagtga  11760
tatttgtaag cattgactac aatgaaatac accatcttac gtgccttatg aacgaaatat  11820
tcggtgagga gaattttcgt gacgctatta tcattcgtag aggagtaaaa aatgttcaag  11880
cgcaatttga cacaattgat tctctttcaa atggttatga gtctattttg gtttacacta  11940
aacagccatc tcgacgattt aataaggttt atgaagatgt agaagaaaag cctggtagtt  12000
ggaataatca ttggagaggt acagaccgta aaactatgag atatgaatta tttggggtta  12060
ctccgacaga aggtcaatgg agatggggga aagaacgtag tctccaggct attgaaaact  12120
atcaaatgat gttagatgaa cttagacaaa aaggcattac taatccaact caagaggata  12180
ttgataaatg gtatcttgaa tatgtagaaa ataatgggga agatattgac ttgttacgac  12240
```

```
aaaatgataa tggcacgatt gagcactttg ttccaccgac tagcaaaaag ttgttaagta    12300
atgcctggtt tgacttaaaa cccaacggtt ctagtcaatt aaagaagata tttggaagga    12360
aggttttcga taaccctaaa tcaattgatt tggtaaaaag actaatacaa tttgcgactg    12420
aaaacaaaga agcgattgta cttgactcat ttgcagggag tggcactact gctcatgcag    12480
tattatcgct taacaaacaa gatggaggga atcgtcgttt catccttatt gagatggaag    12540
aatatgcaca tgagattacc gcagaacgcg gatctttatc gatttgcatg caagctaatt    12600
cggtggaaac gaggtcatca tttccttccg aaaaaacggt tgcatttaaa tcttacatat    12660
gtaatacttt caaagactac atttgtaaga tttgatgttt gagtcggctg aaagatcgta    12720
cgtaccaatt attgtttcgt gattgttcaa gccataacac tgtagggata gtggaaagag    12780
tgcttcatct ggttacgatc aatcaaatat tcaaacggag ggagacgatt ttgatgaaac    12840
cagtaacgtt atacgatgtc gcagagtatg ccggtgtctc ttatcagacc gtttcccgcg    12900
tggtgaacca ggccagccac gtttctgcga aaacgcggga aaagtggaa gcggcgatgg    12960 cggagctgaa ttacattccc aaccgcgtgg cacaacaact ggcgggcaaa cagtcgttgc    13020
tgattggcgt tgccacctcc agtctggccc tgcacgcgcc gtcgcaaatt gtcgcggcga    13080
ttaaatctcg cgccgatcaa ctgggtgcca gcgtggtggt gtcgatggta gaacgaagcg    13140
gcgtcgaagc ctgtaaaacg gcggtgcaca atcttctcgc gcaacgcgtc agtgggctga    13200
tcattaacta tccgctggat gaccaggatg ccattgctgt ggaagctgcc tgcactaatg    13260
ttccggcgtt atttcttgat gtctctgacc agacacccat caacagtatt attttctccc    13320
atgaagacgt tacgcgactg ggcgtggagc atctggtcgc attgggtcac cagcaaatcg    13380
cgctgttagc gggcccatta agttctgtct cggcgcgtct gcgtctggct ggctggcata    13440
aatatctcac tcgcaatcaa attcagccga tagcggaacg ggaaggcgac tggagtgcca    13500
tgtccggttt tcaacaaacc atgcaaatgc tgaatgaggg catcgttccc actgcgatgc    13560
tggttgccaa cgatcagatg gcgctgggcg caatgcgcgc cattaccgag tccgggctgc    13620
gcgttggtgc ggatatctcg gtagtgggat acgacgatac cgaagacagc tcatgttata    13680
tcccgccgtt aaccaccatc aaacaggatt ttcgcctgct ggggcaaacc agcgtggacc    13740
gcttgctgca actctctcag ggccaggcgg tgaagggcaa tcagctgttg cccgtctcac    13800
tggtgaaaag aaaaaccacc ctggcgccca atacgcaaac cgcctctccc cgcgcgttgg    13860
ccgattcatt aatgcagctg gcacgacagg tttcccgact ggaaagcggg cagtgagcgc    13920
aacgcaatta atgtgagtta ggatcgctac cttaagagag acgcgttatc gggggttagt    13980
tcgtcatcat tgatgagggt tgattatcac agtttattac tctgaattgg ctatccgcgt    14040
gtgtacctct acctggagtt tttcccacgg tggatatttc ttcttgcgct gagcgtaaga    14100
gctatctgac agaacagttc ttctttgctt cctcgccagt tcgctcgcta tgctcggtta    14160
cacggctgcg gcgagcgcta gtgataataa gtgactgagg tatgtgctct tcttatctcc    14220
ttttgtagtg ttgctcttat tttaaacaac tttgcggttt tttgatgact ttgcgatttt    14280
gttgttgctt tgcagtaaat tgcaagattt aataaaaaaa cgcaaagcaa tgattaaagg    14340
atgttcagaa tgaaactcat ggaaacactt aaccagtgca taaacgctgg tcatgaaatg    14400
acgaaggcta tcgccattgc acagtttaat gatgacagcc cggaagcgag gaaaataacc    14460
cggcgctgga gataggtgaa agcagcggat ttagttgggg tttcttctca ggctatcaga    14520
gatgccgaga aagcagggcg actaccgcac ccggatatgg aaattcgagg acgggttgag    14580
caacgtgttg gttatacaat tgaacaaatt aatcatatgc gtgatgtgtt tggtacgcga    14640
```

-continued

```
ttgcgacgtg ctgaagacgt atttccaccg gtgatcgggg ttgctgccca taaaggtggc   14700
gtttacaaaa cctcagtttc tgttcatctt gctcaggatc tggctctgaa ggggctacgt   14760
gttttgctcg tggaaggtaa cgaccccag ggaacagcct caatgtatca cggatgggta    14820
ccagatcttc atattcatgc agaagacact ctcctgcctt tctatcttgg ggaaaaggac   14880
gatgtcactt atgcaataaa gcccacttgc tggccgggc ttgacattat tccttcctgt    14940
ctggctctgc accgtattga aactgagtta atgggcaaat ttgatgaagg taaactgccc   15000
accgatccac acctgatgct ccgactggcc attgaaactg ttgctcatga ctatgatgtc   15060
atagttattg acagcgcgcc taacctgggt atcggcacga ttaatgtcgt atgtgctgct   15120
gatgtgctga ttgttcccac gcctgctgag ttgtttgact acacctccgc actgcagttt   15180
ttcgatatgc ttcgtgatct gctcaagaac gttgatctta aagggttcga gcctgatgta   15240
cgtattttgc ttaccaaata cagcaatagt aatggctctc agtccccgtg gatggaggag   15300
caaattcggg atgcctgggg aagcatggtt ctaaaaaatg ttgtacgtga aacggatgaa   15360
gttggtaaag gtcagatccg gatgagaact gttttttgaac aggccattga tcaacgctct   15420
tcaactggtg cctggagaaa tgctctttct atttgggaac ctgtctgcaa tgaaattttc   15480
gatcgtctga ttaaaccacg ctgggagatt agataatgaa gcgtgcgcct gttattccaa   15540
aacatacgct caatactcaa ccggttgaag atacttcgtt atcgacacca gctgccccga   15600
tggtggattc gttaattgcg cgcgtaggag taatggctcg cggtaatgcc attactttgc   15660
ctgtatgtgg tcgggatgtg aagtttactc ttgaagtgct ccggggtgat agtgttgaga   15720
agacctctcg ggtatggtca ggtaatgaac gtgaccagga gctgcttact gaggacgcac   15780
tggatgatct catcccttct tttctactga ctggtcaaca gacaccggcg ttcggtcgaa   15840
gagtatctgt tgtcatagaa attgccgatg ggagtcgccg tcgtaaagct gctgcactta   15900
ccgaaagtga ttatcgtgtt ctggttggcg agctggatga tgagcagatg gctgcattat   15960
ccagattggg taacgattat cgcccaacaa gtgcttatga acgtggtcag cgttatgcaa   16020
gccgattgca gaatgaattt gctggaaata tttctgcgct ggctgatgcg gaaaatattt   16080
cacgtaagat tattacccgc tgtatcaaca ccgccaaatt gcctaaatca gttgttgctc   16140 tttttttctca ccccggtgaa ctatctgccc ggtcaggtga tgcacttcaa aaagccttta   16200
cagataaaga ggaattactt aagcagcagg catctaacct tcatgagcag aaaaaagctg   16260
gggtgatatt tgaagctgaa gaagttatca ctcttttaac ttctgtgctt aaaacgtcat   16320
ctgcatcaag aactagttta agctcacgac atcagtttgc tcctggagcg acagtattgt   16380
ataagggcga taaatggtg cttaacctgg acaggtctcg tgttccaact gagtgtatag    16440
agaaaattga ggccattctt aaggaacttg aaaagccagc ccctgatgc gaccacgttt     16500 tagtctacgt ttatctgtct ttacttaatg tcctttgtta caggccagaa agcataactg   16560
gcctgaatat tctctctggg cccactgttc cacttgtatc gtcggtctga taatcagact   16620
gggaccacgg tcccactcgt atcgtcggtc tgattattag tctgggacca cggtcccact   16680
cgtatcgtcg gtctgattat tagtctggga ccacggtccc actcgtatcg tcggtctgat   16740
aatcagactg gaccacggt cccactcgta tcgtcggtct gattattagt ctgggaccat    16800
ggtcccactc gtatcgtcgg tctgattatt agtctgggac cacggtccca ctcgtatcgt   16860
cggtctgatt attagtctgg aaccacggtc ccactcgtat cgtcggtctg attattagtc   16920
tgggaccacg gtcccactcg tatcgtcggt ctgattatta gtctgggacc acgatcccac   16980
tcgtgttgtc ggtctgatta tcggtctggg accacggtcc cacttgtatt gtcgatcaga   17040
```

-continued

| | |
|---|---|
| ctatcagcgt gagactacga ttccatcaat gcctgtcaag ggcaagtatt gacatgtcgt | 17100 |
| cgtaacctgt agaacggagt aacctcggtg tgcggttgta tgcctgctgt ggattgctgc | 17160 |
| tgtgtcctgc ttatccacaa cattttgcgc acggttatgt ggacaaaata cctggttacc | 17220 |
| caggccgtgc cggcacgtta accgggctgc atccgatgca agtgtgtcgc tgtcgacgag | 17280 |
| ctcgcgagct cggacatgag gttgccccgt attcagtgtc gctgatttgt attgtctgaa | 17340 |
| gttgttttta cgttaagttg atgcagatca attaatacga tacctgcgtc ataattgatt | 17400 |
| atttgacgtg gtttgatggc ctccacgcac gttgtgatat gtagatgata atcattatca | 17460 |
| ctttacgggt cctttccggt gatccgacag gttacggggc ggcgacctcg cgggttttcg | 17520 |
| ctatttatga aaattttccg gtttaaggcg tttccgttct tcttcgtcat aacttaatgt | 17580 |
| ttttatttaa ataccctct gaaaagaaag gaaacgacag gtgctgaaag cgagcttttt | 17640 |
| ggcctctgtc gtttcctttc tctgtttttg tccgtggaat gaacaatgga agtccgagct | 17700 |
| catcgctaat aacttcgtat agcatacatt atacgaagtt atattcgat | 17749 |

<210> SEQ ID NO 2
<211> LENGTH: 6912
<212> TYPE: DNA
<213> ORGANISM: Artificial Sequence
<220> FEATURE:
<223> OTHER INFORMATION: Artificial plasmid

<400> SEQUENCE: 2

| | |
|---|---|
| gcggccgcaa gcttgaagag ctcttctttc agaacgctcg gttgccgccg ggcgttttt | 60 |
| atgagacgtc tcggcctgtt tggccattaa cgtgcaggtg gatccagatc taagcttcta | 120 |
| tagaagcttg gtaccgacgt ctcggcctgt ttggcccgcc gcatccatac cgccagttgt | 180 |
| ttaccctcac aacgttccag taaccgggca tgttcatcat cagtaacccg tatcgtgagc | 240 |
| atcctctctc gtttcatcgg tatcattacc cccatgaaca gaaatccccc ttacacggag | 300 |
| gcatcagtga ccaaacagga aaaaaccgcc cttaacatgg cccgctttat cagaagccag | 360 |
| acattaacgc ttctggagaa actcaacgag ctggacgcgg atgaacaggc agacatctgt | 420 |
| gaatcgcttc acgaccacgc tgatgagctt taccgcagct gcctcgcgcg tttcggtgat | 480 |
| gacggtgaaa acctctgaca catgcagctc ccgaagacgg tcacagcttg tctgtaagcg | 540 |
| gatgccggga gcagacaagc ccgtcagggc gcgtcagcgg tgttggcgg tgtcggggc | 600 |
| gcagccatga cccagtcacg tagcgatagc ggagtgtata ctggcttaac tatgcggcat | 660 |
| cagagcagat tgtactgaga gtgcaccata tgcggtgtga ataccgcac agatgcgtaa | 720 |
| ggagaaaata ccgcatcagg cactcttccg cttcctcgct cactgactcg ctgcgctcgg | 780 |
| tcgttcggct gcggcgagcg gtatcagctc actcaaaggc ggtaatacgg ttatccacag | 840 |
| aatcagggga taacgcagga agaacatgt gagcaaaagg ccagcaaaag gccaggaacc | 900 |
| gtaaaaaggc cgcgttgctg gcgttttcc ataggctccg ccccctgac gagcatcaca | 960 |
| aaaatcgacg ctcaagtcag aggtggcgaa acccgacagg actataaaga taccaggcgt | 1020 |
| ttccccctgg aagctccctc gtgcgctctc ctgttccgac cctgccgctt accggatacc | 1080 |
| tgtccgcctt tctcccttcg ggaagcgtgg cgctttctca tagctcacgc tgtaggtatc | 1140 |
| tcagttcggt gtaggtcgtt cgctccaagc tgggctgtgt gcacgaaccc cccgttcagc | 1200 |
| ccgaccgctg cgccttatcc ggtaactatc gtcttgagtc caacccggta agacacgact | 1260 |
| tatcgccact ggcagcagcc actggtaaca ggattagcag agcgaggtat gtaggcggtg | 1320 |
| ctacagagtt cttgaagtgg tggcctaact acggctacac tagaaggaca gtatttggta | 1380 |

```
tctgcgctct gctgaagcca gttaccttcg gaaaaagagt tggtagctct tgatccggca   1440
aacaaaccac cgctggtagc ggtggttttt ttgtttgcaa gcagcagatt acgcgcagaa   1500
aaaaaggatc tcaagaagat cctttgatct tttctacggg gtctgacgct cagtggaacg   1560
aaaactcacg ttaagggatt ttggtcatga gattatcaaa aaggatcttc acctagatcc   1620
ttttaaatta aaaatgaagt tttaaatcaa tctaaagtat atatgagtaa acttggtctg   1680
acagttacca atgcttaatc agtgaggcac ctatctcagc gatctgtcta tttcgttcat   1740
ccatagttgc ctgactcccc gtcgtgtaga taactacgat acgggagggc ttaccatctg   1800
gccccagtgc tgcaatgata ccgcgagacc cacgctcacc ggctccagat ttatcagcaa   1860
taaaccagcc agccggaagg gccgagcgca gaagtggtcc tgcaacttta tccgcctcca   1920
tccagtctat taattgttgc cgggaagcta gagtaagtag ttcgccagtt aatagtttgc   1980
gcaacgttgt tgccattgct gcaggcatcg tggtgtcacg ctcgtcgttt ggtatggctt   2040
cattcagctc cggttcccaa cgatcaaggc gagttacatg atcccccatg ttgtgcaaaa   2100
aagcggttag ctccttcggt cctccgatcg ttgtcagaag taagttggcc gcagtgttat   2160
cactcatggt tatggcagca ctgcataatt ctcttactgt catgccatcc gtaagatgct   2220
tttctgtgac tggtgagtac tcaaccaagt cattctgaga atagtgtatg cggcgaccga   2280
gttgctcttg cccggcgtca acacgggata ataccgcgcc acatagcaga actttaaaag   2340
tgctcatcat tggaaaacgt tcttcggggc gaaaactctc aaggatctta ccgctgttga   2400
gatccagttc gatgtaaccc actcgtgcac ccaactgatc ttcagcatct tttactttca   2460
ccagcgtttc tgggtgagca aaaacaggaa ggcaaaatgc cgcaaaaaag gaataagggg   2520
cgacacggaa atgttgaata ctcatactct tcctttttca atattattga agcatttatc   2580
agggttattg tctcatgagc ggatacatat ttgaatgtat ttagaaaaat aaacaaatag   2640
gggttccgcg cacatttccc cgaaaagtgc cacctggatc cacctgcacg taaaaggcct   2700
tcttggccgc ccttcccggt cgatatgaac agcttattta cataattcac gttattggta   2760
gttataaatg aaattcctaa tatcggttat gaagtgaaat tgaatttcta cttgatcttt   2820 ctctctatt ttgtaaaata aaattaagaa tatttaaata ttcaatgatt cattttttgca   2880 gaaatcggag gaagaagaat atatgaaaac atttaacatt tctcaacaag atcccccat   2940 attgttgtat aagtgatgaa atactgaatt taaaacttag tttatatgtg gtaaaatgtt   3000
ttaatcaagt ttaggaggaa ttaattatga agtgtaatga ataatgaatg taacagggtt   3060
caattaaaag agggaagcgt atcattaacc ctataaacta cgtctgccct cattattgga   3120
gggtgaaatg tgaatacatc ctattcacaa tcgaatttac gacacaacca aattttaatt   3180
tggctttgca ttttatctt ttttagcgta ttaaatgaaa tggttttgaa cgtctcatta   3240
cctgatattg caaatgattt taataaacca ccagcgagta caaactgggt gaacacagcc   3300
tttatgttaa ccttttccat tggaacagct gtatatggaa agctatctga tcaattaggc   3360
atcaaaaggt tactcctatt tggaattata ataaattgtt tcgggtcggt aattgggttt   3420
gttggccatt ctttctttc cttacttatt atggctcgtt ttattcaagg ggctggtgca   3480
gctgcatttc cagcactcgt aatggttgta gttgcgcgct atattccaaa ggaaaatagg   3540
ggtaaagcat ttggtcttat tggatcgata gtagccatgg gagaaggagt cggtccagcg   3600
attggtggaa tgatagccca ttatattcat tggtcctatc ttctactcat tcctatgata   3660
acaattatca ctgttccgtt tcttatgaaa ttattaaaga aagaagtaag gataaaaggt   3720 catttttgata tcaaaggaat tatactaatg tctgtaggca ttgtattttt tatgttgttt   3780
```

```
acaacatcat atagcatttc ttttcttatc gttagcgtgc tgtcattcct gatatttgta    3840
aaacatatca ggaaagtaac agatcctttt gttgatcccg gattagggaa aaatatacct    3900
tttatgattg gagttctttg tggggaatt atatttggaa cagtagcagg gtttgtctct     3960
atggttcctt atatgatgaa agatgttcac cagctaagta ctgccgaaat cggaagtgta    4020
attattttcc ctggaacaat gagtgtcatt attttcggct acattggtgg gatacttgtt    4080
gatagaagag gtcctttata cgtgttaaac atcggagtta catttctttc tgttagcttt    4140
ttaactgctt cctttctttt agaaacaaca tcatggttca tgacaattat aatcgtatt    4200 gttttaggtg ggctttcgtt caccaaaaca gttatatcaa caattgtttc aagtagcttg    4260
aaacagcagg aagctggtgc tggaatgagt ttgcttaact ttaccagctt tttatcagag    4320
ggaacaggta ttgcaattgt aggtggttta ttatccatac ccttacttga tcaaaggttg    4380
ttacctatgg aagttgatca gtcaacttat ctgtatagta atttgttatt acttttttca    4440
ggaatcattg tcattagttg gctggttacc ttgaatgtat ataaacattc tcaaagggat    4500
ttctaaatcg ttaagggatc aactttggga gagagttcaa aattgatcct ttttttataa    4560
caggaattgg gcatcaaata aaacgaaagg ctcagtcgaa agactgggcc tttcgtttta    4620
tctgttgttt gtcggtgaac gctctcctga gtaggacaaa tccgccggga gcggatttga    4680
acgttgcgaa gcaacggccc ggagggtggc gggcaggacg cccgccataa actgccaggc    4740
atcaaattaa gcagaaggcc atcctgacgg atggcctttt tgcgtttcta caactcttc    4800 ctgtcgtcat atctacaatt ctacacagcc cagtccagac tattcggcac tgaaattatg    4860
ggtgaagtgg tcaagacctc actaggcacc ttaaaaatag cgcaccctga agaagattta    4920
tttgaggtag cccttgccta cctagcttcc aagaaagata tcctaacagc acaagagcgg    4980
aaagatgttt tgttctacat ccagaacaac ctctgctaaa attcctgaaa aattttgcaa    5040
aaagttgttg actttatcta caaggtgtgg cataatgtgt ggaattgtga gcggataaca    5100
attaagctaa taactggaaa aaattagtgt ctcatggttc gtcgcccta tattatgggc     5160 gttagcctgc ttgctaattg ataggtgtt attgtcattt caacgtcgga cgttttggta    5220
gatgaacgtc ggacgttatt tgcttcaata gattgttgat gtattaaggg ttgcagtgaa    5280
tcgacaagca aaagttatg acgttgtgaa aaaattgaat agaaaattgg aaattacgtc     5340
ggacgttcta acttaaaaac cctgttatat caatgattta aaaggaaatt aacgtcataa    5400
aagacctttc tgcaacaaaa gttttttctgg aagagttgag gttatttat aggtattatg    5460 gacttttgta gactttttgt gtactttttg tggactccac actcgctggt atcgtgttat    5520
tttttaattg agatatgaat atggaaatta acgttttag gcgttggttt ggtgatgaca    5580
aaaaaataag agtacccgct cacaacggat actctttcga gaaatgtacg aaacgctata    5640
aataaaaaat aactagatac atttacattg tatcacgttt cgtacatttc tccaataaca    5700
aattgattgg aggaatgcaa agtgaataat gaaccagtaa acgtggtaa aagaacaga      5760 tgggaattaa acctacctat aatgacttat gtagtagctg atgattggat tgataaacta    5820
ggacacgaaa cgtttacttt atggttgagg ttccatactt gggtagatag agaagatgaa    5880 ctccagagatt atgatcgcat acctagaagt tttgagaaca tatataaaaa gacactagga    5940
atctcaaaaa gtaagtttta tagattgata aaaccttat gggaatatgg attaatagac     6000
atcatagaat acgaagaatc taaccgtaat tctactaaac ctaaaaatat aattgttat     6060 gagtatcctt tacacgaaat agaaagaaag tataaaccac tagaaaaatt aagagattgg    6120
gataaagact ataattccgt ttctaaagaa ttaggtaaaa caggtggtag accaaggaaa    6180
```

```
aaagatagtg aagaagaacc cgaaaagaaa cccgaagaag taactaaaaa gaaacgtaaa      6240
tataagttaa aaagagttat ccacaacggt ttcaaaaatg aaacggtgga gggtttcaaa      6300
aatgaaacgg tggagggttt caaaaatgaa acggtgaccg tttcaaaaat aaaacccaat      6360
aattattcaa atatctttaa taacttatca aatatttcta ctaatgtttc aaataattta      6420
ttaattgatg atgatgagga atcgaaaat  gaaccaactg gtcgtacaat aaataggtca      6480
ttactttttt cacaagaaga tattaaacag gcctatcaat ttattaatag attttcagtt      6540
atacagttac gtgaaaactt tagctttgat aaacactttg aagaacggtt ggtatgttat      6600
ttatggaaag cagggatttc tacttttttac acgcacgaaa tcagtaaaat gataaaaaaa      6660
atagcagact atgaaaaatc taaaaaaggt agattaaacc caatacgtga ccgagcctta      6720
tatatggtaa atggtcttgt aatgaataga gcttcttccc aaagtgaaca tgctacttat      6780
aaactaaacc aatataaaaa acagaaggaa caggaaaaac aacaacagga gcaacaaaga      6840
tcaagagtac cgttctataa ttggttggag gaaagagaag aacaaaccga aggtcaacta      6900
cccaccactt aa                                                         6912

<210> SEQ ID NO 3
<211> LENGTH: 48526
<212> TYPE: DNA
<213> ORGANISM: Bacteriophage lambda

<400> SEQUENCE: 3
attacggggc ggcgacctcg cgggttttcg ctatttatga aaattttccg gtttaaggcg        60
tttccgttct tcttcgtcat aacttaatgt ttttatttaa atacccctct gaaaagaaag       120
gaaacgacag gtgctgaaag cgagcttttt ggcctctgtc gtttcctttc tctgtttttg       180
tccgtggaat gaacaatgga agtcaacaaa aagcagctgg ctgacatttt cggtgcgagt       240
atccgtacca ttcagaactg gcaggaacag ggaatgcccg ttctgcgagg cggtggcaag       300
ggtaatgagg tgctttatga ctctgccgcc gtcataaaat ggtatgccga aagggatgct       360
gaaattgaga acgaaaagct cgcccgggag gttgaagaac tgcggcaggc cagcgaggca       420
gatctccagc caggaactat tgagtacgaa cgccatcgac ttacgcgtgc gcaggccgac       480
gcacaggaac tgaagaatgc cagagactcc gctgaagtgg tggaaaccgc attctgtact       540
ttcgtgctgt cgcggatcgc aggtgaaatt gccagtattc tcgacgggct ccccctgtcg       600
gtgcagcggc gttttccgga actggaaaac cgacatgttg atttcctgaa acgggatatc       660
atcaaagcca tgaacaaagc agccgcgctg gatgaactga taccgggggtt gctgagtgaa      720 tatatcgaac agtcaggtta acaggctgcg gcattttgtc cgcgccgggc ttcgctcact       780
gttcaggccg gagccacaga ccgccgttga atgggcggat gctaattact atctcccgaa       840
agaatccgca taccaggaag ggcgctggga aacactgccc tttcagcggg ccatcatgaa       900
tgcgatgggc agcgactaca tccgtgaggt gaatgtggtg aagtctgccc gtgtcggtta       960
ttccaaaatg ctgctgggtg tttatgccta ctttatagag cataagcagc gcaacaccct      1020
tatctggttg ccgacggatg gtgatgccga gaactttatg aaaacccacg ttgagccgac      1080
tattcgtgat attccgtcgc tgctggcgct ggccccgtgg tatggcaaaa agcaccggga      1140
taacacgctc accatgaagc gtttcactaa tgggcgtggc ttctggtgcc tgggcggtaa      1200
agcggcaaaa aactaccgtg aaaagtcggt ggatgtggcg ggttatgatg aacttgctgc      1260
ttttgatgat gatattgaac aggaaggctc tccgacgttc ctgggtgaca gcgtattga      1320 aggctcggtc tggccaaagt ccatccgtgg ctccacgcca aaagtgagag gcacctgtca      1380
```

```
gattgagcgt gcagccagtg aatccccgca ttttatgcgt tttcatgttg cctgcccgca    1440
ttgcggggag gagcagtatc ttaaatttgg cgacaaagag acgccgtttg gcctcaaatg    1500
gacgccggat gaccccctcca gcgtgtttta tctctgcgag cataatgcct gcgtcatccg    1560
ccagcaggag ctggactttta ctgatgcccg ttatatctgc gaaaagaccg ggatctggac    1620
ccgtgatggc attctctggt tttcgtcatc cggtgaagag attgagccac ctgacagtgt    1680
gacctttcac atctggacag cgtacagccc gttcaccacc tgggtgcaga ttgtcaaaga    1740
ctggatgaaa acgaaagggg atacgggaaa acgtaaaacc ttcgtaaaca ccacgctcgg    1800
tgagacgtgg gaggcgaaaa ttggcgaacg tccggatgct gaagtgatgg cagagcggaa    1860
agagcattat tcagcgcccg ttcctgaccg tgtggcttac ctgaccgccg gtatcgactc    1920
ccagctggac cgctacgaaa tgcgcgtatg gggatggggg ccgggtgagg aaagctggct    1980
gattgaccgg cagattatta tgggccgcca cgacgatgaa cagacgctgc tgcgtgtgga    2040
tgaggccatc aataaaacct atacccgccg gaatggtgca gaaatgtcga tatcccgtat    2100
ctgctgggat actggcggga ttgacccgac cattgtgtat aacgctcga aaaaacatgg    2160 gctgttccgg gtgatcccca ttaaaggggc atccgtctac ggaaagccgg tggccagcat    2220
gccacgtaag cgaaacaaaa acggggttta ccttaccgaa atcggtacgg ataccgcgaa    2280
agagcagatt tataaccgct tcacactgac gccggaaggg gatgaaccgc ttcccggtgc    2340
cgttcacttc ccgaataacc cggatatttt tgatctgacc gaagcgcagc agctgactgc    2400
tgaagagcag gtcgaaaaat gggtggatgg caggaaaaaa atactgtggg acagcaaaaa    2460
gcgacgcaat gaggcactcg actgcttcgt ttatgcgctg gcggcgctgc gcatcagtat    2520
ttcccgctgg cagctggatc tcagtgcgct gctggcgagc ctgcaggaag aggatggtgc    2580
agcaaccaac aagaaaacac tggcagatta cgcccgtgcc ttatccggag aggatgaatg    2640
acgcgacagg aagaacttgc cgctgcccgt gcggcactgc atgacctgat gacaggtaaa    2700
cgggtggcaa cagtacagaa agacggacga agggtggagt ttacggccac ttccgtgtct    2760
gacctgaaaa aatatattgc agagctggaa gtgcagaccg gcatgacaca gcgacgcagg    2820
ggacctgcag gattttatgt atgaaaacgc ccaccattcc cacccttctg gggccggacg    2880
gcatgacatc gctgcgcgaa tatgccggtt atcacggcgg tggcagcgga tttggagggc    2940
agttgcggtc gtggaaccca ccgagtgaaa gtgtggatgc agccctgttg cccaacttta    3000
cccgtggcaa tgcccgcgca gacgatctgg tacgcaataa cggctatgcc gccaacgcca    3060
tccagctgca tcaggatcat atcgtcgggt ctttttttccg gctcagtcat cgcccaagct    3120
ggcgctatct gggcatcggg gaggaagaag cccgtgcctt ttcccgcgag gttgaagcgg    3180
catggaaaga gtttgccgag gatgactgct gctgcattga cgttgagcga aaacgcacgt    3240
ttaccatgat gattcgggaa ggtgtggcca tgcacgcctt taacggtgaa ctgttcgttc    3300
aggccacctg gataccagt tcgtcgcggc ttttccggac acagttccgg atggtcagcc    3360
cgaagcgcat cagcaacccg aacaataccg gcgacagccg gaactgccgt gccggtgtgc    3420
agattaatga cagcggtgcg gcgctgggat attacgtcag cgaggacggg tatcctggct    3480
ggatgccgca gaaatggaca tggatacccc gtgagttacc cggcgggcgc gcctcgttca    3540
ttcacgtttt tgaacccgtg gaggacgggc agactcgcgg tgcaaatgtg ttttacagcg    3600
tgatggagca gatgaagatg ctcgacacgc tgcagaacac gcagctgcag agcgccattg    3660
tgaaggcgat gtatgccgcc accattgaga gtgagctgga tacgcagtca gcgatggatt    3720
ttattctggg cgcgaacagt caggagcagc gggaaaggct gaccggctgg attggtgaaa    3780
```

```
ttgccgcgta ttacgccgca gcgccggtcc ggctggggagg cgcaaaagta ccgcacctga   3840
tgccgggtga ctcactgaac ctgcagacgg ctcaggatac ggataacggc tactccgtgt   3900
ttgagcagtc actgctgcgg tatatcgctg ccgggctggg tgtctcgtat gagcagcttt   3960
cccggaatta cgcccagatg agctactcca cggcacgggc cagtgcgaac gagtcgtggg   4020
cgtactttat ggggcggcga aaattcgtcg catcccgtca ggcgagccag atgtttctgt   4080
gctggctgga agaggccatc gttcgccgcg tggtgacgtt accttcaaaa gcgcgcttca   4140
gttttcagga agcccgcagt gcctggggga actgcgactg ataggctcc ggtcgtatgg   4200 ccatcgatgg tctgaaagaa gttcaggaag cggtgatgct gatagaagcc ggactgagta   4260
cctacgagaa agagtgcgca aaacgcggtg acgactatca ggaaattttt gcccagcagg   4320
tccgtgaaac gatggagcgc cgtgcagccg gtcttaaacc gcccgcctgg gcggctgcag   4380
catttgaatc cgggctgcga caatcaacag aggaggagaa gagtgacagc agagctgcgt   4440
aatctcccgc atattgccag catggccttt aatgagccgc tgatgcttga acccgcctat   4500
gcgcgggttt tcttttgtgc gcttgcaggc cagcttggga tcagcagcct gacggatgcg   4560
gtgtccggcg acagcctgac tgcccaggag gcactcgcga cgctggcatt atccggtgat   4620
gatgacggac cacgacaggc ccgcagttat caggtcatga acggcatcgc cgtgctgccg   4680
gtgtccggca cgctggtcag ccggacgcgg gcgctgcagc cgtactcggg gatgaccggt   4740
tacaacggca ttatcgcccg tctgcaacag gctgccagcg atccgatggt ggacggcatt   4800
ctgctcgata tggacacgcc cggcgggatg gtggcggggg catttgactg cgctgacatc   4860
atcgcccgtg tgcgtgacat aaaaccggta tgggcgcttg ccaacgacat gaactgcagt   4920
gcaggtcagt tgcttgccag tgccgcctcc cggcgtctgg tcacgcagac cgcccggaca   4980
ggctccatcg gcgtcatgat ggctcacagt aattacggtg ctgcgctgga gaaacagggt   5040
gtggaaatca cgctgattta cagcggcagc cataaggtgg atggcaaccc ctacagccat   5100
cttccggatg acgtccggga gacactgcag tcccggatgg acgcaacccg ccagatgttt   5160
gcgcagaagg tgtcggcata taccggcctg tccgtgcagg ttgtgctgga taccgaggct   5220
gcagtgtaca gcggtcagga ggccattgat gccggactgg ctgatgaact tgttaacagc   5280
accgatgcga tcaccgtcat gcgtgatgca ctggatgcac gtaaatcccg tctctcagga   5340
gggcgaatga ccaaagagac tcaatcaaca actgtttcag ccactgcttc gcaggctgac   5400
gttactgacg tggtgccagc gacggagggc gagaacgcca gcgcggcgca gccggacgtg   5460
aacgcgcaga tcaccgcagc ggttgcggca gaaaacagcc gcattatggg gatcctcaac   5520
tgtgaggagg ctcacggacg cgaagaacag gcacgcgtgc tggcagaaac ccccggtatg   5580
accgtgaaaa cggcccgccg cattctggcc gcagcaccac agagtgcaca ggcgcgcagt   5640
gacactgcgc tggatcgtct gatgcagggg gcaccggcac cgctggctgc aggtaacccg   5700
gcatctgatg ccgttaacga tttgctgaac acaccagtgt aagggatgtt tatgacgagc   5760
aaagaaacct ttacccatta ccagccgcag ggcaacagtg acccggctca taccgcaacc   5820
gcgcccggcg gattgagtgc gaaagcgcct gcaatgaccc cgctgatgct ggacacctcc   5880
agccgtaagc tggttgcgtg ggatggcacc accgacggtg ctgccgttgg cattcttgcg   5940
gttgctgctg accagaccag caccacgctg acgttctaca agtccggcac gttccgttat   6000
gaggatgtgc tctggccgga ggctgccagc gacgagacga aaaacggac gcgtttgcc   6060 ggaacggcaa tcagcatcgt ttaactttac ccttcatcac taaaggccgc ctgtgcggct   6120 tttttttacgg gatttttta tgtcgatgta cacaaccgcc caactgctgg cggcaaatga   6180
```

```
gcagaaattt aagtttgatc cgctgtttct gcgtctcttt ttccgtgaga gctatccctt      6240
caccacggag aaagtctatc tctcacaaat tccgggactg gtaaacatgg cgctgtacgt      6300
ttcgccgatt gtttccggtg aggttatccg ttcccgtggc ggctccacct ctgaatttac      6360
gccgggatat gtcaagccga agcatgaagt gaatccgcag atgaccctgc gtcgcctgcc      6420
ggatgaagat ccgcagaatc tggcggaccc ggcttaccgc cgccgtcgca tcatcatgca      6480
gaacatgcgt gacgaagagc tggccattgc tcaggtcgaa gagatgcagg cagtttctgc      6540
cgtgcttaag ggcaaataca ccatgaccgg tgaagccttc gatccggttg aggtggatat      6600
gggccgcagt gaggagaata acatcacgca gtccggcggc acggagtgga gcaagcgtga      6660
caagtccacg tatgacccga ccgacgatat cgaagcctac gcgctgaacg ccagcggtgt      6720
ggtgaatatc atcgtgttcg atccgaaagg ctgggcgctg ttccgttcct tcaaagccgt      6780
caaggagaag ctggataccc gtcgtggctc taattccgag ctggagacag cggtgaaaga      6840
cctgggcaaa gcggtgtcct ataagggat gtatggcgat gtggccatcg tcgtgtattc      6900
cggacagtac gtggaaaacg gcgtcaaaaa gaacttcctg ccggacaaca cgatggtgct      6960
ggggaacact caggcacgcg gtctgcgcac ctatggctgc attcaggatg cggacgcaca      7020
gcgcgaaggc attaacgcct ctgcccgtta cccgaaaaac tgggtgacca ccggcgatcc      7080
ggcgcgtgag ttcaccatga ttcagtcagc accgctgatg ctgctggctg accctgatga      7140
gttcgtgtcc gtacaactgg cgtaatcatg ccccttcggg gccattgttt ctctgtggag      7200
gagtccatga cgaaagatga actgattgcc cgtctccgct cgctgggtga caactgaac      7260 cgtgatgtca gcctgacggg gacgaaagaa gaactggcgc tccgtgtggc agagctgaaa      7320
gaggagcttg atgacacgga tgaaactgcc ggtcaggaca cccctctcag ccgggaaaat      7380
gtgctgaccg gacatgaaaa tgaggtggga tcagcgcagc cggataccgt gattctggat      7440
acgtctgaac tggtcacggt cgtggcactg gtgaagctgc atactgatgc acttcacgcc      7500
acgcgggatg aacctgtggc atttgtgctg ccggaacgg cgtttcgtgt ctctgccggt      7560
gtggcagccg aaatgacaga gcgcggcctg gccagaatgc aataacggga ggcgctgtgg      7620
ctgatttcga taacctgttc gatgctgcca ttgcccgcgc cgatgaaacg atacgcgggt      7680
acatgggaac gtcagccacc attacatccg gtgagcagtc aggtgcggtg atacgtggtg      7740
tttttgatga ccctgaaaat atcagctatg ccggacaggg cgtgcgcgtt gaaggctcca      7800
gcccgtccct gtttgtccgg actgatgagg tgcggcagct gcggcgtgga gacacgctga      7860
ccatcggtga ggaaaatttc tgggtagatc gggtttcgcc ggatgatggc ggaagttgtc      7920
atctctggct tggacggggc gtaccgcctg ccgttaaccg tcgccgctga aggggggatg      7980
tatggccata aaaggtcttg agcaggccgt tgaaaacctc agccgtatca gcaaaacggc      8040
ggtgcctggt gccgccgcaa tggccattaa ccgcgttgct tcatccgcga tatcgcagtc      8100
ggcgtcacag gttgcccgtg agacaaaggt acgccggaaa ctggtaaagg aaagggccag      8160
gctgaaaagg gccacggtca aaaatccgca ggccagaatc aaagttaacc gggggggattt      8220 gcccgtaatc aagctgggta atgcgcgggt tgtccttttcg cgccgcaggc gtcgtaaaaa      8280
ggggcagcgt tcatccctga aaggtggcgg cagcgtgctt gtggtgggta accgtcgtat      8340
tcccggcgcg tttattcagc aactgaaaaa tggccggtgg catgtcatgc agcgtgtggc      8400
tgggaaaaac cgttacccca ttgatgtggt gaaaatcccg atggcggtgc cgctgaccac      8460
ggcgtttaaa caaaatattg agcggatacg gcgtgaacgt cttccgaaag agctgggcta      8520
tgcgctgcag catcaactga ggatggtaat aaagcgatga acatactga actccgtgca      8580
```

```
gccgtactgg atgcactgga gaagcatgac accggggcga cgttttttga tggtcgcccc   8640
gctgttttg  atgaggcgga ttttccggca gttgccgttt atctcaccgg cgctgaatac   8700
acgggcgaag agctggacag cgatacctgg caggcggagc tgcatatcga agttttcctg   8760
cctgctcagg tgccggattc agagctggat gcgtggatgg agtcccggat ttatccggtg   8820
atgagcgata tcccggcact gtcagatttg atcaccagta tggtggccag cggctatgac   8880
taccggcgcg acgatgatgc gggcttgtgg agttcagccg atctgactta tgtcattacc   8940
tatgaaatgt gaggacgcta tgcctgtacc aaatcctaca atgccggtga aggtgccgg    9000
gaccaccctg tgggtttata aggggagcgg tgacccttac gcgaatccgc tttcagacgt   9060
tgactggtcg cgtctggcaa aagttaaaga cctgacgccc ggcgaactga ccgctgagtc   9120
ctatgacgac agctatctcg atgatgaaga tgcagactgg actgcgaccg ggcaggggca   9180
gaaatctgcc ggagatacca gcttcacgct ggcgtggatg cccggagagc aggggcagca   9240
ggcgctgctg cgcgtggttta tgaaggcga tacccgtgcc tataaaatcc gcttcccgaa   9300
cggcacggtc gatgtgttcc gtggctgggt cagcagtatc ggtaaggcgg tgacggcgaa   9360
ggaagtgatc acccgcacgg tgaaagtcac caatgtggga cgtccgtcga tggcagaaga   9420
tcgcagcacg gtaacagcgg caaccggcat gaccgtgacg cctgccagca cctcggtggt   9480
gaaagggcag agcaccacgc tgaccgtggc cttccagccc gagggcgtaa ccgacaagag   9540
ctttcgtgcg gtgtctgcgg ataaaacaaa agccaccgtg tcggtcagtg gtatgaccat   9600
caccgtgaac ggcgttgctg caggcaaggt caacattccg gttgtatccg gtaatggtga   9660
gtttgctgcg gttgcagaaa ttaccgtcac cgccagttaa tccggagagt cagcgatgtt   9720
cctgaaaacc gaatcatttg aacataacgg tgtgaccgtc acgctttctg aactgtcagc   9780
cctgcagcgc attgagcatc tcgccctgat gaaacggcag gcagaacagg cggagtcaga   9840
cagcaaccgg aagtttactg tggaagacgc catcagaacc ggcgcgtttc tggtggcgat   9900
gtccctgtgg cataaccatc gcagaagac gcagatgccg tccatgaatg aagccgttaa   9960
acagattgag caggaagtgc ttaccacctg gcccacggag gcaatttctc atgctgaaaa   10020
cgtggtgtac cggctgtctg gtatgtatga gtttgtggtg aataatgccc ctgaacagac   10080
agaggacgcc gggcccgcag agcctgtttc tgcgggaaag tgttcgacgg tgagctgagt   10140
tttgccctga aactgcgcg  tgagatgggg cgacccgact ggcgtgccat gcttgccggg   10200
atgtcatcca cggagtatgc cgactggcac cgcttttaca gtacccatta ttttcatgat   10260
gttctgctgg atatgcactt ttccgggctg acgtacaccg tgctcagcct gttttttcagc  10320
gatccggata tgcatccgct ggatttcagt ctgctgaacc ggcgcgaggc tgacgaagag   10380
cctgaagatg atgtgctgat gcagaaagcg gcagggcttg ccggaggtgt ccgctttggc   10440
ccggacggga atgaagttat ccccgcttcc ccggatgtgg cggacatgac ggaggatgac   10500
gtaatgctga tgacagtatc agaagggatc gcaggaggag tccggtatgg ctgaaccggt   10560
aggcgatctg gtcgttgatt tgagtctgga tgcggccaga tttgacgagc agatggccag   10620
agtcaggcgt catttttctg gtacggaaag tgatgcgaaa aaaacagcgg cagtcgttga   10680
acagtcgctg agccgacagg cgctggctgc acagaaagcg gggatttccg tcgggcagta   10740
taaagccgcc atgcgtatgc tgcctgcaca gttcaccgac gtggccacgc agcttgcagg   10800
cgggcaaagt ccgtggctga tcctgctgca acagggggg  caggtgaagg actccttcgg   10860
cgggatgatc cccatgttca gggggcttgc cggtgcgatc accctgccga tggtggggc   10920
cacctcgctg gcggtggcga ccggtgcgct ggcgtatgcc tggtatcagg gcaactcaac   10980
```

```
cctgtccgat ttcaacaaaa cgctggtcct ttccggcaat caggcgggac tgacggcaga    11040
tcgtatgctg gtcctgtcca gagccgggca ggcggcaggg ctgacgttta accagaccag    11100
cgagtcactc agcgcactgg ttaaggcggg ggtaagcggt gaggctcaga ttgcgtccat    11160
cagccagagt gtggcgcgtt tctcctctgc atccggcgtg gaggtggaca aggtcgctga    11220
agccttcggg aagctgacca cagacccgac gtcggggctg acggcgatgg ctcgccagtt    11280
ccataacgtg tcggcggagc agattgcgta tgttgctcag ttgcagcgtt ccggcgatga    11340
agccggggca ttgcaggcgg cgaacgaggc cgcaacgaaa gggtttgatg accagacccg    11400
ccgcctgaaa gagaacatgg gcacgctgga gacctgggca gacaggactg cgcgggcatt    11460
caaatccatg tgggatgcgg tgctggatat tggtcgtcct gataccgcgc aggagatgct    11520
gattaaggca gaggctgcgt ataagaaagc agacgacatc tggaatctgc gcaaggatga    11580
ttattttgtt aacgatgaag cgcgggcgcg ttactgggat gatcgtgaaa aggcccgtct    11640
tgcgcttgaa gccgcccgaa agaaggctga gcagcagact caacaggaca aaaatgcgca    11700
gcagcagagc gataccgaag cgtcacggct gaaatatacc gaagaggcgc agaaggctta    11760
cgaacggctg cagacgccgc tggagaaata taccgcccgt caggaagaac tgaacaaggc    11820
actgaaagac gggaaaatcc tgcaggcgga ttacaacacg ctgatggcgg cggcgaaaaa    11880
ggattatgaa gcgacgctga aaaagccgaa acagtccagc gtgaaggtgt ctgcgggcga    11940
tcgtcaggaa gacagtgctc atgctgccct gctgacgctt caggcagaac tccgacgct    12000 ggagaagcat gccggagcaa atgagaaaat cagccagcag cgccgggatt tgtggaaggc    12060
ggagagtcag ttcgcggtac tggaggaggc ggcgcaacgt cgccagctgt ctgcacagga    12120
gaaatccctg ctggcgcata agatgagac gctggagtac aaacgccagc tggctgcact    12180
tggcgacaag gttacgtatc aggagcgcct gaacgcgctg gcgcagcagg cggataaatt    12240
cgcacagcag caacgggcaa acgggccgc cattgatgcg aaaagccggg ggctgactga    12300
ccggcaggca gaacgggaag ccacggaaca gcgcctgaag gaacagtatg gcgataatcc    12360
gctggcgctg aataacgtca tgtcagagca gaaaaagacc tgggcggctg aagaccagct    12420
tcgcgggaac tggatggcag gcctgaagtc cggctggagt gagtgggaag agagcgccac    12480
ggacagtatg tcgcaggtaa aaagtgcagc cacgcagacc tttgatggta ttgcacagaa    12540
tatggcggcg atgctgaccg gcagtgagca gaactggcgc agcttcaccc gttccgtgct    12600
gtccatgatg acagaaattc tgcttaagca ggcaatggtg gggattgtcg ggagtatcgg    12660
cagcgccatt ggcggggctg ttggtggcgg cgcatccgcg tcaggcggta cagccattca    12720
ggccgctgcg gcgaaattcc attttgcaac cggaggattt acgggaaccg gcggcaaata    12780
tgagccagcg gggattgttc accgtggtga gtttgtcttc acgaaggagg caaccagccg    12840
gattggcgtg gggaatcttt accggctgat gcgcggctat gccaccggcg ttatgtcgg    12900 tacaccgggc agcatggcag acagccggtc gcaggcgtcc gggacgtttg agcagaataa    12960
ccatgtggtg attaacaacg acggcacgaa cgggcagata ggtccggctg ctctgaaggc    13020
ggtgtatgac atggcccgca agggtgcccg tgatgaaatt cagacacaga tgcgtgatgg    13080
tggcctgttc tccggaggtg gacgatgaag accttccgct ggaaagtgaa acccggtatg    13140
gatgtggctt cggtcccttc tgtaagaaag gtgcgctttg gtgatggcta ttctcagcga    13200
gcgcctgccg ggctgaatgc caacctgaaa acgtacagcg tgacgctttc tgtcccccgt    13260
gaggaggcca cggtactgga gtcgtttctg aagagcacg ggggctggaa atcctttctg    13320
tggacgccgc cttatgagtg gcggcagata aaggtgacct gcgcaaaatg gtcgtcgcgg    13380
```

```
gtcagtatgc tgcgtgttga gttcagcgca gagtttgaac aggtggtgaa ctgatgcagg    13440
atatccggca ggaaacactg aatgaatgca cccgtgcgga gcagtcggcc agcgtggtgc    13500
tctgggaaat cgacctgaca gaggtcggtg agaacgttat ttttttctgt aatgagcaga    13560
acgaaaaagg tgagccggtc acctggcagg ggcgacagta tcagccgtat cccattcagg    13620
ggagcggttt tgaactgaat ggcaaaggca ccagtacgcg ccccacgctg acggtttcta    13680
acctgtacgg tatggtcacc gggatggcgg aagatatgca gagtctggtc ggcggaacgg    13740
tggtccggcg taaggtttac gcccgttttc tggatgcggt gaacttcgtc aacggaaaca    13800
gttacgccga tccggagcag gaggtgatca gccgctggcg cattgagcag tgcagcgaac    13860
tgagcgcggt gagtgcctcc tttgtactgt ccacgccgac ggaaacggat ggcgctgttt    13920
ttccgggacg tatcatgctg gccaacacct gcacctggac ctatcgcggt gacgagtgcg    13980
gttatagcgg tccggctgtc gcggatgaat atgaccagcc aacgtccgat atcacgaagg    14040
ataaatgcag caaatgcctg agcggttgta agttccgcaa taacgtcggc aactttggcg    14100
gcttcctttc cattaacaaa ctttcgcagt aaatcccatg acacagacag aatcagcgat    14160
tctggcgcac gcccggcgat gtgcgccagc ggagtcgtgc ggcttcgtgg taagcacgcc    14220 ggaggggaa agatatttcc cctgcgtgaa tatctccggt gagccggagg cgtatttccg    14280
tatgtcgccg gaagactggc tgcaggcaga aatgcagggt gagattgtgg cgctggtcca    14340
cagccacccc ggtggtctgc cctggctgag tgaggccgac cggcggctgc aggtgcagag    14400
tgatttgccg tggtggctgg tctgccgggg gacgattcat aagttccgct gtgtgccgca    14460
tctcaccggg cggcgctttg agcacggtgt gacggactgt tacacactgt tccgggatgc    14520
ttatcatctg gcggggattg agatgccgga cttttcatcgt gaggatgact ggtggcgtaa    14580
cggccagaat ctctatctgg ataatctgga ggcgacgggg ctgtatcagg tgccgttgtc    14640
agcggcacag ccgggcgatg tgctgctgtg ctgttttggt tcatcagtgc cgaatcacgc    14700
cgcaatttac tgcggcgacg gcgagctgct gcaccatatt cctgaacaac tgagcaaacg    14760
agagaggtac accgacaaat ggcagcgacg cacacactcc ctctggcgtc accgggcatg    14820
gcgcgcatct gcctttacgg ggatttacaa cgatttggtc gccgcatcga ccttcgtgtg    14880
aaaacggggg ctgaagccat ccgggcactg gccacacagc tcccggcgtt tcgtcagaaa    14940
ctgagcgacg gctggtatca ggtacggatt gccgggcggg acgtcagcac gtccgggtta    15000
acggcgcagt tacatgagac tctgcctgat ggcgctgtaa ttcatattgt tcccagagtc    15060
gccggggcca agtcaggtgg cgtattccag attgtcctgg gggctgccgc cattgccgga    15120
tcattcttta ccgccggagc caccccttgca gcatgggggg cagccattgg ggccggtggt    15180
atgaccggca tcctgttttc tctcggtgcc agtatggtgc tcggtggtgt ggcgcagatg    15240
ctggcaccga aagccagaac tccccgtata cagacaacgg ataacggtaa gcagaacacc    15300
tatttctcct cactggataa catgttgcc cagggcaatg ttctgcctgt tctgtacggg    15360
gaaatgcgcg tggggtcacg cgtggttttct caggagatca gcacggcaga cgaagggggac    15420 ggtggtcagg ttgtggtgat tggtcgctga tgcaaaatgt tttatgtgaa accgcctgcg    15480
ggcggttttg tcatttatgg agcgtgagga atgggtaaag gaagcagtaa ggggcatacc    15540
ccgcgcgaag cgaaggacaa cctgaagtcc acgcagttgc tgagtgtgat cgatgccatc    15600
agcgaagggc cgattgaagg tccggtggat ggcttaaaaa gcgtgctgct gaacagtacg    15660
ccggtgctga cactgagggg gaataccaac atatccggtg tcacggtggt gttccgggct    15720
ggtgagcagg agcagactcc gccggaggga tttgaatcct ccggctccga cacggtgctg    15780
```

```
ggtacggaag tgaaatatga cacgccgatc acccgcacca ttacgtctgc aaacatcgac   15840
cgtctgcgct ttaccttcgg tgtacaggca ctggtggaaa ccacctcaaa gggtgacagg   15900
aatccgtcgg aagtccgcct gctggttcag atacaacgta acggtggctg ggtgacggaa   15960
aaagacatca ccattaaggg caaaaccacc tcgcagtatc tggcctcggt ggtgatgggt   16020
aacctgccgc cgcgcccgtt taatatccgg atgcgcagga tgacgccgga cagcaccaca   16080
gaccagctgc agaacaaaac gctctggtcg tcatacactg aaatcatcga tgtgaaacag   16140
tgctacccga acacggcact ggtcggcgtg caggtggact cggagcagtt cggcagccag   16200
caggtgagcc gtaattatca tctgcgcggg cgtattctgc aggtgccgtc gaactataac   16260
ccgcagacgc ggcaatacag cggtatctgg gacggaacgt ttaaaccggc atacagcaac   16320
aacatggcct ggtgtctgtg ggatatgctg acccatccgc gctacggcat ggggaaacgt   16380
cttggtgcgg cggatgtgga taaatgggcg ctgtatgtca tcggccagta ctgcgaccag   16440
tcagtgccgg acggctttgg cggcacggag ccgcgcatca cctgtaatgc gtacctgacc   16500
acacagcgta aggcgtggga tgtgctcagc gatttctgct cggcgatgcg ctgtatgccg   16560
gtatggaacg ggcagacgct gacgttcgtg caggaccgac cgtcggataa gacgtggacc   16620
tataaccgca gtaatgtggt gatgccggat gatggcgcgc cgttccgcta cagcttcagc   16680
gccctgaagg accgccataa tgccgttgag gtgaactgga ttgacccgaa caacggctgg   16740
gagacggcga cagagcttgt tgaagatacg caggccattg cccgttacgg tcgtaatgtt   16800
acgaagatgg atgcctttgg ctgtaccagc cggggggcagg cacaccgcgc cgggctgtgg   16860
ctgattaaaa cagaactgct ggaaacgcag accgtggatt tcagcgtcgg cgcagaaggg   16920
cttcgccatg taccgggcga tgttattgaa atctgcgatg atgactatgc cggtatcagc   16980
accggtggtc gtgtgctggc ggtgaacagc cagacccgga cgctgacgct cgaccgtgaa   17040
atcacgctgc catcctccgg taccgcgctg ataagcctgg ttgacggaag tggcaatccg   17100
gtcagcgtgg aggttcagtc cgtcaccgac ggcgtgaagg taaaagtgag ccgtgttcct   17160
gacggtgttg ctgaatacag cgtatgggag ctgaagctgc cgacgctgcg ccagcgactg   17220
ttccgctgcg tgagtatccg tgagaacgac gacggcacgt atgccatcac cgccgtgcag   17280
catgtgccgg aaaaagaggc catcgtggat aacggggcgc actttgacgg cgaacagagt   17340
ggcacggtga atggtgtcac gccgccagcg gtgcagcacc tgaccgcaga agtcactgca   17400
gacagcgggg aatatcaggt gctggcgcga tgggacacac cgaaggtggt gaagggcgtg   17460
agtttcctgc tccgtctgac cgtaacagcg gacgacggca gtgagcggct ggtcagcacg   17520
gcccggacga cggaaaccac ataccgcttc acgcaactgg cgctggggaa ctacaggctg   17580
acagtccggg cggtaaatgc gtgggggcag caggggcgatc cggcgtcggt atcgttccgg   17640
attgccgcac cggcagcacc gtcgaggatt gagctgacgc cgggctattt tcagataacc   17700
gccacgccgc atcttgccgt ttatgacccg acggtacagt ttgagttctg gttctcggaa   17760
aagcagattg cggatatcag acaggttgaa accagcacgc gttatcttgg tacggcgctg   17820
tactggatag ccgccagtat caatatcaaa ccgggccatg attattactt ttatatccgc   17880
agtgtgaaca ccgttggcaa atcggcattc gtggaggccg tcggtcgggc gagcgatgat   17940
gcggaaggtt acctggattt tttcaaaggc aagataaccg aatcccatct cggcaaggag   18000
ctgctggaaa aagtcgagct gacggaggat aacgccagca gactggagga gttttcgaaa   18060
gagtggaagg atgccagtga taagtggaat gccatgtggg ctgtcaaaat tgagcagacc   18120
aaagacggca acattatgt cgcgggtatt ggcctcagca tggaggacac ggaggaaggc   18180
```

```
aaactgagcc agtttctggt tgccgccaat cgtatcgcat ttattgaccc ggcaaacggg    18240
aatgaaacgc cgatgtttgt ggcgcagggc aaccagatat tcatgaacga cgtgttcctg    18300
aagcgcctga cggcccccac cattaccagc ggcggcaatc ctccggcctt tccctgaca     18360 ccggacggaa agctgaccgc taaaaatgcg gatatcagtg gcagtgtgaa tgcgaactcc    18420
gggacgctca gtaatgtgac gatagctgaa aactgtacga taaacggtac gctgagggcg    18480
gaaaaaatcg tcggggacat tgtaaaggcg gcgagcgcgg cttttccgcg ccagcgtgaa    18540
agcagtgtgg actggccgtc aggtacccgt actgtcaccg tgaccgatga ccatccttttt  18600 gatcgccaga tagtggtgct tccgctgacg tttcgcggaa gtaagcgtac tgtcagcggc    18660
aggacaacgt attcgatgtg ttatctgaaa gtactgatga acggtgcggt gatttatgat    18720
ggcgcggcga acgaggcggt acaggtgttc tcccgtattg ttgacatgcc agcgggtcgg    18780
ggaaacgtga tcctgacgtt cacgcttacg tccacacggc attcggcaga tattccgccg    18840
tatacgtttg ccagcgatgt gcaggttatg gtgattaaga acaggcgct gggcatcagc     18900 gtggtctgag tgtgttacag aggttcgtcc gggaacgggc gttttattat aaaacagtga    18960
gaggtgaacg atgcgtaatg tgtgtattgc cgttgctgtc tttgccgcac ttgcggtgac    19020
agtcactccg gcccgtgcgg aaggtggaca tggtacgttt acggtgggct attttcaagt    19080
gaaaccgggt acattgccgt cgttgtcggg cggggatacc ggtgtgagtc atctgaaagg    19140
gattaacgtg aagtaccgtt atgagctgac ggacagtgtg ggggtgatgg cttccctggg    19200
gttcgccgcg tcgaaaaaga gcagcacagt gatgaccggg gaggatacgt ttcactatga    19260
gagcctgcgt ggacgttatg tgagcgtgat ggccggaccg gttttacaaa tcagtaagca    19320
ggtcagtgcg tacgccatgg ccggagtggc tcacagtcgg tggtccggca gtacaatgga    19380
ttaccgtaag acgaaatca ctcccgggta tatgaaagag acgaccactg ccagggacga     19440
aagtgcaatg cggcataccct cagtggcgtg gagtgcaggt atacagatta tccggcagc    19500 gtccgtcgtt gttgatattg cttatgaagg ctccggcagt ggcgactggc gtactgacgg    19560
attcatcgtt ggggtcggtt ataaattctg attagccagg taacacagtg ttatgacagc    19620
ccgccggaac cggtgggctt ttttgtgggg tgaatatggc agtaaagatt tcaggagtcc    19680
tgaaagacgg cacaggaaaa ccggtacaga actgcaccat tcagctgaaa gccagacgta    19740
acagcaccac ggtggtggtg aacacggtgg gctcagagaa tccggatgaa gccgggcgtt    19800
acagcatgga tgtggagtac ggtcagtaca gtgtcatcct gcaggttgac ggttttccac    19860
catcgcacgc cgggaccatc accgtgtatg aagattcaca accggggacg ctgaatgatt    19920
ttctctgtgc catgacggag gatgatgccc ggccggaggt gctgcgtcgt cttgaactga    19980
tggtggaaga ggtggcgcgt aacgcgtccg tggtggcaca gagtacggca gacgcgaaga    20040
aatcagccgg cgatgccagt gcatcagctg ctcaggtcgc ggcccttgtg actgatgcaa    20100
ctgactcagc acgcgccgcc agcacgtccg ccggacaggc tgcatcgtca gctcaggaag    20160
cgtcctccgg cgcagaagcg gcatcagcaa aggccactga agcggaaaaa agtgccgcag    20220
ccgcagagtc ctcaaaaaac gcggcggcca ccagtgccgg tgcggcgaaa acgtcagaaa    20280
cgaatgctgc agcgtcacaa caatcagccg ccacgtctgc ctccaccgcg ccacgaaag    20340 cgtcagaggc cgccacttca gcacgagatg cggtggcctc aaaagaggca gcaaaatcat    20400
cagaaacgaa cgcatcatca agtgccggtc gtgcagcttc ctcggcaacg gcggcagaaa    20460
attctgccag ggcggcaaaa acgtccgaga cgaatgccag gtcatctgaa acagcagcgg    20520
aacggagcgc ctctgccgcg gcagacgcaa aaacagcggc ggcggggagt gcgtcaacgg    20580
```

```
catccacgaa ggcgacagag gctgcgggaa gtgcggtatc agcatcgcag agcaaaagtg    20640
cggcagaagc ggcggcaata cgtgcaaaaa attcggcaaa acgtgcagaa gatatagctt    20700
cagctgtcgc gcttgaggat gcggacacaa cgagaaaggg gatagtgcag ctcagcagtg    20760
caaccaacag cacgtctgaa acgcttgctg caacgccaaa ggcggttaag gtggtaatgg    20820
atgaaacgaa cagaaaagcc cactggacag tccggcactg accggaacgc caacagcacc    20880
aaccgcgctc aggggaacaa acaatacccc gattgcgaac accgcttttg tactggccgc    20940
gattgcagat gttatcgacg cgtcacctga cgcactgaat acgctgaatg aactggccgc    21000
agcgctcggg aatgatccag attttgctac caccatgact aacgcgcttg cgggtaaaca    21060
accgaagaat gcgacactga cggcgctggc agggctttcc acggcgaaaa ataaattacc    21120
gtattttgcg gaaaatgatg ccgccagcct gactgaactg actcaggttg cagggatat    21180 tctggcaaaa aattccgttg cagatgttct tgaataccct tggggccggtg agaattcggc    21240 cttttccggca ggtgcgccga tcccgtggcc atcagatatc gttccgtctg gctacgtcct    21300
gatgcagggg caggcgtttg acaaatcagc ctacccaaaa cttgctgtcg cgtatccatc    21360
gggtgtgctt cctgatatgc gaggctggac aatcaagggg aaacccgcca gcggtcgtgc    21420
tgtattgtct caggaacagg atggaattaa gtcgcacacc cacagtgcca gtgcatccgg    21480
tacggatttg gggacgaaaa ccacatcgtc gtttgattac gggacgaaaa caacaggcag    21540
tttcgattac ggcaccaaat cgacgaataa acgggggct catgctcaca gtctgagcgg    21600
ttcaacaggg gccgcgggtg ctcatgccca cacaagtggt ttaaggatga acagttctgg    21660
ctggagtcag tatggaacag caaccattac aggaagttta tccacagtta aaggaaccag    21720
cacacagggt attgcttatt tatcgaaaac ggacagtcag ggcagccaca gtcactcatt    21780
gtccggtaca gccgtgagtg ccggtgcaca tgcgcataca gttggtattg gtgcgcacca    21840
gcatccggtt gttatcggtg ctcatgccca ttctttcagt attggttcac acggacacac    21900
catcaccgtt aacgctgcgg gtaacgcgga aaacaccgtc aaaaacattg catttaacta    21960
tattgtgagg cttgcataat ggcattcaga atgagtgaac aaccacggac cataaaaatt    22020
tataatctgc tggccggaac taatgaattt attggtgaag gtgacgcata tattccgcct    22080
cataccggtc tgcctgcaaa cagtaccgat attgcaccgc cagatattcc ggctggcttt    22140
gtggctgttt tcaacagtga tgaggcatcg tggcatctcg ttgaagacca tcggggtaaa    22200
accgtctatg acgtggcttc cggcgacgcg ttatttattt ctgaactcgg tccgttaccg    22260
gaaaatttta cctggttatc gccgggaggg gaatatcaga agtggaacgg cacagcctgg    22320
gtgaaggata cggaagcaga aaaactgttc cggatccggg aggcggaaga aacaaaaaaa    22380
agcctgatgc aggtagccag tgagcatatt gcgccgcttc aggatgctgc agatctggaa    22440
attgcaacga aggaagaaac ctcgttgctg aagcctgga agaagtatcg ggtgttgctg    22500
aaccgtgttg atacatcaac tgcacctgat attgagtggc ctgctgtccc tgttatggag    22560
taatcgtttt gtgatatgcc gcagaaacgt tgtatgaaat aacgttctgc ggttagttag    22620
tatattgtaa agctgagtat tggtttattt ggcgattatt atcttcagga gaataatgga    22680
agttctatga ctcaattgtt catagtgttt acatcaccgc caattgcttt taagactgaa    22740
cgcatgaaat atggtttttc gtcatgtttt gagtctgctg ttgatatttc taaagtcggt    22800
ttttttcctt cgttttctct aactatttttc catgaaatac attttgtgatt attatttgaa    22860 tcaattccaa ttacctgaag tctttcatct ataattggca ttgtatgtat tggtttattg    22920
gagtagatgc ttgcttttct gagccatagc tctgatatcc aaatgaagcc ataggcattt    22980
```

```
gttattttgg ctctgtcagc tgcataacgc caaaaaatat atttatctgc ttgatcttca    23040
aatgttgtat tgattaaatc aattggatgg aattgtttat cataaaaaat taatgtttga    23100
atgtgataac cgtcctttaa aaaagtcgtt tctgcaagct tggctgtata gtcaactaac    23160
tcttctgtcg aagtgatatt tttaggctta tctaccagtt ttagacgctc tttaatatct    23220
tcaggaatta ttttattgtc atattgtatc atgctaaatg acaatttgct tatggagtaa    23280
tcttttaatt ttaaataagt tattctcctg gcttcatcaa ataaagagtc gaatgatgtt    23340
ggcgaaatca catcgtcacc cattggattg tttatttgta tgccaagaga gttacagcag    23400
ttatacattc tgccatagat tatagctaag gcatgtaata attcgtaatc ttttagcgta    23460
ttagcgaccc atcgtctttc tgatttaata atagatgatt cagttaaata tgaaggtaat    23520
ttcttttgtg caagtctgac taactttttt ataccaatgt ttaacatact ttcatttgta    23580
ataaactcaa tgtcattttc ttcaatgtaa gatgaaataa gagtagcctt tgcctcgcta    23640
tacatttcta aatcgccttg ttttctatc gtattgcgag aatttttagc ccaagccatt    23700
aatggatcat ttttccattt ttcaataaca ttattgttat accaaatgtc atatcctata    23760
atctggtttt tgttttttg aataataaat gttactgttc ttgcggtttg gaggaattga    23820
ttcaaattca agcgaaataa ttcagggtca aaatatgtat caatgcagca tttgagcaag    23880
tgcgataaat ctttaagtct tcttttcccat ggttttttag tcataaaact ctccattttg    23940
ataggttgca tgctagatgc tgatatattt tagaggtgat aaaattaact gcttaactgt    24000
caatgtaata caagttgttt gatctttgca atgattctta tcagaaacca tatagtaaat    24060
tagttacaca ggaaattttt aatattatta ttatcattca ttatgtatta aaattagagt    24120
tgtggcttgg ctctgctaac acgttgctca taggagatat ggtagagccg cagacacgtc    24180
gtatgcagga acgtgctgcg gctggctggt gaacttccga tagtgcgggt gttgaatgat    24240
ttccagttgc taccgatttt acatattttt tgcatgagag aatttgtacc acctcccacc    24300
gaccatctat gactgtacgc cactgtccct aggactgcta tgtgccggag cggacattac    24360
aaacgtcctt ctcggtgcat gccactgttg ccaatgacct gcctaggaat tggttagcaa    24420
gttactaccg gattttgtaa aaacagcccct cctcatataa aaagtattcg ttcacttccg    24480
ataagcgtcg taattttcta tctttcatca tattctagat ccctctgaaa aaatcttccg    24540
agtttgctag gcactgatac ataactcttt tccaataatt ggggaagtca ttcaaatcta    24600
taataggttt cagatttgct tcaataaatt ctgactgtag ctgctgaaac gttgcggttg    24660
aactatattt ccttataact tttacgaaag agtttctttg agtaatcact tcactcaagt    24720
gcttccctgc ctccaaacga tacctgttag caatatttaa tagcttgaaa tgatgaagag    24780
ctctgtgttt gtcttcctgc ctccagttcg ccgggcattc aacataaaaa ctgatagcac    24840
ccggagttcc ggaaacgaaa tttgcatata cccattgctc acgaaaaaaa atgtccttgt    24900
cgatataggg atgaatcgct tggtgtacct catctactgc gaaaacttga cctttctctc    24960
ccatattgca gtcgcggcac gatggaacta aattaatagg catcaccgaa aattcaggat    25020
aatgtgcaat aggaagaaaa tgatctatat tttttgtctg tcctatatca ccacaaaatg    25080 gacattttc acctgatgaa acaagcatgt catcgtaata tgttctagcg ggtttgtttt    25140
tatctcggag attattttca taaagctttt ctaatttaac ctttgtcagg ttaccaacta    25200
ctaaggttgt aggctcaaga gggtgtgtcc tgtcgtaggt aaataactga cctgtcgagc    25260
ttaatattct atattgttgt tctttctgca aaaaagtggg gaagtgagta atgaaattat    25320
ttctaacatt tatctgcatc ataccttccg agcatttatt aagcatttcg ctataagttc    25380
```

-continued

```
tcgctggaag aggtagttttt ttcattgtac tttaccttca tctctgttca ttatcatcgc    25440
ttttaaaacg gttcgacctt ctaatcctat ctgaccatta taattttta gaatggtttc     25500 ataagaaagc tctgaatcaa cggactgcga taataagtgg tggtatccag aatttgtcac    25560
ttcaagtaaa aacacctcac gagttaaaac acctaagttc tcaccgaatg tctcaatatc    25620
cggacggata atatttattg cttctcttga ccgtaggact ttccacatgc aggattttgg    25680
aacctcttgc agtactactg gggaatgagt tgcaattatt gctacaccat tgcgtgcatc    25740
gagtaagtcg cttaatgttc gtaaaaagc agagagcaaa ggtggatgca gatgaacctc     25800
tggttcatcg aataaaacta atgacttttc gccaacgaca tctactaatc ttgtgatagt    25860
aaataaaaca attgcatgtc cagagctcat tcgaagcaga tatttctgga tattgtcata    25920
aaacaattta gtgaatttat catcgtccac ttgaatctgt ggttcattac gtcttaactc    25980
ttcatattta gaaatgaggc tgatgagttc catatttgaa aagttttcat cactacttag    26040 tttttgata gcttcaagcc agagttgtct ttttctatct actctcatac aaccaataaa     26100
tgctgaaatg aattctaagc ggagatcgcc tagtgatttt aaactattgc tggcagcatt    26160
cttgagtcca atataaaagt attgtgtacc ttttgctggg tcaggttgtt ctttaggagg    26220
agtaaaagga tcaaatgcac taaacgaaac tgaaacaagc gatcgaaaat atcccttggg    26280
gattcttgac tcgataagtc tattattttc agagaaaaaa tattcattgt tttctgggtt    26340
ggtgattgca ccaatcattc cattcaaaat tgttgtttta ccacacccat tccgcccgat    26400
aaaagcatga atgttcgtgc tgggcataga attaaccgtc acctcaaaag gtatagttaa    26460
atcactgaat ccgggagcac tttttctatt aaatgaaaag tggaaatctg acaattctgg    26520
caaaccattt aacacacgtg cgaactgtcc atgaatttct gaaagagtta cccctctaag    26580
taatgaggtg ttaaggacgc tttcattttc aatgtcggct aatcgatttg gccatactac    26640
taaatcctga atagctttaa gaaggttatg tttaaaacca tcgcttaatt tgctgagatt    26700
aacatagtag tcaatgcttt cacctaagga aaaaaacatt tcagggagtt gactgaattt    26760
tttatctatt aatgaataag tgcttacttc ttcttttttga cctacaaaac caattttaac    26820
atttccgata tcgcatttttt caccatgctc atcaaagaca gtaagataaa acattgtaac    26880
aaaggaatag tcattccaac catctgctcg taggaatgcc ttattttttt ctactgcagg    26940
aatatacccg cctctttcaa taacactaaa ctccaacata tagtaaccct taattttatt    27000
aaaataaccg caatttattt ggcggcaaca caggatctct cttttaagtt actctctatt    27060
acatacgttt tccatctaaa aattagtagt attgaactta acggggcatc gtattgtagt    27120
tttccatatt tagctttctg cttccttttg gataacccac tgttattcat gttgcatggt    27180
gcactgttta taccaacgat atagtctatt aatgcatata tagtatcgcc gaacgattag    27240
ctcttcaggc ttctgaagaa gcgtttcaag tactaataag ccgatagata gccacggact    27300
tcgtagccat ttttcataag tgttaacttc cgctcctcgc tcataacaga cattcactac    27360
agttatggcg gaaaggtatg catgctgggt gtggggaagt cgtgaaagaa aagaagtcag    27420
ctgcgtcgtt tgacatcact gctatcttct tactggttat gcaggtcgta gtgggtggca    27480
cacaaagctt tgcactggat tgcgaggctt tgtgcttctc tggagtgcga caggtttgat    27540
gacaaaaaat tagcgcaaga agacaaaaat caccttgcgc taatgctctg ttacaggtca    27600
ctaataccat ctaagtagtt gattcatagt gactgcatat gttgtgtttt acagtattat    27660
gtagtctgtt ttttatgcaa aatctaattt aatatattga tatttatatc attttacgtt    27720
tctcgttcag cttttttata ctaagttggc attataaaaa agcattgctt atcaatttgt    27780
```

```
tgcaacgaac aggtcactat cagtcaaaat aaaatcatta tttgatttca attttgtccc   27840
actccctgcc tctgtcatca cgatactgtg atgccatggt gtccgactta tgcccgagaa   27900
gatgttgagc aaacttatcg cttatctgct tctcatagag tcttgcagac aaactgcgca   27960
actcgtgaaa ggtaggcgga tccccttcga aggaaagacc tgatgctttt cgtgcgcgca   28020
taaaatacct tgatactgtg ccggatgaaa gcggttcgcg acgagtagat gcaattatgg   28080
tttctccgcc aagaatctct ttgcatttat caagtgtttc cttcattgat attccgagag   28140
catcaatatg caatgctgtt gggatggcaa ttttacgcc tgttttgctt tgctcgacat   28200
aaagatatcc atctacgata tcagaccact tcatttcgca taaatcacca actcgttgcc   28260
cggtaacaac agccagttcc attgcaagtc tgagccaaca tggtgatgat tctgctgctt   28320
gataaatttt caggtattcg tcagccgtaa gtcttgatct ccttacctct gattttgctg   28380
cgcgagtggc agcgacatgg tttgttgtta tatggccttc agctattgcc tctcggaatg   28440
catcgctcag tgttgatctg attaacttgg ctgacgccgc cttgccctcg tctatgtatc   28500
cattgagcat tgccgcaatt tcttttgtgg tgatgtcttc aagtggagca tcaggcagac   28560
ccctccttat tgctttaatt ttgctcatgt aatttatgag tgtcttctgc ttgattcctc   28620
tgctggccag gattttttcg tagcgatcaa gccatgaatg taacgtaacg gaattatcac   28680
tgttgattct cgctgtcaga ggcttgtgtt tgtgtcctga aaataactca atgttggcct   28740
gtatagcttc agtgattgcg attcgcctgt ctctgcctaa tccaaactct ttacccgtcc   28800
ttgggtccct gtagcagtaa tatccattgt ttcttatata aaggttaggg ggtaaatccc   28860
ggcgctcatg acttcgcctt cttcccattt ctgatcctct tcaaaaggcc acctgttact   28920
ggtcgattta agtcaacctt taccgctgat tcgtggaaca gatactctct tccatcctta   28980
accggaggtg gaatatcct gcattcccga acccatcgac gaactgtttc aaggcttctt   29040
ggacgtcgct ggcgtgcgtt ccactcctga agtgtcaagt acatcgcaaa gtctccgcaa   29100
ttacacgcaa gaaaaaaccg ccatcaggcg gcttggtgtt ctttcagttc ttcaattcga   29160
atattggtta cgtctgcatg tgctatctgc gcccatatca tccagtggtc gtagcagtcg   29220
ttgatgttct ccgcttcgat aactctgttg aatggctctc cattccattc tcctgtgact   29280
cggaagtgca tttatcatct ccataaaaca aaacccgccg tagcgagttc agataaaata   29340
aatccccgcg agtgcgagga ttgttatgta atattgggtt taatcatcta tatgttttgt   29400
acagagaggg caagtatcgt ttccaccgta ctcgtgataa taattttgca cggtatcagt   29460
catttctcgc acattgcaga atggggattt gtcttcatta gacttataaa ccttcatgga   29520
atatttgtat gccgactcta tatctatacc ttcatctaca taaacacctt cgtgatgtct   29580
gcatggagac aagacaccgg atctgcacaa cattgataac gcccaatctt tttgctcaga   29640
ctctaactca ttgatactca tttataaact ccttgcaatg tatgtcgttt cagctaaacg   29700
gtatcagcaa tgtttatgta aagaaacagt aagataatac tcaacccgat gtttgagtac   29760
ggtcatcatc tgacactaca gactctggca tcgctgtgaa gacgacgcga aattcagcat   29820
tttcacaagc gttatctttt acaaaaccga tctcactctc ctttgatgcg aatgccagcg   29880
tcagacatca tatgcagata ctcacctgca tcctgaaccc attgacctcc aaccccgtaa   29940
tagcgatgcg taatgatgtc gatagttact aacgggtctt gttcgattaa ctgccgcaga   30000
aactcttcca ggtcaccagt gcagtgcttg ataacaggag tcttcccagg atggcgaaca   30060
acaagaaact ggtttccgtc ttcacggact tcgttgcttt ccagtttagc aatacgctta   30120
ctcccatccg agataacacc ttcgtaatac tcacgctgct cgttgagttt tgattttgct   30180
```

```
gtttcaagct caacacgcag tttccctact gttagcgcaa tatcctcgtt ctcctggtcg   30240
cggcgtttga tgtattgctg gtttcttttcc cgttcatcca gcagttccag cacaatcgat   30300
ggtgttacca attcatggaa aaggtctgcg tcaaatcccc agtcgtcatg cattgcctgc   30360
tctgccgctt cacgcagtgc ctgagagtta atttcgctca cttcgaacct ctctgtttac   30420
tgataagttc cagatcctcc tggcaacttg cacaagtccg acaaccctga acgaccaggc   30480
gtcttcgttc atctatcgga tcgccacact cacaacaatg agtggcagat atagcctggt   30540
ggttcaggcg gcgcatttt attgctgtgt tgcgctgtaa ttcttctatt tctgatgctg   30600
aatcaatgat gtctgccatc tttcattaat ccctgaactg ttggttaata cgcttgaggg   30660
tgaatgcgaa taataaaaaa ggagcctgta gctccctgat gattttgctt ttcatgttca   30720
tcgttcctta aagacgccgt ttaacatgcc gattgccagg cttaaatgag tcggtgtgaa   30780
tcccatcagc gttaccgttt cgcggtgctt cttcagtacg ctacggcaaa tgtcatcgac   30840 gttttatcc ggaaactgct gtctggcttt ttttgatttc agaattagcc tgacgggcaa   30900
tgctgcgaag ggcgttttcc tgctgaggtg tcattgaaca agtccatgt cggcaagcat   30960 aagcacacag aatatgaagc ccgctgccag aaaaatgcat tccgtggttg tcatacctgg   31020
tttctctcat ctgcttctgc tttcgccacc atcatttcca gcttttgtga aagggatgcg   31080
gctaacgtat gaaattcttc gtctgttct actggtattg gcacaaacct gattccaatt   31140
tgagcaaggc tatgtgccat ctcgatactc gttcttaact caacagaaga tgctttgtgc   31200
atacagcccc tcgtttatta tttatctcct cagccagccg ctgtgctttc agtggatttc   31260
ggataacaga aaggccggga aatacccagc ctcgctttgt aacggagtag acgaaagtga   31320
ttgcgcctac ccggatatta tcgtgaggat gcgtcatcgc cattgctccc caaatacaaa   31380
accaatttca gccagtgcct cgtccatttt ttcgatgaac tccggcacga tctcgtcaaa   31440
actcgccatg tacttttcat cccgctcaat cacgacataa tgcaggcctt cacgcttcat   31500
acgcgggtca tagttggcaa agtaccaggc attttttcgc gtcacccaca tgctgtactg   31560
cacctgggcc atgtaagctg actttatggc ctcgaaacca ccgagccgga acttcatgaa   31620
atcccgggag gtaaacgggc atttcagttc aaggccgttg ccgtcactgc ataaaccatc   31680
gggagagcag gcggtacgca tactttcgtc gcgatagatg atcggggatt cagtaacatt   31740
cacgccggaa gtgaattcaa acagggttct ggcgtcgttc tcgtactgtt ttccccaggc   31800
cagtgcttta gcgttaactt ccggagccac accggtgcaa acctcagcaa gcagggtgtg   31860
gaagtaggac atttttcatgt caggccactt cttttccggag cggggttttg ctatcacgtt   31920
gtgaacttct gaagcggtga tgacgccgag ccgtaatttg tgccacgcat catccccctg   31980
ttcgacagct ctcacatcga tcccggtacg ctgcaggata atgtccggtg tcatgctgcc   32040
accttctgct ctgcggcttt ctgtttcagg aatccaagag cttttactgc ttcggcctgt   32100
gtcagttctg acgatgcacg aatgtcgcgg cgaaatatct gggaacagag cggcaataag   32160
tcgtcatccc atgttttatc cagggcgatc agcagagtgt taatctcctg catggtttca   32220
tcgttaaccg gagtgatgtc gcgttccggc tgacgttctg cagtgtatgc agtattttcg   32280
acaatgcgct cggcttcatc cttgtcatag ataccagcaa atccgaaggc cagacgggca   32340
cactgaatca tggctttatg acgtaacatc cgtttgggat gcgactgcca cggccccgtg   32400
atttctctgc cttcgcgagt tttgaatggt tcgcggcggc attcatccat ccattcggta   32460
acgcagatcg gatgattacg gtccttgcgg taaatccggc atgtacagga ttcattgtcc   32520
tgctcaaagt ccatgccatc aaactgctgg ttttcattga tgatgcggga ccagccatca   32580
```

```
acgcccacca ccggaacgat gccattctgc ttatcaggaa aggcgtaaat ttctttcgtc    32640
cacggattaa ggccgtactg gttggcaacg atcagtaatg cgatgaactg cgcatcgctg    32700
gcatcacctt taaatgccgt ctggcgaaga gtggtgatca gttcctgtgg gtcgacagaa    32760
tccatgccga cacgttcagc cagcttccca gccagcgttg cgagtgcagt actcattcgt    32820 tttataccte tgaatcaata tcaacctggt ggtgagcaat ggtttcaacc atgtaccgga    32880
tgtgttctgc catgcgctcc tgaaactcaa catcgtcatc aaacgcacgg gtaatggatt    32940
ttttgctggc cccgtggcgt tgcaaatgat cgatgcatag cgattcaaac aggtgctggg    33000
gcaggccttt ttccatgtcg tctgccagtt ctgcctcttt ctcttcacgg gcgagctgct    33060
ggtagtgacg cgcccagctc tgagcctcaa gacgatcctg aatgtaataa gcgttcatgg    33120
ctgaactcct gaaatagctg tgaaaatatc gcccgcgaaa tgccgggctg attaggaaaa    33180
caggaaaggg ggttagtgaa tgcttttgct tgatctcagt ttcagtatta atatccattt    33240
tttataagcg tcgacggctt cacgaaacat cttttcatcg ccaataaaag tggcgatagt    33300
gaatttagtc tggatagcca taagtgtttg atccattctt tgggactcct ggctgattaa    33360
gtatgtcgat aaggcgtttc catccgtcac gtaatttacg ggtgattcgt tcaagtaaag    33420
attcggaagg gcagccagca acaggccacc ctgcaatggc atattgcatg gtgtgctcct    33480
tatttataca taacgaaaaa cgcctcgagt gaagcgttat tggtatgcgg taaaaccgca    33540
ctcaggcggc cttgatagtc atatcatctg aatcaaatat tcctgatgta tcgatatcgg    33600
taattcttat tccttcgcta ccatccattg gaggccatcc ttcctgacca tttccatcat    33660
tccagtcgaa ctcacacaca acaccatatg catttaagtc gcttgaaatt gctataagca    33720
gagcatgttg cgccagcatg attaatacag catttaatac agagccgtgt ttattgagtc    33780
ggtattcaga gtctgaccag aaattattaa tctggtgaag ttttcctct gtcattacgt     33840 catggtcgat ttcaatttct attgatgctt tccagtcgta atcaatgatg tattttttga    33900
tgtttgacat ctgttcatat cctcacagat aaaaaatcgc cctcacactg gagggcaaag    33960
aagatttcca ataatcagaa caagtcggct cctgtttagt tacgagcgac attgctccgt    34020
gtattcactc gttggaatga atacacagtg cagtgtttat tctgttattt atgccaaaaa    34080
taaaggccac tatcaggcag ctttgttgtt ctgtttacca agttctctgg caatcattgc    34140
cgtcgttcgt attgcccatt tatcgacata tttcccatct tccattacag gaaacatttc    34200
ttcaggctta accatgcatt ccgattgcag cttgcatcca ttgcatcgct tgaattgtcc    34260
acaccattga ttttttatcaa tagtcgtagt catacggata gtcctggtat tgttccatca    34320
catcctgagg atgctcttcg aactcttcaa attcttcttc catatatcac cttaaatagt    34380
ggattgcggt agtaaagatt gtgcctgtct tttaaccaca tcaggctcgg tggttctcgt    34440 gtaccctac agcgagaaat cggataaact attacaaccc ctacagtttg atgagtatag     34500
aaatggatcc actcgttatt ctcggacgag tgttcagtaa tgaacctctg gagagaacca    34560
tgtatatgat cgttatctgg gttggacttc tgcttttaag cccagataac tggcctgaat    34620
atgttaatga gagaatcggt attcctcatg tgtggcatgt tttcgtcttt gctcttgcat    34680
tttcgctagc aattaatgtg catcgattat cagctattgc cagcgccaga tataagcgat    34740
ttaagctaag aaaacgcatt aagatgcaaa acgataaagt gcgatcagta attcaaaacc    34800
ttacagaaga gcaatctatg gttttgtgcg cagcccttaa tgaaggcagg aagtatgtgg    34860
ttacatcaaa acaattccca tacattagtg agttgattga gcttggtgtg ttgaacaaaa    34920 cttttttcccg atggaatgga aagcatatat tattccctat tgaggatatt tactggactg    34980
```

```
aattagttgc cagctatgat ccatataata ttgagataaa gccaaggcca atatctaagt    35040
aactagataa gaggaatcga ttttcccctta attttctggc gtccactgca tgttatgccg    35100
cgttcgccag gcttgctgta ccatgtgcgc tgattcttgc gctcaatacg ttgcaggttg    35160
ctttcaatct gtttgtggta ttcagccagc actgtaaggt ctatcggatt tagtgcgctt    35220
tctactcgtg atttcggttt gcgattcagc gagagaatag ggcggttaac tggttttgcg    35280
cttaccccaa ccaacagggg atttgctgct ttccattgag cctgtttctc tgcgcgacgt    35340
tcgcggcggc gtgtttgtgc atccatctgg attctcctgt cagttagctt tggtggtgtg    35400
tggcagttgt agtcctgaac gaaaaccccc cgcgattggc acattggcag ctaatccgga    35460
atcgcactta cggccaatgc ttcgtttcgt atcacacacc ccaaagcctt ctgctttgaa    35520
tgctgccctt cttcagggct taatttttaa gagcgtcacc ttcatggtgg tcagtgcgtc    35580
ctgctgatgt gctcagtatc accgccagtg gtatttatgt caacaccgcc agagataatt    35640
tatcaccgca gatggttatc tgtatgtttt ttatatgaat ttatttttttg caggggggca    35700 ttgtttggta ggtgagagat ctgaattgct atgtttagtg agttgtatct atttattttt    35760
caataaatac aattggttat gtgttttggg ggcgatcgtg aggcaaagaa aacccggcgc    35820
tgaggccggg ttattcttgt tctctggtca aattatatag ttggaaaaca aggatgcata    35880
tatgaatgaa cgatgcagag gcaatgccga tggcgatagt gggtatcatg tagccgctta    35940
tgctggaaag aagcaataac ccgcagaaaa acaaagctcc aagctcaaca aaactaaggg    36000
catagacaat aactaccgat gtcatatacc catactctct aatcttggcc agtcggcgcg    36060
ttctgcttcc gattagaaac gtcaaggcag caatcaggat tgcaatcatg gttcctgcat    36120
atgatgacaa tgtcgcccca agaccatctc tatgagctga aaagaaaca ccaggaatgt    36180 agtggcggaa aaggagatag caaatgctta cgataacgta aggaattatt actatgtaaa    36240
caccaggcat gattctgttc cgcataatta ctcctgataa ttaatcctta actttgccca    36300
cctgcctttt aaaacattcc agtatatcac ttttcattct tgcgtagcaa tatgccatct    36360
cttcagctat ctcagcattg gtgaccttgt tcagaggcgc tgagagatgg ccttttttctg    36420 atagataatg ttctgttaaa atatctccgg cctcatcttt tgcccgcagg ctaatgtctg    36480
aaaattgagg tgacgggtta aaaataatat ccttggcaac cttttttata tccctttttaa    36540 attttggctt aatgactata tccaatgagt caaaaagctc cccttcaata tctgttgccc    36600
ctaagacctt taatatatcg ccaaatacag gtagcttggc ttctaccttc accgttgttc    36660
ggccgatgaa atgcatatgc ataacatcgt cttttggtggt tcccctcatc agtggctcta    36720
tctgaacgcg ctctccactg cttaatgaca ttcctttccc gattaaaaaa tctgtcagat    36780
cggatgtggt cggcccgaaa acagttctgg caaaaccaat ggtgtcgcct tcaacaaaca    36840
aaaaagatgg gaatcccaat gattcgtcat ctgcgaggct gttcttaata tcttcaactg    36900
aagctttaga gcgatttatc ttctgaacca gactcttgtc atttgttttg gtaaagagaa    36960 aagttttttcc atcgatttta tgaatataca aataattgga gccaacctgc aggtgatgat    37020
tatcagccag cagagaatta aggaaaacag acaggtttat tgagcgctta tctttcccctt    37080 tattttttgct gcggtaagtc gcataaaaac cattcttcat aattcaatcc atttactatg    37140
ttatgttctg aggggagtga aaattcccct aattcgatga agattcttgc tcaattgtta    37200
tcagctatgc gccgaccaga acaccttgcc gatcagccaa acgtctcttc aggccactga    37260
ctagcgataa ctttccccac aacgaacaa ctctcattgc atgggatcat tgggtactgt    37320
gggtttagtg gttgtaaaaa cacctgaccg ctatccctga tcagtttctt gaaggtaaac    37380
```

```
tcatcacccc caagtctggc tatgcagaaa tcacctggct caacagcctg ctcagggtca    37440
acgagaatta acattccgtc aggaaagctt ggcttggagc ctgttggtgc ggtcatggaa    37500
ttaccttcaa cctcaagcca gaatgcagaa tcactggctt ttttggttgt gcttacccat    37560
ctctccgcat cacctttggt aaaggttcta agcttaggtg agaacatccc tgcctgaaca    37620
tgagaaaaaa cagggtactc atactcactt ctaagtgacg gctgcatact aaccgcttca    37680
tacatctcgt agatttctct ggcgattgaa gggctaaatt cttcaacgct aactttgaga    37740
attttttgtaa gcaatgcggc gttataagca tttaatgcat tgatgccatt aaataaagca    37800
ccaacgcctg actgcccat ccccatcttg tctgcgacag attcctggga taagccaagt    37860
tcattttct ttttttcata aattgcttta aggcgacgtg cgtcctcaag ctgctcttgt    37920
gttaatggtt tctttttgt gctcatacgt taaatctatc accgcaaggg ataaatatct    37980
aacaccgtgc gtgttgacta ttttacctct ggcggtgata atggttgcat gtactaagga    38040
ggttgtatgg aacaacgcat aaccctgaaa gattatgcaa tgcgctttgg gcaaaccaag    38100
acagctaaag atctcggcgt atatcaaagc gcgatcaaca aggccattca tgcaggccga    38160
aagattttt taactataaa cgctgatgga agcgtttatg cggaagaggt aaagcccttc    38220
ccgagtaaca aaaaaacaac agcataaata accccgctct tacacattcc agccctgaaa    38280
aagggcatca aattaaacca cacctatggt gtatgcattt atttgcatac attcaatcaa    38340
ttgttatcta aggaaatact tacatatggt tcgtgcaaac aaacgcaacg aggctctacg    38400
aatcgagagt gcgttgctta acaaaatcgc aatgcttgga actgagaaga cagcggaagc    38460
tgtgggcgtt gataagtcgc agatcagcag gtggaagagg actggattc caaagttctc    38520
aatgctgctt gctgttcttg aatgggggt cgttgacgac gacatggctc gattggcgcg    38580
acaagttgct gcgattctca ccaataaaaa acgcccggcg gcaaccgagc gttctgaaca    38640
aatccagatg gagttctgag gtcattactg gatctatcaa caggagtcat tatgacaaat    38700
acagcaaaaa tactcaactt cggcagaggt aactttgccg gacaggagcg taatgtggca    38760
gatctcgatg atggttacgc cagactatca aatatgctgc ttgaggctta tccgggcgca    38820
gatctgacca agcgacagtt taaagtgctg cttgccattc tgcgtaaaac ctatgggtgg    38880
aataaaccaa tggacagaat caccgattct caacttagcg agattacaaa gttacctgtc    38940
aaacggtgca atgaagccaa gttagaactc gtcagaatga atattatcaa gcagcaaggc    39000
ggcatgtttg gaccaaataa aaacatctca gaatggtgca tccctcaaaa cgagggaaaa    39060
tccctaaaa cgagggataa aacatccctc aaattggggg attgctatcc ctcaaaacag    39120
ggggacacaa aagacactat tacaaagaa aaagaaaag attattcgtc agagaattct    39180
ggcgaatcct ctgaccagcc agaaaacgac ctttctgtgg tgaaaccgga tgctgcaatt    39240
cagagcggca gcaagtgggg gacagcagaa gacctgaccg ccgcagagtg gatgtttgac    39300
atggtgaaga ctatcgcacc atcagccaga aaaccgaatt ttgctgggtg gctaacgat    39360
atccgcctga tgcgtgaacg tgacggacgt aaccaccgcg acatgtgtgt gctgttccgc    39420
tgggcatgcc aggacaactt ctggtccggt aacgtgctga gcccggccaa actccgcgat    39480
aagtggaccc aactcgaaat caaccgtaac aagcaacagg caggcgtgac agccagcaaa    39540
ccaaaactcg acctgacaaa cacagactgg atttacgggg tggatctatg aaaaacatcg    39600
ccgcacagat ggttaacttt gaccgtgagc agatgcgtcg gatcgccaac aacatgccgg    39660
aacagtacga cgaaaagccg caggtacagc aggtagcgca gatcatcaac ggtgtgttca    39720
gccagttact ggcaactttc ccggcgagcc tggctaaccg tgaccagaac gaagtgaacg    39780
```

```
aaatccgtcg ccagtgggtt ctggcttttc gggaaaacgg gatcaccacg atggaacagg   39840
ttaacgcagg aatgcgcgta gcccgtcggc agaatcgacc atttctgcca tcacccgggc   39900
agtttgttgc atggtgccgg gaagaagcat ccgttaccgc cggactgcca aacgtcagcg   39960
agctggttga tatggtttac gagtattgcc ggaagcgagg cctgtatccg gatgcggagt   40020
cttatccgtg gaaatcaaac gcgcactact ggctggttac caacctgtat cagaacatgc   40080
gggccaatgc gcttactgat gcggaattac gccgtaaggc cgcagatgag cttgtccata   40140
tgactgcgag aattaaccgt ggtgaggcga tccctgaacc agtaaaacaa cttcctgtca   40200
tgggcggtag acctctaaat cgtgcacagg ctctggcgaa gatcgcagaa atcaaagcta   40260
agttcggact gaaaggagca agtgtatgac gggcaaagag gcaattattc attacctggg   40320
gacgcataat agcttctgtg cgccggacgt tgccgcgcta acaggcgcaa cagtaaccag   40380
cataaatcag gccgcggcta aaatggcacg ggcaggtctt ctggttatcg aaggtaaggt   40440
ctggcgaacg gtgtattacc ggtttgctac cagggaagaa cgggaaggaa agatgagcac   40500
gaacctggtt tttaaggagt gtcgccagag tgccgcgatg aaacgggtat tggcggtata   40560
tggagttaaa agatgaccat ctacattact gagctaataa caggcctgct ggtaatcgca   40620 ggcctttttta tttgggggag agggaagtca tgaaaaaact aacctttgaa attcgatctc   40680
cagcacatca gcaaaacgct attcacgcag tacagcaaat ccttccagac ccaaccaaac   40740
caatcgtagt aaccattcag gaacgcaacc gcagcttaga ccaaaacagg aagctatggg   40800
cctgcttagg tgacgtctct cgtcaggttg aatggcatgg tcgctggctg gatgcagaaa   40860
gctggaagtg tgtgttttacc gcagcattaa agcagcagga tgttgttcct aaccttgccg   40920
ggaatggctt tgtggtaata ggccagtcaa ccagcaggat gcgtgtaggc gaatttgcgg   40980
agctattaga gcttatacag gcattcggta cagagcgtgg cgttaagtgg tcagacgaag   41040
cgagactggc tctggagtgg aaagcgagat ggggagacag ggctgcatga taaatgtcgt   41100
tagtttctcc ggtggcagga cgtcagcata tttgctctgg ctaatggagc aaaagcgacg   41160
ggcaggtaaa gacgtgcatt acgttttcat ggatacaggt tgtgaacatc caatgacata   41220
tcggtttgtc agggaagttg tgaagttctg ggatataccg ctcaccgtat tgcaggttga   41280
tatcaacccg gagcttggac agccaaatgg ttatacggta tgggaaccaa aggatattca   41340
gacgcgaatg cctgttctga agccatttat cgatatggta aagaaatatg gcactccata   41400
cgtcggcggc gcgttctgca ctgacagatt aaaactcgtt cccttcacca aatactgtga   41460
tgaccatttc gggcgaggga attacaccac gtggattggc atcagagctg atgaaccgaa   41520
gcggctaaag ccaaagcctg gaatcagata tcttgctgaa ctgtcagact ttgagaagga   41580
agatatcctc gcatggtgga agcaacaacc attcgatttg caaataccgg aacatctcgg   41640
taactgcata ttctgcatta aaaaatcaac gcaaaaaatc ggacttgcct gcaaagatga   41700
ggagggattg cagcgtgttt ttaatgaggt catcacggga tcccatgtgc gtgacggaca   41760
tcgggaaacg ccaaaggaga ttatgtaccg aggaagaatg tcgctggacg gtatcgcgaa   41820
aatgtattca gaaaatgatt atcaagcccct gtatcaggac atggtacgag ctaaaagatt   41880
cgataccggc tcttgttctg agtcatgcga aatatttgga gggcagcttg atttcgactt   41940
cgggagggaa gctgcatgat gcgatgttat cggtgcggtg aatgcaaaga agataaccgc   42000
ttccgaccaa atcaacctta ctggaatcga tggtgtctcc ggtgtgaaag aacaccaaca   42060 gggggtgttac cactaccgca ggaaaaggag gacgtgtggc gagacagcga cgaagtatca   42120
ccgacataat ctgcgaaaac tgcaaatacc ttccaacgaa acgcaccaga aataaaccca   42180
```

```
agccaatccc aaaagaatct gacgtaaaaa ccttcaacta cacggctcac ctgtgggata    42240
tccggtggct aagacgtcgt gcgaggaaaa caaggtgatt gaccaaaatc gaagttacga    42300
acaagaaagc gtcgagcgag ctttaacgtg cgctaactgc ggtcagaagc tgcatgtgct    42360
ggaagttcac gtgtgtgagc actgctgcgc agaactgatg agcgatccga atagctcgat    42420
gcacgaggaa gaagatgatg gctaaaccag cgcgaagacg atgtaaaaac gatgaatgcc    42480
gggaatggtt tcaccctgca ttcgctaatc agtggtggtg ctctccagag tgtgaaccaa    42540
agatagcact cgaacgacga agtaaagaac gcgaaaaagc ggaaaaagca gcagagaaga    42600
aacgacgacg agaggagcag aaacagaaag ataaacttaa gattcgaaaa ctcgccttaa    42660
agccccgcag ttactggatt aaacaagccc aacaagccgt aaacgccttc atcagagaaa    42720
gagaccgcga cttaccatgt atctcgtgcg gaacgctcac gtctgctcag tgggatgccg    42780
gacattaccg gacaactgct gcggcacctc aactccgatt taatgaacgc aatattcaca    42840
agcaatgcgt ggtgtgcaac cagcacaaaa gcggaaatct cgttccgtat cgcgtcgaac    42900
tgattagccg catcgggcag gaagcagtag acgaaatcga atcaaaccat aaccgccatc    42960
gctggactat cgaagagtgc aaggcgatca aggcagagta ccaacagaaa ctcaaagacc    43020
tgcgaaatag cagaagtgag gccgcatgac gttctcagta aaaaccattc cagacatgct    43080
cgttgaaaca tacggaaatc agacagaagt agcacgcaga ctgaaatgta gtcgcggtac    43140
ggtcagaaaa tacgttgatg ataaagacgg gaaaatgcac gccatcgtca acgacgttct    43200
catggttcat cgcggatgga gtgaaagaga tgcgctatta cgaaaaaatt gatggcagca    43260
aataccgaaa tatttgggta gttggcgatc tgcacggatg ctacgcgaac ctgatgaaca    43320
aactggatac gattggattc gacaacaaaa aagacctgct tatctcggtg ggcgatttgg    43380
ttgatcgtgg tgcagagaac gttgaatgcc tggaattaat cacattcccc tggttcagag    43440
ctgtacgtgg aaaccatgag caaatgatga ttgatggctt atcagagcgt ggaaacgtta    43500
atcactggct gcttaatggc ggtggctggt tctttaatct cgattacgac aaagaaattc    43560
tggctaaagc tcttgcccat aaagcagatg aacttccgtt aatcatcgaa ctggtgagca    43620
aagataaaaa atatgttatc tgccacgccg attatccctt tgacgaatac gagtttggaa    43680
agccagttga tcatcagcag gtaatctgga accgcgaacg aatcagcaac tcacaaaacg    43740
ggatcgtgaa agaaatcaaa ggcgcggaca cgttcatctt tggtcatacg ccagcagtga    43800
aaccactcaa gtttgccaac caaatgtata tcgataccgg cgcagtgttc tgcggaaacc    43860
taacattgat tcaggtacag ggagaaggcg catgagactc gaaagcgtag ctaaatttca    43920
ttcgccaaaa agcccgatga tgagcgactc accacgggcc acggcttctg actctctttc    43980
cggtactgat gtgatggctg ctatggggat ggcgcaatca caagccggat tcggtatggc    44040
tgcattctgc ggtaagcacg aactcagcca gaacgacaaa caaaaggcta tcaactatct    44100
gatgcaattt gcacacaagg tatcggggaa ataccgtggt gtggcaaagc ttgaaggaaa    44160
tactaaggca aaggtactgc aagtgctcgc aacattcgct tatgcggatt attgccgtag    44220
tgccgcgacg ccgggggcaa gatgcagaga ttgccatggt acaggccgtg cggttgatat    44280
tgccaaaaca gagctgtggg ggagagttgt cgagaaagag tgcggaagat gcaaaggcgt    44340
cggctattca aggatgccag caagcgcagc atatcgcgct gtgacgatgc taatcccaaa    44400
ccttacccaa cccacctggt cacgcactgt taagccgctg tatgacgctc tggtggtgca    44460
atgccacaaa gaagagtcaa tcgcagacaa catttttgaat gcggtcacac gttagcagca    44520
tgattgccac ggatggcaac atattaacgg catgatattg acttattgaa taaaattggg    44580
```

```
taaatttgac tcaacgatgg gttaattcgc tcgttgtggt agtgagatga aaagaggcgg   44640
cgcttactac cgattccgcc tagttggtca cttcgacgta tcgtctgaaa ctccaaccat   44700
cgcaggcaga gaggtctgca aaatgcaatc ccgaaacagt tcgcaggtaa tagttagagc   44760
ctgcataacg gtttcgggat tttttatatc tgcacaacag gtaagagcat tgagtcgata   44820
atcgtgaaga gtcggcgagc ctggttagcc agtgctcttt ccgttgtgct gaattaagcg   44880
aataccggaa gcagaaccgg atcaccaaat gcgtacaggc gtcatcgccg cccagcaaca   44940
gcacaaccca aactgagccg tagccactgt ctgtcctgaa ttcattagta atagttacgc   45000
tgcggccttt tacacatgac cttcgtgaaa gcgggtggca ggaggtcgcg ctaacaacct   45060
cctgccgttt tgcccgtgca tatcggtcac gaacaaatct gattactaaa cacagtagcc   45120
tggatttgtt ctatcagtaa tcgacccttat tcctaattaa atagagcaaa tcccctttatt   45180 gggggtaaga catgaagatg ccagaaaaac atgacctgtt ggccgccatt ctcgcggcaa   45240
aggaacaagg catcggggca atccttgcgt ttgcaatggc gtaccttcgc ggcagatata   45300
atggcggtgc gtttacaaaa acagtaatcg acgcaacgat gtgcgccatt atcgcctagt   45360
tcattcgtga ccttctcgac ttcgccggac taagtagcaa tctcgcttat ataacgagcg   45420
tgtttatcgg ctacatcggt actgactcga ttggttcgct tatcaaacgc ttcgctgcta   45480
aaaaagccgg agtagaagat ggtagaaatc aataatcaac gtaaggcgtt cctcgatatg   45540
ctggcgtggt cggagggaac tgataacgga cgtcagaaaa ccagaaatca tggttatgac   45600
gtcattgtag gcggagagct atttactgat tactccgatc accctcgcaa acttgtcacg   45660
ctaaacccaa aactcaaatc aacaggcgcc ggacgctacc agcttctttc ccgttggtgg   45720
gatgcctacc gcaagcagct tggcctgaaa gacttctctc cgaaaagtca ggacgctgtg   45780
gcattgcagc agattaagga gcgtggcgct ttacctatga ttgatcgtgg tgatatccgt   45840
caggcaatcg accgttgcag caatatctgg gcttcactgc cgggcgctgg ttatggtcag   45900
ttcgagcata aggctgacag cctgattgca aaattcaaag aagcgggcgg aacggtcaga   45960
gagattgatg tatgagcaga gtcaccgcga ttatctccgc tctggttatc tgcatcatcg   46020
tctgcctgtc atgggctgtt aatcattacc gtgataacgc cattacctac aaagcccagc   46080
gcgacaaaaa tgccagagaa ctgaagctgg cgaacgcggc aattactgac atgcagatgc   46140
gtcagcgtga tgttgctgcg ctcgatgcaa aatacacgaa ggagttagct gatgctaaag   46200
ctgaaaatga tgctctgcgt gatgatgttg ccgctggtcg tcgtcggttg cacatcaaag   46260
cagtctgtca gtcagtgcgt gaagccacca ccgcctccgg cgtggataat gcagcctccc   46320
cccgactggc agacaccgct gaacgggatt atttcaccct cagagagagg ctgatcacta   46380
tgcaaaaaca actggaagga acccagaagt atattaatga gcagtgcaga tagagttgcc   46440
catatcgatg ggcaactcat gcaattattg tgagcaatac acacgcgctt ccagcggagt   46500
ataaatgcct aaagtaataa aaccgagcaa tccatttacg aatgtttgct gggtttctgt   46560
tttaacaaca ttttctgcgc cgccacaaat tttggctgca tcgacagttt tcttctgccc   46620
aattccagaa acgaagaaat gatgggtgat ggtttccttt ggtgctactg ctgccggttt   46680
gttttgaaca gtaaacgtct gttgagcaca tcctgtaata agcagggcca gcgcagtagc   46740
gagtagcatt ttttttcatgg tgttattccc gatgcttttt gaagttcgca gaatcgtatg   46800
tgtagaaaat taaacaaacc ctaaacaatg agttgaaatt tcatattgtt aatatttatt   46860
aatgtatgtc aggtgcgatg aatcgtcatt gtattcccgg attaactatg tccacagccc   46920
tgacggggaa cttctctgcg ggagtgtccg ggaataatta aaacgatgca cacagggttt   46980
```

| | | | | |
|---|---|---|---|---|
| agcgcgtaca | cgtattgcat | tatgccaacg | ccccggtgct | gacacggaag | aaaccggacg | 47040 |
| ttatgattta | gcgtggaaag | atttgtgtag | tgttctgaat | gctctcagta | aatagtaatg | 47100 |
| aattatcaaa | ggtatagtaa | tatcttttat | gttcatggat | atttgtaacc | catcggaaaa | 47160 |
| ctcctgcttt | agcaagattt | tccctgtatt | gctgaaatgt | gatttctctt | gatttcaacc | 47220 |
| tatcatagga | cgtttctata | agatgcgtgt | ttcttgagaa | tttaacattt | acaaccttt | 47280 |
| taagtccttt | tattaacacg | gtgttatcgt | tttctaacac | gatgtgaata | ttatctgtgg | 47340 |
| ctagatagta | aatataatgt | gagacgttgt | gacgttttag | ttcagaataa | aacaattcac | 47400 |
| agtctaaatc | ttttcgcact | tgatcgaata | tttctttaaa | aatggcaacc | tgagccattg | 47460 |
| gtaaaacctt | ccatgtgata | cgagggcgcg | tagtttgcat | tatcgttttt | atcgtttcaa | 47520 |
| tctggtctga | cctccttgtg | ttttgttgat | gatttatgtc | aaatattagg | aatgttttca | 47580 |
| cttaatagta | ttggttgcgt | aacaaagtgc | ggtcctgctg | gcattctgga | gggaaataca | 47640 |
| accgacagat | gtatgtaagg | ccaacgtgct | caaatcttca | tacagaaaga | tttgaagtaa | 47700 |
| tattttaacc | gctagatgaa | gagcaagcgc | atggagcgac | aaaatgaata | aagaacaatc | 47760 |
| tgctgatgat | ccctccgtgg | atctgattcg | tgtaaaaaat | atgcttaata | gcaccatttc | 47820 |
| tatgagttac | cctgatgttg | taattgcatg | tatagaacat | aaggtgtctc | tggaagcatt | 47880 |
| cagagcaatt | gaggcagcgt | tggtgaagca | cgataataat | atgaaggatt | attccctggt | 47940 |
| ggttgactga | tcaccataac | tgctaatcat | tcaaactatt | tagtctgtga | cagagccaac | 48000 |
| acgcagtctg | tcactgtcag | gaaagtggta | aaactgcaac | tcaattactg | caatgccctc | 48060 |
| gtaattaagt | gaatttacaa | tatcgtcctg | ttcggaggga | agaacgcggg | atgttcattc | 48120 |
| ttcatcactt | ttaattgatg | tatatgctct | cttttctgac | gttagtctcc | gacggcaggc | 48180 |
| ttcaatgacc | caggctgaga | aattcccgga | cccttttgc | tcaagagcga | tgttaatttg | 48240 |
| ttcaatcatt | tggttaggaa | agcggatgtt | gcgggttgtt | gttctgcggg | ttctgttctt | 48300 |
| cgttgacatg | aggttgcccc | gtattcagtg | tcgctgattt | gtattgtctg | aagttgtttt | 48360 |
| tacgttaagt | tgatgcagat | caattaatac | gatacctgcg | tcataattga | ttatttgacg | 48420 |
| tggtttgatg | gcctccacgc | acgttgtgat | atgtagatga | taatcattat | cactttacgg | 48480 |
| gtcctttccg | gtgatccgac | aggttacggg | gcggcgacct | cgaaaa | | 48526 |

<210> SEQ ID NO 4
<211> LENGTH: 5955
<212> TYPE: DNA
<213> ORGANISM: Artificial Sequence
<220> FEATURE:
<223> OTHER INFORMATION: Artificial Operon

<400> SEQUENCE: 4

| | | | | |
|---|---|---|---|---|
| attaggcctg | tttggccgtg | acaccggaca | atgagtaatg | tcgcaaaatg | tgtacattgt | 60 |
| ctcaaccgca | cgcactccga | ttggctcctt | ccaaggctcg | ttgtcttcta | agacggccgt | 120 |
| agaactgggc | gcggtggcgt | taaaggagc | actggcgaag | gtgccggaac | tggatgcctc | 180 |
| taaggatttt | gacgaaatta | tttttggcaa | tgtgctctcg | gcaaacctgg | acaggcgcc | 240 |
| cgcacgccag | gtggcgctgg | cggcaggcct | gagcaaccat | atagtggcca | gtacggtgaa | 300 |
| taaggtttgc | gcctctgcga | tgaaggccat | aattctgggc | gcgcagtcta | taaaatgcgg | 360 |
| caacgcggat | gtggttgtcg | cgggcggctg | cgaatcgatg | accaatgccc | cgtactacat | 420 |
| gccgccgca | cgggctggcg | caaaatttgg | acagaccgtg | ctcgtggatg | gcgttgaacg | 480 |
| cgatgggctg | aatgatgctt | acgatggctt | ggcaatgggc | gtccacgccg | aaaagtgcgc | 540 |

-continued

```
acgggattgg gatattaccc gcgaacagca ggacaacttt gcaatagaat cttaccagaa    600
atcgcagaaa tcgcagaagg aaggcaaatt cgacaacgaa attgtcccag tgactattaa    660
gggttttcgc ggcaagccag atacccaggt tacaaaggac gaggaaccag cgcgcttaca    720
cgtggaaaaa ctgcgctcgg cccgtaccgt gttccagaaa gaaatggcca ccgtgaccgc    780
agcgaatgcg tcgccgataa atgatggcgc ggccgcagtt atactggtgt ctgaaaaagt    840
gctgaaggaa aagaacctga agccactggc gattataaaa ggctgggggcg aggcagcgca    900
tcagccggcg gattttacgt gggcgccgtc gctcgccgtg ccgaaggcgc tgaaacatgc    960
gggaatagaa gacataaact cggtggatta ctttgaattc aacgaagcat tttcagtggt   1020
tggcctggta ataccaaga ttctgaagtt ggacccgtcg aaggtgaacg tctatggcgg   1080
cgcggtggcg ttgggccacc cgctgggctg ctcgggcgcg cgcgtagtgg tgacgctttt   1140
gtctatatta caacaggaag gtggcaagat aggcgtggca gcaatttgca acggcggcgg   1200
cggcgcgtct tcgattgtta ttgaaaagat ctaaggcctt gatggccaac gcgggagatt   1260
tttcatgaaa ctatccacca aactctgctg gtgcggcatt aaaggtcgcc tccgtcccca   1320
gaagcagcag cagttacaca acacgaatct gcagatgacc gaattgaaaa aacagaagac   1380
tgcggaacag aaaactcgcc cacagaacgt tggcattaaa ggcatacaga tttacatacc   1440
gacccagtgc gttaatcagt cggagttgga gaaatttgat ggagtgtcgc agggcaaata   1500
cacgattggc cttggacaga ctaatatgtc gtttgttaac gaccgcgaag atatatactc   1560
aatgtctttg accgtgctgt cgaagctgat aaagagctac aatatagaca ctaataaaat   1620
tggccgctta gaagttggca ccgaaaccct tattgacaag tctaagtcgg ttaagtcggt   1680
tctgatgcag ctgtttggcg aaaataccga cgttgaaggc attgacacac tcaacgcatg   1740
ctacggcggc actaatgctc tgttcaattc gctgaattgg attgaatcga atgcctggga   1800
tggccgcgac gcaattgtcg tgtgtggcga tattgcaata tacgataagg cgcagcccg   1860
cccgactggc ggcgcaggca ccgtggcgat gtggataggc ccagatgcgc cgattgtctt   1920
tgactcggtc cgcgcgtcgt acatggaaca cgcatacgat ttttacaagc cggatttcac   1980
tagtgaatat ccatacgttg atggccattt ttccttaacc tgctacgtta aggcgctcga   2040
tcaggtgtac aagagctatt ctaagaaggc gatttcgaaa gggctggtga gtgatcctgc   2100
gggctcagat gcgctgaatg tgctgaaata tttcgactac aatgtgttcc atgtgccgac   2160
ttgcaaactg gttacgaaat cctacggccg cttattgtat aatgatttcc gcgcaaaccc   2220
acagctgttc ccggaagtgg acgcagaatt agcgaccaga gattatgacg aatcgttaac   2280
tgataagaat attgaaaaaa cctttgtgaa cgtggcgaag ccgttccaca aagagcgcgt   2340
ggcacagtcg ctgattgtgc cgacgaatac gggcaatatg tacactgcct cggtgtatgc   2400
agcatttgcc tcgttgttaa attatgtggg ttcggacgac ttacagggaa agcgggtggg   2460
cttattttcg tacggctctg gcttagcggc ctcgttgtat tcgtgtaaaa ttgtgggcga   2520
cgttcagcat attataaagg aattagatat taccaataaa ttagcaaagc gcataactga   2580
aaccccgaag gattacgaag cggcaataga actgcgcgaa aacgcacatc tgaagaagaa   2640
tttcaaacca cagggctcta ttgagcatct gcagagcggc gtgtactacc tgactaatat   2700
agatgacaaa tttcgccgct cgtacgatgt gaaaaaataa ggcctcgatg gccgtgaact   2760
ggatagtgaa ataatgcccc ccttgttcaa gggtcttaaa caaatggcca agccgattgc   2820
atatgtgtcc cgcttttcag ctaaacgacc gattcatatc atcctctttt cgttgataat   2880
ctctgccttc gcgtatttgt ctgttattca atattacttc aacggctggc agttggattc   2940
```

```
caacagcgtg tttgaaaccg cgccgaacaa agactctaat accttgtttc aggaatgctc    3000
tcattactac cgcgattctt cgttggatgg ctgggtctcc ataactgctc atgaagcgag    3060
cgagttaccg gcaccgcacc attactattt gttaaatctt aatttcaaca gcccaaacga    3120
aaccgactct attccggaat tggcgaatac agtgtttgag aaagataaca cgaaatatat    3180
tcttcaggaa gatctaagcg tgtctaaaga aatttcgtcg accgatggta caaaatggcg    3240
tttacgcagc gaccgcaaaa gcctcttcga cgtcaagaca ttagcctatt cgctatacga    3300
tgtcttttcc gaaaacgtca ctcaggccga ccccttttgac gttctcatta tggtgaccgc    3360
atacttgatg atgttctaca ctatcttcgg actattcaac gacatgcgta agactgggtc    3420
caacttttgg ctgagtgcat cgacggtagt taactcggcc tcctccctct tcttagccct    3480
gtatgttact cagtgcattt tgggaaaaga agtgtctgcc ttaaccctct ttgaaggcct    3540
gccattcatt gtcgtggtgg tgggcttcaa gcacaaaata aagattgcac aatatgcact    3600
tgagaaattt gaacgcgttg gcttatcgaa acgtattacc actgatgaaa tagtgtttga    3660
atctgtaagt gaagagggcg gccggctgat tcaggaccat ctgctctgca tttttgcatt    3720
tataggttgt tcgatgtatg cgcaccagct gaagaccctg acgaatttct gtatcttatc    3780
cgcctttata ttgattttg aactgatttt aaccccaacg ttttattcgg cgatattagc    3840
tctccgcctt gaaatgaacg tgatacaccg ctcgaccatt ataaagcaga cgttagaaga    3900
agacggcgtg gtgccgtcga cggcccgcat aatttcgaaa gccgaaaaga aatctgtctc    3960
gtcgttctta aacctaagcg tagtggttat tataatgaaa ctatcggtta tccttctgtt    4020
tgttttcata aattttttata attttggcgc caactgggtt aacgatgcat tcaactccct    4080
gtacttcgat aaggaacggg tgtcgttgcc ggattttatt acttcaaacg catcggaaaa    4140
ttttaaagag caggcgattg tgagcgttac tccgttatta tattacaaac ctattaagtc    4200
ttaccagaga attgaggata tggtgctctt gctgctccgg aacgttagcg tggcaattcg    4260
ggatcgtttc gttagcaaat tagtgctctc tgcattagtc tgtagcgcgg ttataaacgt    4320
atatttactg aacgcggcgc gcattcatac tagctatacc gccgaccagc tggtaaaaac    4380
cgaagttact aagaagtcgt ttaccgcgcc agtccagaag gcgtcgacgc cggtgttaac    4440
taacaaaacg gttatttcgg gttcaaaagt taaaagctta tcctcggctc agtcaagttc    4500
ctccggtcca tcctcctcga gcaggaagaa tgattctaga gatattgaaa gtctggataa    4560
gaaaatccgg ccattagaag aattagaagc cttattaagc agcggtaaca cgaaacagct    4620
gaagaataaa gaggttgcgg cactggtgat tcacggcaag ttaccactgt acgcgctgga    4680
gaaaaaatta ggcgatacca cacgcgctgt ggctgtccgg cgtaaggcgc tctccattct    4740
ggccgaagcg ccagtcttag cctcggatcg gttaccgtat aaaaactatg actacgacag    4800
agtctttgga gcgtgctgcg aaaacgtgat cggctacatg ccactgcctg tgggcgtgat    4860
cggacctctg gtgatagatg gcacgtcgta tcatatcccg atggccacca cggagggctg    4920
cctggtcgcg tcggcaatgc ggggatgcaa ggccataaac gcgggaggcg cgccacgac    4980
cgtgttaacc aaggatggca tgacgcgcgg accggtcgtt cggttcccga ccctgaaacg    5040
ctcgggcgca tgcaagatct ggttagactc cgaagagggt cagaatgcca ttaaaaaagc    5100
gtttaattcg acgtcccgct ttgcccggct tcagcatatt cagacctgct tggccggtga    5160
tttactattc atgcgctttc gcacgaccac cggcgacgcc atgggcatga acatgatttc    5220
gaaaggcgtt gaatactcct taaagcagat ggtcgaagag tatggatggg aagatatgga    5280
ggtggtttct gtgtcgggca attactgcac tgacaaaaaa ccggcggcaa taaattggat    5340
```

-continued

| | |
|---|---|
| agaaggccgg ggcaagagcg ttgttgccga agcgaccatt ccaggcgatg tggttcgcaa | 5400 |
| agtattaaaa agcgatgtgt ctgccctggt ggagctgaat attgcgaaga acctggtggg | 5460 |
| ttcggccatg gcggggtcgg tgggcggttt taatgcccat gccgcgaact tagtaacggc | 5520 |
| ggtgttcctg gccttaggtc aggatccagc ccagaacgtg gaaagctcta attgcatcac | 5580 |
| gctgatgaaa gaagtagacg gcgatctgcg catttctgtc tctatgccgt ctatagaagt | 5640 |
| cggcactata ggcggcggca ccgtgttgga accgcagggc gcaatgctgg acttattagg | 5700 |
| cgtccgcgga ccccatgcga ctgcgccagg cactaatgcc cggcagttag cccgcatcgt | 5760 |
| ggcatgcgca gttctggccg gcgaattatc tttatgcgcg gcattggccg caggacatct | 5820 |
| ggtgcagagc catatgactc acaatcgtaa accagcggaa ccgacgaaac caaataacct | 5880 |
| ggacgcaacc gatatcaacc ggctgaaaga tgggtctgtt acttgtatta aatcttaagg | 5940 |
| ccttcttggc caaaa | 5955 |

<210> SEQ ID NO 5
<211> LENGTH: 26
<212> TYPE: DNA
<213> ORGANISM: Artificial Sequence
<220> FEATURE:
<223> OTHER INFORMATION: Artificial Primer

<400> SEQUENCE: 5
tagggtctca aagcggccgc aagctt                                        26

<210> SEQ ID NO 6
<211> LENGTH: 25
<212> TYPE: DNA
<213> ORGANISM: Artificial Sequence
<220> FEATURE:
<223> OTHER INFORMATION: Artificial Primer

<400> SEQUENCE: 6
tagggtctca gcggccaaga aggcc                                         25

<210> SEQ ID NO 7
<211> LENGTH: 30
<212> TYPE: DNA
<213> ORGANISM: Artificial Sequence
<220> FEATURE:
<223> OTHER INFORMATION: Artificial Primer

<400> SEQUENCE: 7
tagggtctca ccgcccttcc cggtcgatat                                    30

<210> SEQ ID NO 8
<211> LENGTH: 42
<212> TYPE: DNA
<213> ORGANISM: Artificial Sequence
<220> FEATURE:
<223> OTHER INFORMATION: Artificial Primer

<400> SEQUENCE: 8
tagggtctca tattagctta attgttatcc gctcacaatt cc                      42

<210> SEQ ID NO 9
<211> LENGTH: 43
<212> TYPE: DNA
<213> ORGANISM: Artificial Sequence
<220> FEATURE:
<223> OTHER INFORMATION: Artificial Primer

<400> SEQUENCE: 9
tagggtctca ataactgga aaaaattagt gtctcatggt tcg                43

<210> SEQ ID NO 10
<211> LENGTH: 33
<212> TYPE: DNA
<213> ORGANISM: Artificial Sequence
<220> FEATURE:
<223> OTHER INFORMATION: Artificial Primer

<400> SEQUENCE: 10
tagggtctca gcttaagtgg tgggtagttg acc                          33

<210> SEQ ID NO 11
<211> LENGTH: 127
<212> TYPE: DNA
<213> ORGANISM: Artificial Sequence
<220> FEATURE:
<223> OTHER INFORMATION: MEV001

<400> SEQUENCE: 11
cacctgcacg tattaggcct gtttggccgt gacaccggac aatgagtaat gtcgcaaaat    60
gtgtacattg tctcaaccgc acgcactccg attggctcct tccaaggctc gttgtcacgt   120
gcaggtg                                                            127

<210> SEQ ID NO 12
<211> LENGTH: 140
<212> TYPE: DNA
<213> ORGANISM: Artificial Sequence
<220> FEATURE:
<223> OTHER INFORMATION: MEV002

<400> SEQUENCE: 12
cacctgcacg ttgtcttcta agacggccgt agaactgggc gcggtggcgt taaaaggagc    60
actggcgaag gtgccggaac tggatgcctc taaggatttt gacgaaatta ttttttggcaa   120 tgtgctctca cgtgcaggtg                                               140

<210> SEQ ID NO 13
<211> LENGTH: 129
<212> TYPE: DNA
<213> ORGANISM: Artificial Sequence
<220> FEATURE:
<223> OTHER INFORMATION: MEV003

<400> SEQUENCE: 13
cacctgcacg ttctcggcaa acctgggaca ggcgcccgca cgccaggtgg cgctggcggc    60
aggcctgagc aaccatatag tggccagtac ggtgaataag gtttgcgcct ctgcgatgac   120
gtgcaggtg                                                          129

<210> SEQ ID NO 14
<211> LENGTH: 136
<212> TYPE: DNA
<213> ORGANISM: Artificial Sequence
<220> FEATURE:
<223> OTHER INFORMATION: MEV004

<400> SEQUENCE: 14
cacctgcacg tgatgaaggc cataattctg ggcgcgcagt ctataaaatg cggcaacgcg    60
gatgtggttg tcgcgggcgg ctgcgaatcg atgaccaatg ccccgtacta catgccggcc   120
gcacgacgtg caggtg                                                  136

```
<210> SEQ ID NO 15
<211> LENGTH: 136
<212> TYPE: DNA
<213> ORGANISM: Artificial Sequence
<220> FEATURE:
<223> OTHER INFORMATION: MEV005

<400> SEQUENCE: 15
cacctgcacg tcacgggctg gcgcaaaatt tggacagacc gtgctcgtgg atggcgttga    60
acgcgatggg ctgaatgatg cttacgatgg cttggcaatg ggcgtccacg ccgaaaagtg   120
cgcacacgtg caggtg                                                   136

<210> SEQ ID NO 16
<211> LENGTH: 131
<212> TYPE: DNA
<213> ORGANISM: Artificial Sequence
<220> FEATURE:
<223> OTHER INFORMATION: MEV006

<400> SEQUENCE: 16
cacctgcacg tgcacgggat tgggatatta cccgcgaaca gcaggacaac tttgcaatag    60
aatcttacca gaaatcgcag aaatcgcaga aggaaggcaa attcgacaac gaaattgtcc   120
acgtgcaggt g                                                        131

<210> SEQ ID NO 17
<211> LENGTH: 135
<212> TYPE: DNA
<213> ORGANISM: Artificial Sequence
<220> FEATURE:
<223> OTHER INFORMATION: MEV007

<400> SEQUENCE: 17
cacctgcacg tgtcccagtg actattaagg gttttcgcgg caagccagat acccaggtta    60
caaaggacga ggaaccagcg cgcttacacg tggaaaaact gcgctcggcc cgtaccgtgt   120
tccaacgtgc aggtg                                                    135

<210> SEQ ID NO 18
<211> LENGTH: 138
<212> TYPE: DNA
<213> ORGANISM: Artificial Sequence
<220> FEATURE:
<223> OTHER INFORMATION: MEV008

<400> SEQUENCE: 18
cacctgcacg ttccagaaag aaaatggcac cgtgaccgca gcgaatgcgt cgccgataaa    60
tgatggcgcg gccgcagtta tactggtgtc tgaaaaagtg ctgaaggaaa agaacctgaa   120
gccactgacg tgcaggtg                                                 138

<210> SEQ ID NO 19
<211> LENGTH: 139
<212> TYPE: DNA
<213> ORGANISM: Artificial Sequence
<220> FEATURE:
<223> OTHER INFORMATION: MEV009

<400> SEQUENCE: 19
cacctgcacg tactggcgat tataaaaggc tggggcgagg cagcgcatca gccggcggat    60
tttacgtggg cgccgtcgct cgccgtgccg aaggcgctga acatgcggg aatagaagac   120 ataaactcac gtgcaggtg                                                139
```

```
<210> SEQ ID NO 20
<211> LENGTH: 133
<212> TYPE: DNA
<213> ORGANISM: Artificial Sequence
<220> FEATURE:
<223> OTHER INFORMATION: MEV010

<400> SEQUENCE: 20
cacctgcacg tactcggtgg attactttga attcaacgaa gcattttcag tggttggcct      60
ggtaaatacc aagattctga agttggaccc gtcgaaggtg aacgtctatg gcggcgcggt     120
ggacgtgcag gtg                                                       133

<210> SEQ ID NO 21
<211> LENGTH: 130
<212> TYPE: DNA
<213> ORGANISM: Artificial Sequence
<220> FEATURE:
<223> OTHER INFORMATION: MEV011

<400> SEQUENCE: 21
cacctgcacg tgtggcgttg ggccacccgc tgggctgctc gggcgcgcgc gtagtggtga      60
cgcttttgtc tatattacaa caggaaggtg gcaagatagg cgtggcagca atttgcaaca     120
cgtgcaggtg                                                           130

<210> SEQ ID NO 22
<211> LENGTH: 140
<212> TYPE: DNA
<213> ORGANISM: Artificial Sequence
<220> FEATURE:
<223> OTHER INFORMATION: MEV012

<400> SEQUENCE: 22
cacctgcacg tcaacggcgg cggcggcgcg tcttcgattg ttattgaaaa gatctaaggc      60
cttgatggcc aacgcgggag atttttcatg aaactatcca ccaaactctg ctggtgcggc     120
attaaaggta cgtgcaggtg                                                140

<210> SEQ ID NO 23
<211> LENGTH: 129
<212> TYPE: DNA
<213> ORGANISM: Artificial Sequence
<220> FEATURE:
<223> OTHER INFORMATION: MEV013

<400> SEQUENCE: 23
cacctgcacg taggtcgcct ccgtccccag aagcagcagc agttacacaa cacgaatctg      60
cagatgaccg aattgaaaaa acagaagact gcggaacaga aaactcgccc acagaacgac     120
gtgcaggtg                                                            129

<210> SEQ ID NO 24
<211> LENGTH: 136
<212> TYPE: DNA
<213> ORGANISM: Artificial Sequence
<220> FEATURE:
<223> OTHER INFORMATION: MEV014

<400> SEQUENCE: 24
cacctgcacg taacgttggc attaaaggca tacagattta cataccgacc cagtgcgtta      60
atcagtcgga gttggagaaa tttgatggag tgtcgcaggg caaatacacg attggccttg     120
gacagacgtg caggtg                                                    136
```

```
<210> SEQ ID NO 25
<211> LENGTH: 130
<212> TYPE: DNA
<213> ORGANISM: Artificial Sequence
<220> FEATURE:
<223> OTHER INFORMATION: MEV015

<400> SEQUENCE: 25
cacctgcacg tacagactaa tatgtcgttt gttaacgacc gcgaagatat atactcaatg      60
tctttgaccg tgctgtcgaa gctgataaag agctacaata tagacactaa taaaattgga     120
cgtgcaggtg                                                            130

<210> SEQ ID NO 26
<211> LENGTH: 136
<212> TYPE: DNA
<213> ORGANISM: Artificial Sequence
<220> FEATURE:
<223> OTHER INFORMATION: MEV016

<400> SEQUENCE: 26
cacctgcacg tttggccgct tagaagttgg caccgaaacc cttattgaca agtctaagtc      60
ggttaagtcg gttctgatgc agctgtttgg cgaaaatacc gacgttgaag gcattgacac     120
actcaacgtg caggtg                                                     136

<210> SEQ ID NO 27
<211> LENGTH: 137
<212> TYPE: DNA
<213> ORGANISM: Artificial Sequence
<220> FEATURE:
<223> OTHER INFORMATION: MEV017

<400> SEQUENCE: 27
cacctgcacg tctcaacgca tgctacggcg gcactaatgc tctgttcaat tcgctgaatt      60
ggattgaatc gaatgcctgg gatggccgcg acgcaattgt cgtgtgtggc gatattgcaa     120
tatacgacgt gcaggtg                                                    137

<210> SEQ ID NO 28
<211> LENGTH: 131
<212> TYPE: DNA
<213> ORGANISM: Artificial Sequence
<220> FEATURE:
<223> OTHER INFORMATION: MEV018

<400> SEQUENCE: 28
cacctgcacg ttacgataag ggcgcagccc gcccgactgg cggcgcaggc accgtggcga      60
tgtggatagg cccagatgcg ccgattgtct tgactcggt ccgcgcgtcg tacatggaac      120
acgtgcaggt g                                                          131

<210> SEQ ID NO 29
<211> LENGTH: 135
<212> TYPE: DNA
<213> ORGANISM: Artificial Sequence
<220> FEATURE:
<223> OTHER INFORMATION: MEV019

<400> SEQUENCE: 29
cacctgcacg tgaacacgca tacgattttt acaagccgga tttcactagt gaatatccat      60
acgttgatgg ccattttcc ttaacctgct acgttaaggc gctcgatcag gtgtacaaga      120
gctaacgtgc aggtg                                                      135
```

```
<210> SEQ ID NO 30
<211> LENGTH: 134
<212> TYPE: DNA
<213> ORGANISM: Artificial Sequence
<220> FEATURE:
<223> OTHER INFORMATION: MEV020

<400> SEQUENCE: 30
cacctgcacg tgctattcta agaaggcgat ttcgaaaggg ctggtgagtg atcctgcggg    60
ctcagatgcg ctgaatgtgc tgaaatattt cgactacaat gtgttccatg tgccgacttg   120
caaacgtgca ggtg                                                     134

<210> SEQ ID NO 31
<211> LENGTH: 135
<212> TYPE: DNA
<213> ORGANISM: Artificial Sequence
<220> FEATURE:
<223> OTHER INFORMATION: MEV021

<400> SEQUENCE: 31
cacctgcacg tgcaaactgg ttacgaaatc ctacggccgc ttattgtata atgatttccg    60
cgcaaaccca cagctgttcc cggaagtgga cgcagaatta gcgaccagag attatgacga   120
atcgacgtgc aggtg                                                    135

<210> SEQ ID NO 32
<211> LENGTH: 139
<212> TYPE: DNA
<213> ORGANISM: Artificial Sequence
<220> FEATURE:
<223> OTHER INFORMATION: MEV022

<400> SEQUENCE: 32
cacctgcacg tatcgttaac tgataagaat attgaaaaaa cctttgtgaa cgtggcgaag    60
ccgttccaca aagagcgcgt ggcacagtcg ctgattgtgc cgacgaatac gggcaatatg   120
tacactgcac gtgcaggtg                                                139

<210> SEQ ID NO 33
<211> LENGTH: 132
<212> TYPE: DNA
<213> ORGANISM: Artificial Sequence
<220> FEATURE:
<223> OTHER INFORMATION: MEV023

<400> SEQUENCE: 33
cacctgcacg tctgcctcgg tgtatgcagc atttgcctcg ttgttaaatt atgtgggttc    60
ggacgactta cagggaaagc gggtgggctt attttcgtac ggctctggct tagcggcctc   120
gacgtgcagg tg                                                       132

<210> SEQ ID NO 34
<211> LENGTH: 131
<212> TYPE: DNA
<213> ORGANISM: Artificial Sequence
<220> FEATURE:
<223> OTHER INFORMATION: MEV024

<400> SEQUENCE: 34
cacctgcacg tctcgttgta ttcgtgtaaa attgtgggcg acgttcagca tattataaag    60
gaattagata ttaccaataa attagcaaag cgcataactg aaaccccgaa ggattacgaa   120
acgtgcaggt g                                                        131
```

```
<210> SEQ ID NO 35
<211> LENGTH: 134
<212> TYPE: DNA
<213> ORGANISM: Artificial Sequence
<220> FEATURE:
<223> OTHER INFORMATION: MEV025

<400> SEQUENCE: 35
cacctgcacg tcgaagcggc aatagaactg cgcgaaaacg cacatctgaa gaagaatttc      60
aaaccacagg gctctattga gcatctgcag agcggcgtgt actacctgac taatatagat     120
gacacgtgca ggtg                                                       134

<210> SEQ ID NO 36
<211> LENGTH: 131
<212> TYPE: DNA
<213> ORGANISM: Artificial Sequence
<220> FEATURE:
<223> OTHER INFORMATION: MEV026

<400> SEQUENCE: 36
cacctgcacg ttgacaaatt tcgccgctcg tacgatgtga aaaataagg cctcgatggc       60 cgtgaactgg atagtgaaat aatgcccccc ttgttcaagg gtcttaaaca aatggccaag     120
acgtgcaggt g                                                         131

<210> SEQ ID NO 37
<211> LENGTH: 143
<212> TYPE: DNA
<213> ORGANISM: Artificial Sequence
<220> FEATURE:
<223> OTHER INFORMATION: MEV027

<400> SEQUENCE: 37
cacctgcacg tcaagccgat tgcatatgtg tcccgctttt cagctaaacg accgattcat      60
atcatcctct tttcgttgat aatctctgcc ttcgcgtatt tgtctgttat tcaatattac    120
ttcaacggct ggacgtgcag gtg                                            143

<210> SEQ ID NO 38
<211> LENGTH: 135
<212> TYPE: DNA
<213> ORGANISM: Artificial Sequence
<220> FEATURE:
<223> OTHER INFORMATION: MEV028

<400> SEQUENCE: 38
cacctgcacg tctggcagtt ggattccaac agcgtgtttg aaaccgcgcc gaacaaagac      60
tctaatacct tgtttcagga atgctctcat tactaccgcg attcttcgtt ggatggctgg    120
gtctacgtgc aggtg                                                     135

<210> SEQ ID NO 39
<211> LENGTH: 127
<212> TYPE: DNA
<213> ORGANISM: Artificial Sequence
<220> FEATURE:
<223> OTHER INFORMATION: MEV029

<400> SEQUENCE: 39
cacctgcacg tgtctccata actgctcatg aagcgagcga gttaccggca ccgcaccatt      60
actatttgtt aaatcttaat ttcaacagcc caaacgaaac cgactctatt ccggaaacgt    120
gcaggtg                                                              127
```

```
<210> SEQ ID NO 40
<211> LENGTH: 141
<212> TYPE: DNA
<213> ORGANISM: Artificial Sequence
<220> FEATURE:
<223> OTHER INFORMATION: MEV030

<400> SEQUENCE: 40
cacctgcacg tggaattggc gaatacagtg tttgagaaag ataacacgaa atatattctt      60
caggaagatc taagcgtgtc taaagaaatt cgtcgaccg atggtacaaa atggcgttta     120
cgcagcgacc acgtgcaggt g                                              141

<210> SEQ ID NO 41
<211> LENGTH: 126
<212> TYPE: DNA
<213> ORGANISM: Artificial Sequence
<220> FEATURE:
<223> OTHER INFORMATION: MEV031

<400> SEQUENCE: 41
cacctgcacg tgaccgcaaa agcctcttcg acgtcaagac attagcctat cgctatacg      60 atgtcttttc cgaaaacgtc actcaggccg acccctttga cgttctcatt atggtacgtg    120
caggtg                                                                126

<210> SEQ ID NO 42
<211> LENGTH: 136
<212> TYPE: DNA
<213> ORGANISM: Artificial Sequence
<220> FEATURE:
<223> OTHER INFORMATION: MEV032

<400> SEQUENCE: 42
cacctgcacg ttggtgaccg catacttgat gatgttctac actatcttcg gactattcaa     60
cgacatgcgt aagactgggt ccaactttg gctgagtgca tcgacggtag ttaactcggc     120
ctcctacgtg caggtg                                                    136

<210> SEQ ID NO 43
<211> LENGTH: 135
<212> TYPE: DNA
<213> ORGANISM: Artificial Sequence
<220> FEATURE:
<223> OTHER INFORMATION: MEV033

<400> SEQUENCE: 43
cacctgcacg ttcctccctc ttcttagccc tgtatgttac tcagtgcatt ttgggaaaag     60
aagtgtctgc cttaaccctc tttgaaggcc tgccattcat tgtcgtggtg gtgggcttca    120
agcaacgtgc aggtg                                                    135

<210> SEQ ID NO 44
<211> LENGTH: 141
<212> TYPE: DNA
<213> ORGANISM: Artificial Sequence
<220> FEATURE:
<223> OTHER INFORMATION: MEV034

<400> SEQUENCE: 44
cacctgcacg tagcacaaaa taaagattgc acaatatgca cttgagaaat ttgaacgcgt     60
tggcttatcg aaacgtatta ccactgatga aatagtgttt gaatctgtaa gtgaagaggg    120
cggccggctg acgtgcaggt g                                              141
```

<210> SEQ ID NO 45
<211> LENGTH: 124
<212> TYPE: DNA
<213> ORGANISM: Artificial Sequence
<220> FEATURE:
<223> OTHER INFORMATION: MEV035

<400> SEQUENCE: 45

```
cacctgcacg tgctgattca ggaccatctg ctctgcattt ttgcatttat aggttgttcg      60
atgtatgcgc accagctgaa gaccctgacg aatttctgta tcttatccgc cttacgtgca     120
ggtg                                                                  124
```

<210> SEQ ID NO 46
<211> LENGTH: 139
<212> TYPE: DNA
<213> ORGANISM: Artificial Sequence
<220> FEATURE:
<223> OTHER INFORMATION: MEV036

<400> SEQUENCE: 46

```
cacctgcacg tcctttatat tgattttga actgatttta accccaacgt tttattcggc      60
gatattagct ctccgccttg aaatgaacgt gatacaccgc tcgaccatta taaagcagac    120
gttagaagac gtgcaggtg                                                 139
```

<210> SEQ ID NO 47
<211> LENGTH: 136
<212> TYPE: DNA
<213> ORGANISM: Artificial Sequence
<220> FEATURE:
<223> OTHER INFORMATION: MEV037

<400> SEQUENCE: 47

```
cacctgcacg tgaagaagac ggcgtggtgc cgtcgacggc ccgcataatt tcgaaagccg     60
aaaagaaatc tgtctcgtcg ttcttaaacc taagcgtagt ggttattata atgaaactat    120
cggttacgtg caggtg                                                    136
```

<210> SEQ ID NO 48
<211> LENGTH: 131
<212> TYPE: DNA
<213> ORGANISM: Artificial Sequence
<220> FEATURE:
<223> OTHER INFORMATION: MEV038

<400> SEQUENCE: 48

```
cacctgcacg tggttatcct tctgtttgtt ttcataaatt tttataattt tggcgccaac     60
tgggttaacg atgcattcaa ctccctgtac ttcgataagg aacgggtgtc gttgccggat   120
acgtgcaggt g                                                        131
```

<210> SEQ ID NO 49
<211> LENGTH: 140
<212> TYPE: DNA
<213> ORGANISM: Artificial Sequence
<220> FEATURE:
<223> OTHER INFORMATION: MEV039

<400> SEQUENCE: 49

```
cacctgcacg tggattttat tacttcaaac gcatcggaaa attttaaaga gcaggcgatt    60
gtgagcgtta ctccgttatt atattacaaa cctattaagt cttaccagag aattgaggat   120
atggtgctca cgtgcaggtg                                               140
```

```
<210> SEQ ID NO 50
<211> LENGTH: 129
<212> TYPE: DNA
<213> ORGANISM: Artificial Sequence
<220> FEATURE:
<223> OTHER INFORMATION: MEV040

<400> SEQUENCE: 50
cacctgcacg tgctcttgct gctccggaac gttagcgtgg caattcggga tcgtttcgtt      60
agcaaattag tgctctctgc attagtctgt agcgcggtta taaacgtata tttactgaac     120
gtgcaggtg                                                             129

<210> SEQ ID NO 51
<211> LENGTH: 131
<212> TYPE: DNA
<213> ORGANISM: Artificial Sequence
<220> FEATURE:
<223> OTHER INFORMATION: MEV041

<400> SEQUENCE: 51
cacctgcacg tctgaacgcg gcgcgcattc atactagcta taccgccgac cagctggtaa      60
aaaccgaagt tactaagaag tcgtttaccg cgccagtcca aaggcgtcg acgccggtgt     120 acgtgcaggt g                                                          131

<210> SEQ ID NO 52
<211> LENGTH: 143
<212> TYPE: DNA
<213> ORGANISM: Artificial Sequence
<220> FEATURE:
<223> OTHER INFORMATION: MEV042

<400> SEQUENCE: 52
cacctgcacg tgtgttaact aacaaaacgg ttatttcggg ttcaaaagtt aaaagcttat      60
cctcggctca gtcaagttcc tccggtccat cctcctcgag cgaggaagat gattctagag     120
atattgaaag tcacgtgcag gtg                                             143

<210> SEQ ID NO 53
<211> LENGTH: 127
<212> TYPE: DNA
<213> ORGANISM: Artificial Sequence
<220> FEATURE:
<223> OTHER INFORMATION: MEV043

<400> SEQUENCE: 53
cacctgcacg tagtctggat aagaaaatcc ggccattaga agaattagaa gccttattaa      60
gcagcggtaa cacgaaacag ctgaagaata aagaggttgc ggcactggtg attcacacgt     120
gcaggtg                                                               127

<210> SEQ ID NO 54
<211> LENGTH: 136
<212> TYPE: DNA
<213> ORGANISM: Artificial Sequence
<220> FEATURE:
<223> OTHER INFORMATION: MEV044

<400> SEQUENCE: 54
cacctgcacg ttcacggcaa gttaccactg tacgcgctgg agaaaaaatt aggcgatacc      60
acacgcgctg tggctgtccg gcgtaaggcg ctctccattc tggccgaagc gccagtctta     120
gcctcacgtg caggtg                                                     136
```

```
<210> SEQ ID NO 55
<211> LENGTH: 132
<212> TYPE: DNA
<213> ORGANISM: Artificial Sequence
<220> FEATURE:
<223> OTHER INFORMATION: MEV045

<400> SEQUENCE: 55
cacctgcacg tcctcggatc ggttaccgta taaaaactat gactacgaca gagtctttgg      60
agcgtgctgc gaaaacgtga tcggctacat gccactgcct gtgggcgtga tcggacctct     120
gacgtgcagg tg                                                         132

<210> SEQ ID NO 56
<211> LENGTH: 135
<212> TYPE: DNA
<213> ORGANISM: Artificial Sequence
<220> FEATURE:
<223> OTHER INFORMATION: MEV046

<400> SEQUENCE: 56
cacctgcacg ttctggtgat agatggcacg tcgtatcata tcccgatggc caccacggag      60
ggctgcctgg tcgcgtcggc aatgcgggga tgcaaggcca taaacgcggg aggcggcgcc     120
acgaacgtgc aggtg                                                      135

<210> SEQ ID NO 57
<211> LENGTH: 138
<212> TYPE: DNA
<213> ORGANISM: Artificial Sequence
<220> FEATURE:
<223> OTHER INFORMATION: MEV047

<400> SEQUENCE: 57
cacctgcacg tacgaccgtg ttaaccaagg atggcatgac gcgcggaccg gtcgttcggt      60
tcccgaccct gaaacgctcg ggcgcatgca agatctggtt agactccgaa gagggtcaga     120
atgccatacg tgcaggtg                                                   138

<210> SEQ ID NO 58
<211> LENGTH: 132
<212> TYPE: DNA
<213> ORGANISM: Artificial Sequence
<220> FEATURE:
<223> OTHER INFORMATION: MEV048

<400> SEQUENCE: 58
cacctgcacg tccattaaaa aagcgtttaa ttcgacgtcc cgctttgccc ggcttcagca      60
tattcagacc tgcttggccg gtgatttact attcatgcgc tttcgcacga ccaccggcga     120
cacgtgcagg tg                                                         132

<210> SEQ ID NO 59
<211> LENGTH: 140
<212> TYPE: DNA
<213> ORGANISM: Artificial Sequence
<220> FEATURE:
<223> OTHER INFORMATION: MEV049

<400> SEQUENCE: 59
cacctgcacg tcgacgccat gggcatgaac atgatttcga aaggcgttga atactcctta      60
aagcagatgg tcgaagagta tggatgggaa gatatggagg tggtttctgt gtcgggcaat     120
tactgcacta cgtgcaggtg                                                 140
```

<210> SEQ ID NO 60
<211> LENGTH: 128
<212> TYPE: DNA
<213> ORGANISM: Artificial Sequence
<220> FEATURE:
<223> OTHER INFORMATION: MEV050

<400> SEQUENCE: 60
cacctgcacg tcactgacaa aaaaccggcg gcaataaatt ggatagaagg ccggggcaag     60
agcgttgttg ccgaagcgac cattccaggc gatgtggttc gcaaagtatt aaaaagcacg    120
tgcaggtg                                                            128

<210> SEQ ID NO 61
<211> LENGTH: 137
<212> TYPE: DNA
<213> ORGANISM: Artificial Sequence
<220> FEATURE:
<223> OTHER INFORMATION: MEV051

<400> SEQUENCE: 61
cacctgcacg taagcgatgt gtctgccctg gtggagctga atattgcgaa gaacctggtg     60
ggttcggcca tggcggggtc ggtgggcggt tttaatgccc atgccgcgaa cttagtaacg    120
gcggtgacgt gcaggtg                                                  137

<210> SEQ ID NO 62
<211> LENGTH: 133
<212> TYPE: DNA
<213> ORGANISM: Artificial Sequence
<220> FEATURE:
<223> OTHER INFORMATION: MEV052

<400> SEQUENCE: 62
cacctgcacg tggtgttcct ggccttaggt caggatccag cccagaacgt ggaaagctct     60
aattgcatca cgctgatgaa agaagtagac ggcgatctgc gcatttctgt ctctatgccg    120
tcacgtgcag gtg                                                      133

<210> SEQ ID NO 63
<211> LENGTH: 134
<212> TYPE: DNA
<213> ORGANISM: Artificial Sequence
<220> FEATURE:
<223> OTHER INFORMATION: MEV053

<400> SEQUENCE: 63
cacctgcacg tcgtctatag aagtcggcac tataggcggc ggcaccgtgt tggaaccgca     60
gggcgcaatg ctggacttat taggcgtccg cggaccccat gcgactgcgc caggcactaa    120
tgcacgtgca ggtg                                                     134

<210> SEQ ID NO 64
<211> LENGTH: 130
<212> TYPE: DNA
<213> ORGANISM: Artificial Sequence
<220> FEATURE:
<223> OTHER INFORMATION: MEV054

<400> SEQUENCE: 64
cacctgcacg tatgcccggc agttagcccg catcgtggca tgcgcagttc tggccggcga     60
attatcttta tgcgcggcat tggccgcagg acatctggtg cagagccata tgactcacaa    120
cgtgcaggtg                                                          130

```
<210> SEQ ID NO 65
<211> LENGTH: 138
<212> TYPE: DNA
<213> ORGANISM: Artificial Sequence
<220> FEATURE:
<223> OTHER INFORMATION: MEV055

<400> SEQUENCE: 65
cacctgcacg tcacaatcgt aaaccagcgg aaccgacgaa accaaataac ctggacgcaa        60
ccgatatcaa ccggctgaaa gatgggtctg ttacttgtat taaatcttaa ggccttcttg       120
gccaaaaacg tgcaggtg                                                     138
```